United States Patent [19]

Keese et al.

[11] Patent Number: 6,107,078
[45] Date of Patent: Aug. 22, 2000

[54] RIBOZYMES WITH OPTIMIZED HYBRIDIZING ARMS, STEMS, AND LOOPS, TRNA EMBEDDED RIBOZYMES AND COMPOSITIONS THEREOF

[75] Inventors: Paul Keese, Curtin; Marianne Stapper, Australian Capital Territory; Rhonda Perriman, O'Connor, all of Australia

[73] Assignee: Gene Shears Pty Limited, Canberra, Australia

[21] Appl. No.: 08/765,257

[22] PCT Filed: Jun. 21, 1995

[86] PCT No.: PCT/AU95/00359

§ 371 Date: May 5, 1997

§ 102(e) Date: May 5, 1997

[87] PCT Pub. No.: WO96/00232

PCT Pub. Date: Jan. 4, 1996

Related U.S. Application Data

[63] Continuation-in-part of application No. 08/265,484, Jun. 24, 1994.

[51] Int. Cl.[7] .......................... C07H 21/00; C07H 21/02; C12N 1/21; C12N 15/64
[52] U.S. Cl. .................. 435/252.3; 435/252.33; 435/320.1; 435/325; 435/419; 536/23.1; 536/24.5; 536/25.1
[58] Field of Search .................. 435/6, 91.31, 172.3, 435/252.3, 252.33, 320.1, 325, 358, 365, 375, 410, 419, 421, 455, 466, 468, 471; 514/44; 536/24.3, 24.5; 935/33, 34, 35, 38, 66, 67, 70, 72, 73

[56] References Cited

U.S. PATENT DOCUMENTS 5,254,678  10/1993  Haseloff et al. .................. 536/23.2

FOREIGN PATENT DOCUMENTS

| | | |
|---|---|---|
| B6499590 | 5/1991 | Australia . |
| B1824992 | 12/1992 | Australia . |
| 4420793 | 12/1993 | Australia . |
| 8905852 | 8/1989 | WIPO . |
| 9119789 | 12/1991 | WIPO . |
| 9315194 | 8/1993 | WIPO . |
| 9324133 | 12/1993 | WIPO . |
| 9413688 | 8/1994 | WIPO . |
| 9413833 | 8/1994 | WIPO . |
| 9419476 | 12/1994 | WIPO . |
| 9503404 | 2/1995 | WIPO . |
| 9506764 | 3/1995 | WIPO . |

OTHER PUBLICATIONS

Hampel et al. Hairpin catalytic RNA model: Evidence for helices and sequence requirement for substrate RNA. Nucleic Acids Res. 18(2): 299–304, Feb. 1990.

Cotten et al., (1989) "Ribozyme mediated destruction of RNA in vivo." *The EMBO Journal*, vol. 8, No. 12, pp. 3861–3866.

Haseloff et al., (1988) "Simple RNA enzymes with new and highly specific endoribonuclease activities." *Nature*, vol. 334, pp. 585–591.

*Primary Examiner*—Nancy Degen
*Assistant Examiner*—Thomas G. Larson
*Attorney, Agent, or Firm*—John P. White; Cooper & Dunham LLP

[57] ABSTRACT

This invention is directed to improved catalytic compounds, hammerhead ribozymes, capable of hybridizing with a target RNA to be cleaved. These improved compounds have optimized stems $(X)m*(X)m'$, loops $(X)b$ and hybridizing arms. The invention is also directed to compositions for enhanced RNA cleavage which comprise a first synthetic non-naturally occurring oligonucleotide compound which comprises nucleotides whose sequence defines a conserved catalytic region and nucleotides whose sequence is capable of hybridizing with a predetermined target sequence and a second synthetic non-naturally occurring oligonucleotide which does not contain the predetermined target sequence and is complementary to at least a portion of the first oligonucleotide compound. The invention is also directed to synthetic non-naturally occurring oligonucleotide compounds embedded in a tRNA. The ribozymes and compositions of the present invention may be used in vitro or in vivo. They may be used as diagnostic or therapeutic agents.

46 Claims, 23 Drawing Sheets

FIGURE 5 stem II

5'-UGAGUCC<sup>G</sup> U
   | | | | | | |
3'-AAGCAGG<sub>A</sub> G

Rz1 ΔG° -7.3  k_rel 1.0

5'-UGAGC<sup>G</sup> U
   | | | | |
3'-AAGCG<sub>A</sub> G

Rz2 ΔG° -3.4  k_rel 1.7

5'-UGAGAC<sup>G</sup> U
   | | | | | |
3'-AAGCUG<sub>A</sub> G

Rz3 ΔG° -4.4  k_rel 4.4

5'-UGAGCG<sup>G</sup> U
   | | | | | |
3'-AAGCGC<sub>A</sub> G

Rz4 ΔG° -5.4  k_rel 1.9

5'-UGAGCC<sup>G</sup> U
   | | | | | |
3'-AAGCGG<sub>A</sub> G

Rz5 ΔG° -6.3  k_rel 1.3

5'-UGAGU<sup>CUG</sup>U
   | | | | |
3'-AAGCA<sub>UGA</sub>G

Rz6 ΔG° -2.1  k_rel 0.11

5'-UGAGU<sup>CCG</sup>U
   | | | | |
3'-AAGCA<sub>AUA</sub>G

Rz7 ΔG° -2.1  k_rel 0.06

5'-UGAGU<sup>CCG</sup>U
   | | | | |
3'-AAGCA<sub>ACA</sub>G

Rz8 ΔG° -2.1  k_rel 0.02

5'-UGAGU<sup>CCG</sup>U
   | | | | |
3'-AAGCA<sub>UUA</sub>G

Rz9 ΔG° -2.1  k_rel 0.01

5'-UGAGU<sup>CCG</sup>U
   | | | | |
3'-AAGCA<sub>CAA</sub>G

Rz10 ΔG° -2.1  k_rel 0.01

5'-UGAGUC<sup>GG</sup>U
   | | | | | |
3'-AAGCAG<sub>GA</sub>G

Rz11 ΔG° -4.4  k_rel 0.4

5'-UGAGUC<sup>CG</sup>U
   | | | | | |
3'-AAGCAG<sub>AA</sub>G

Rz12 ΔG° -4.4  k_rel 0.09

5'-UGA<sup>U</sup>U
   | | |
3'-AAG<sub>U</sub>U

Rz13  k_rel 0.05

5'-UGAGAUC<sup>G</sup>U
   | | | | | | |
3'-AAGCUAG<sub>A</sub>G

Rz14 ΔG° -5.5  k_rel 0.44

5'-UGAGAUAC<sup>G</sup>U
   | | | | | | | |
3'-AAGCUAUG<sub>A</sub>G

Rz15 ΔG° -6.4  k_rel 0.19

5'-UGAGAUAUC<sup>G</sup>U
   | | | | | | | | |
3'-AAGCUAUAG<sub>A</sub>G

Rz16 ΔG° -7.5  k_rel 0.22

5'-UGAGAUAUAC<sup>G</sup>U
   | | | | | | | | | |
3'-AAGCUAUAUG<sub>A</sub>G

Rz17 ΔG° -8.4  k_rel 0.37

5'-UGAGAUAUAUC<sup>G</sup>U
   | | | | | | | | | | |
3'-AAGCUAUAUAG<sub>A</sub>G Rz18 ΔG° -9.5  k_rel 0.29

Rz19 5'-GAG-3'      Rz20 5'-GAC-3'      Rz21 5'-GUG-3'
k_rel 0.72          k_rel 0.7           k_rel 0.56

Rz22 5'-GGGA-3'     Rz23 5'-GUGG-3'     Rz24 5'-UGGC-3'     Rz25 5'-GUGU-3'
k_rel 2.3           k_rel 1.5           k_rel 1.0           k_rel 0.97

Rz26 5'-GGCA-3'     Rz27 5'-GUGC-3'     Rz28 5'-GUUA-3'     Rz29 5'-UCAG-3'
k_rel 0.78          k_rel 0.76          k_rel 0.6           k_rel 0.53

Rz30 5'-GACU-3'     Rz31 5'-GGGC-3'     Rz32 5'-UUCG-3'
k_rel 0.5           k_rel 0.4           k_rel 0.33

Rz33 5'-CGGAA-3'    Rz34 5'-UUGGA-3'    Rz35 5'-GUGUU-3'    Rz36 5'-UUCGA-3'
k_rel 1.6           k_rel 1.4           k_rel 0.95          k_rel 0.9

Rz37 5'-UGGGG-3'    Rz38 5'-GCUUA-3'
k_rel 0.7           k_rel 0.18

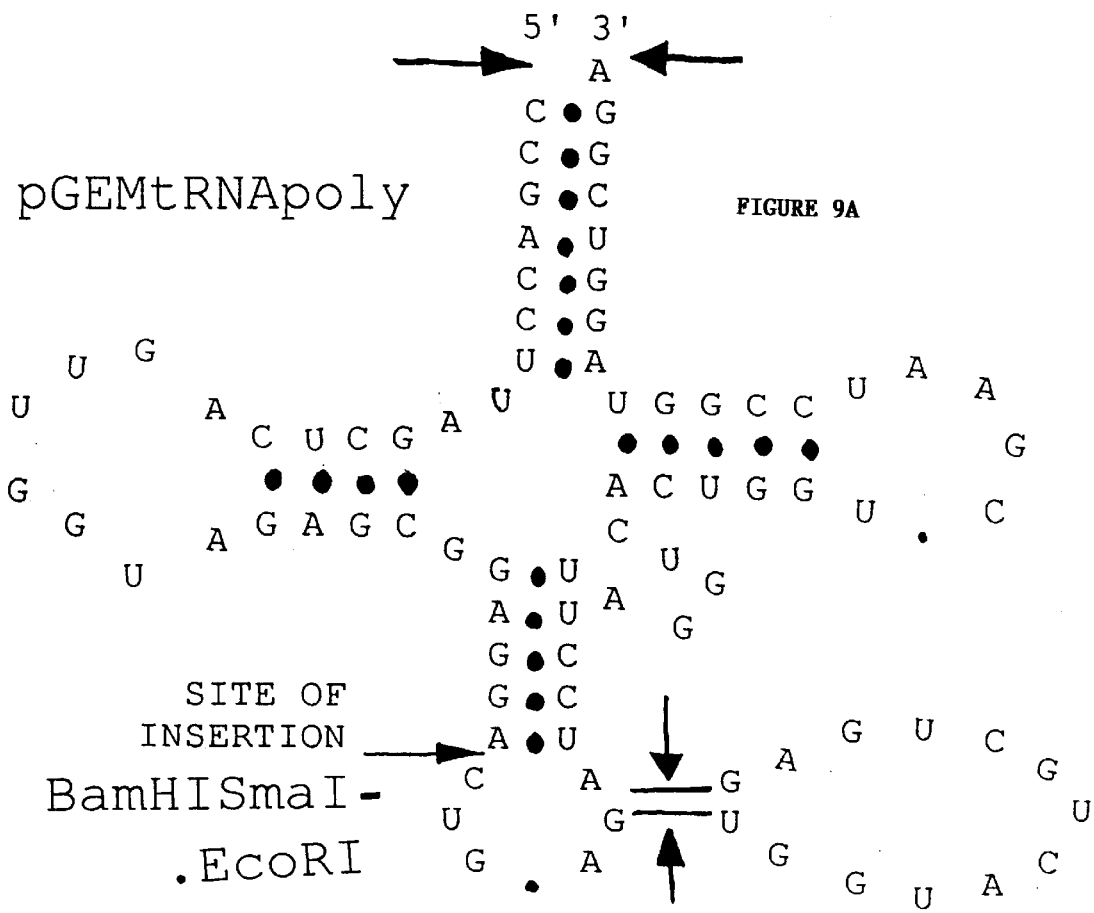
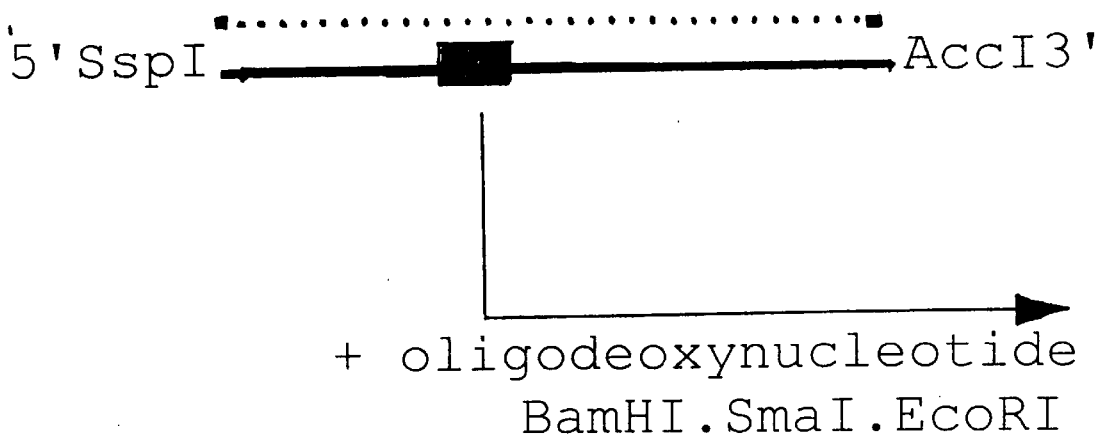

RIBOZYMES WITH OPTIMIZED HYBRIDIZING ARMS, STEMS, AND LOOPS, TRNA EMBEDDED RIBOZYMES AND COMPOSITIONS THEREOF

This application is a national stage application of PCT International Application No. PCT/AU95/0359, filed Jun. 21, 1995, which is a continuation-in-part of U.S. Ser. No. 08/265,484 filed Jun. 24, 1994. Throughout this application various references are cited in bracket by author and publication year. The full citations are listed alphabetically and may be found immediately preceding the claims. These publications are hereby incorporated by reference into the present application.

A portion of this work was funded under NSF Cooperative agreement BIR-8920216. Therefore, the U.S. Government has certain rights to this invention.

BACKGROUND OF THE INVENTION

The discovery that RNA molecules can function as enzymes revolutionized the understanding of chemistry in biological systems. It has now been demonstrated that RNA molecules can catalyze chemical transformations on themselves as well as on other RNA molecules [Castanotto, 1992]. The term ribozyme has been given to these RNA molecules. It has now become apparent that ribozymes play an important role in the biochemical function of many organisms.

Several types of ribozymes have been identified in living organisms. The first ribozyme to show catalytic turnover was RNA of ribonucleases P. Ribonucleases P (RNase P) cleaves precursor tRNAs (pre-tRNAs) at their 5' ends to give the mature 5'-termini of tRNAs. In *Escherichia coli* and *Bacillus subtilis*, the RNase P holoenzyme is composed of one basic protein subunit of approximate $M_r$ 14,000 (119 amino acids) and one single stranded RNA molecule of 377 and 401 nucleotides, respectively [Baer, 1990; Altman 1987; Waugh, 1989; Pace, 1990; Nichols, 1988]. The second ribozyme to show turnover was the L-19 intervening sequence (IVS) from tetrahymena. The 413 nucleotide intervening sequence (IVS) in the nuclear rRNA precursor from *Tetrahymena thermophila* can be excised and the two exons ligated in the complete absence of any protein [Kruger, 1982; Cech, 1981]. Unique to the *Tetrahymena thermophila* self-splicing reaction is the requirement of a guanosine or 5' guanosine nucleotide cofactor. The hammerhead self-cleavage reactions constitutes a third class of ribozymes. A number of plant pathogenic RNAs [Symons, 1989; Symons, 1990; Bruening, 1989; Bruening 1990], one animal viral RNA [Taylor, 1990] and a transcript from satellite II of DNA of the newt [Epstein, 1987; Epstein 1989] and from a Neurospora DNA plasmid [Saville, 1990] undergo a site specific self-cleavage reaction in vitro to produce cleavage fragments with a 2',3'-cyclic phosphate and a 5'-hydroxyl group. This self-cleavage reaction is non-hydrolytic, unlike RNases P RNA cleavage of pre-tRNAs, where the internucleotide bond undergoes a phosphoryl transfer reaction in the presence of $Mg^{++}$ or other divalent cations. Metal cations may be essential to RNA catalysis [Pyle, 1993]. Other reactions documented to date show that ribozymes can catalyze the cleavage of DNA [Robertson, 1990; Herschlag 1990], the replication of RNA strands [Green, 1992], the opening of 2'-3'-cyclic phosphate rings [Pan, 1992], as well as react with phosphate monoesters [Zaug, 1986] and carbon centers [Noller, 1992; Piccirilli, 1992]. Finally, ribozymes with new kinds of catalytic reactivity are being created through techniques of in vitro selection and evolution [Joyce, 1992].

The ability to specifically target and cleave a designated RNA sequence has led to much interest in the potential application of hammerhead ribozymes as gene therapy agents or drugs. One component to the success of treating a disease or targeting a specific RNA or DNA strand (substrate) to be cleaved is the optimization of the ribozyme/substrate complex. Optimization may be performed in vitro whereby a ribozyme is modified until it achieves maximum chemical activity on a target RNA or DNA molecule. While much success has been achieved in vitro in targeting and cleaving a number of designated RNA sequences (Saxena and Ackerman, 1990; Lamb and Hayes, 1991; Evans, et al., 1992; Mazzolini, et al., 1992; Homann, et al., 1993), the translation of this success into ribozyme action in the whole cell has been limited. This is particularly the case for plant systems, with only one example of ribozyme induced cleavage presently reported (Steinecke, et al., 1992). Thus, it is not entirely clear how the success in vitro would correlate to the success in vivo.

Previous reports have demonstrated that high levels of ribozyme expression are required to achieve reduced accumulation of target sequence in vivo [Cameron and Jennings, 1989; Cotten and Birnsteil, 1989; Sioud and Drilca, 1991; L'Huillier, et al., 1992; Perriman et al., 1993]. Additionally, a recent article suggests a necessity for the target and ribozyme to be sequestered in the same cellular compartment [Sullenger and Cech, 1993]. The results of several reports suggest that while the ribozyme molecule is clearly capable of inducing specific cleavage of a designated target RNA within a biological system, the rate limiting step, under in vivo conditions, is the formation of the active substrate/ribozyme hybrid. Such approaches towards optimizing the formation of the active substrate/ribozyme hybrid include attempts at "stabilizing" the ribozyme transcript by embedding the ribozyme within a stable RNA [Cameron and Jennings, 1989; Sioud, et al., 1992; Cotten and Birnsteil, 1989]. By providing the ribozyme transcript with a longer half-life, the chances of forming the desired hybrid with the target RNA are optimized.

In the approach of Cotten and Birnsteil (1989) a tRNA motif was used to deliver a hammerhead ribozyme to Xenopus oocytes and reduce the accumulation of a cytoplasmic target RNA. The embedded ribozyme was more effective than the analogous non-embedded ribozyme.

SUMMARY OF THE INVENTION

This invention is directed to improved catalytic compounds, hammerhead ribozymes, capable of hybridizing with a target RNA to be cleaved. These improved compounds have optimized stems $(X)m^*(X)m'$, loops $(X)b$ and hybridizing arms. The invention is also directed to compositions for enhanced RNA cleavage which comprise a first synthetic non-naturally occurring oligonucleotide compound which comprises nucleotides whose sequence defines a conserved catalytic region and nucleotides whose sequence is capable of hybridizing with a predetermined target sequence and a second synthetic non-naturally occurring oligonucleotide which does not contain the predetermined target sequence and is complementary to at least a portion of the first oligonucleotide compound. The invention is also directed to synthetic non-naturally occurring oligonucleotide compounds embedded in a tRNA.

The ribozymes and compositions of the present invention may be used in vitro or in vivo. They may be used as diagnostic or therapeutic agents.

BRIEF DESCRIPTION OF THE FIGURES

FIG. 3C shows the control and loop variants 1–6, FIG. 3B shows the control and loop variants 7–11, and FIG. 3C shows the control and loop variants 14, 15 and 21–24.

(FIG. 4A) Structure of the ribozyme/substrate complex represented as a wishbone, as determined by X-ray crystallography (Pley et al. 1994 A) and numbered according to Hertel et al. (1992). Nucleotides in bold correspond to the highly conserved catalyic core of naturally occurring hammerhead self-cleaving domains (Bruening 1989). Dashed lines depict non-canonical base pairs. (FIG. 4B) Time course of the parent ribozyme cleavage reaction, with error bars that correspond to standard deviation from ten experiments.

FIG. 5. Relative rate constants, $k^{rel}$ of ribozymes with mutations in stem II Rz 1 is the parent sequence, Rz 2–18 have sequence variations in the loop only. Free energy calculations according to Frier et al. (1986; kcal/mol at 37° C. in 1 M NaCl) were only for Watson Crick base paired sequences. Dashed lines depict non-canonical base-pairs.

FIGS. 9A–9D. Construction of plasmids for in vitro and in vivo analysis of non-embedded and tRNA-embedded ribozyme and antisense; and CAT and CM2, mutant CAT targets; (9a). 266 bp tyrosine tRNA sequence subcloned as SspI AccI fragment into pGEM3zf-(pGEMtRNA). Hatched box represents site of insertion of 10 bp Bam HI.SmaI.EcoRi polylinker at position 112 (pGEMtRNApoly). This is at the 5' end of the anticodon loop. Clover-leaf motif shows site of insertion of polylinker as well as 13 base loop out which is the endogenous intron. (9b). Sequence of hammerhead ribozyme Rz12 which is designed to anneal and cleave at position 464 on the CAT gene. (9c). 815 bp CAT sequence. Arrowed site is position 464, a GUC triplet targeted by Rz12. (9d). pACMV vector used for expression of ribozyme/antisense and target sequences in vivo. The RNA polymerase II coat protein promoter is indicated 5' of the polylinker region with termination and polyadenylation signals indicated 3'. All ribozyme/antisense and target sequences are subcloned within this region. The 670 bp duplication contains viral origin of replication. The pUC19-derived bacterial plasmid inserted at the ClaI site contains bacterial replication origin CoIEI and chloramphenicol resistance gene.

DETAILED DESCRIPTION OF THE INVENTION

Figure 1:
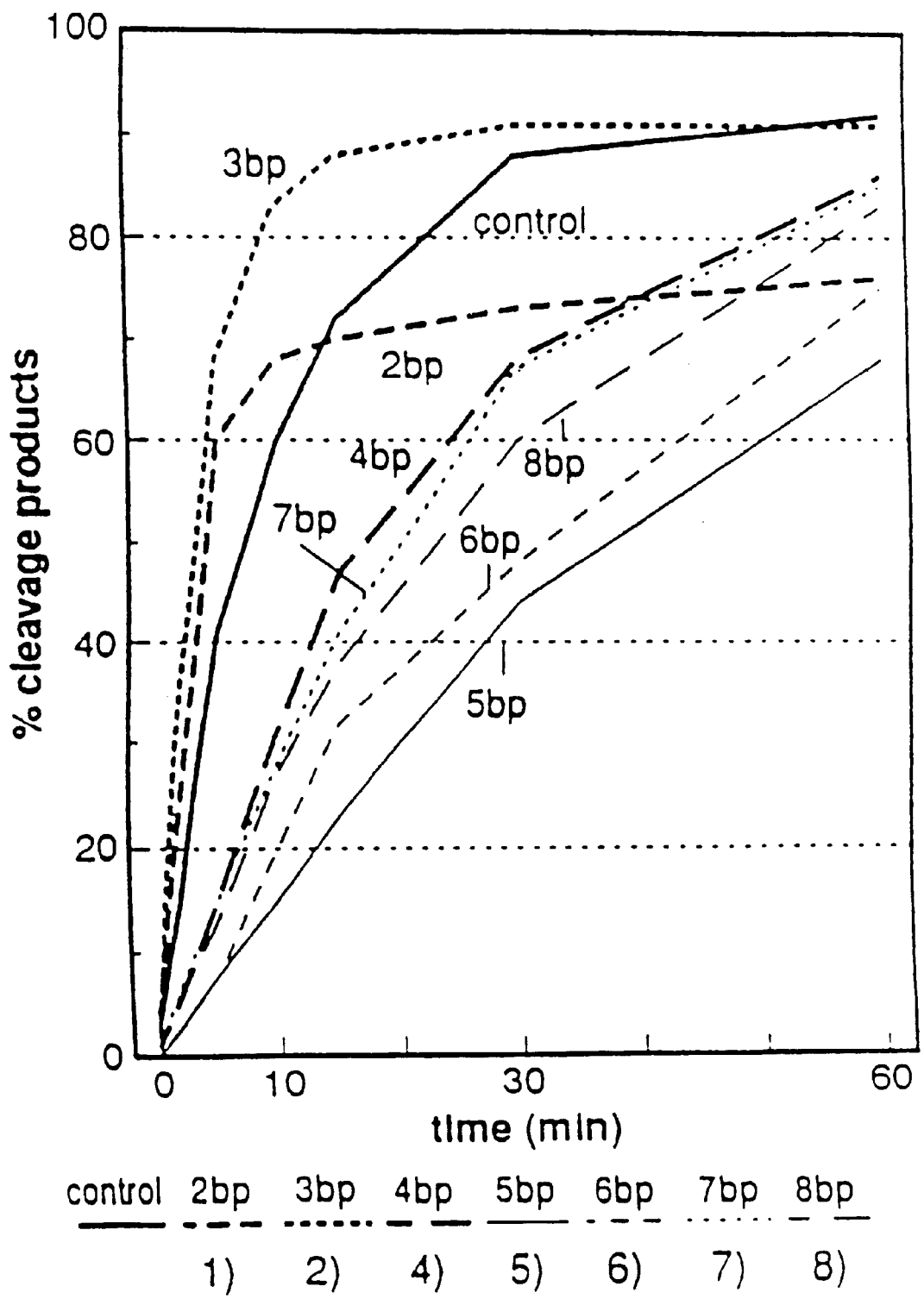
FIG. 1. Shows the cleavage efficiency of helix II $((X)_m$ and $(X)_{m'}$ of formulas 1 and 2) stem-length variants by plotting % cleavage as a function time in minutes. The data plotted is tabulated in Table 1 and each entry in Table 1 corresponds to each graph in the plot by number.

In several embodiments there is provided compounds that are capable of cleaving a RNA target molecule. These compounds are represented below as formulas 1, 2, 3 and 4. Generally these compounds are known as ribozymes. More specifically, compounds of formula 1, 2, and 3 are known as ribozymes; and compounds of formula 4 are known as tRNA embedded ribozymes.

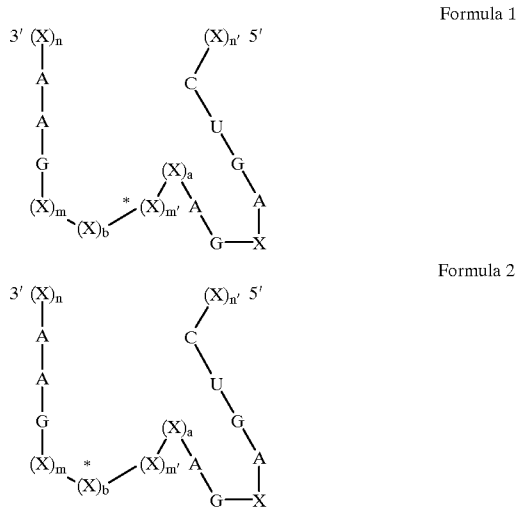

Formula 1

Formula 2

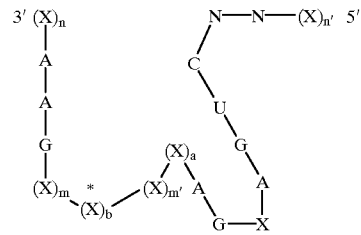

Formula 3

$3'-(X)_t—Y—(X)_{t'}-5'$

Formula 4

In the compounds of formulas 1, 2, and 3: The symbol X represents a nucleotide which may be the same or different and may be substituted or modified in its sugar, base or phosphate. The solid lines drawn in formulas 1, 2 and 3 represent a chemical linkage providing covalent bonds between the nucleotides located on either side thereof. The integer a defines the number of nucleotides in $(X)_a$ such that a may be 0 or 1 and if 0, the A located 5' of $(X)_a$ is bonded to the X located 3' of $(X)_a$.

In the above compounds of formulas 1 and 2: The symbols $(X)_n$ and $(X)_{n'}$ represent an oligonucleotide having a predetermined sequence which is capable of hybridizing with an RNA target sequence to be cleaved. The oligonucleotides, $(X)_n$ and $(X)_{n'}$, do not naturally occur covalently bound to the sequences 3'-A-A-G-5' and 5'C-U-G-A-3', respectively, and such RNA target sequences are not present within formula 1 or formula 2. The symbols n and n' represent integers which define the number of nucleotides in the oligonucleotides $(X)_n$ and $(X)_{n'}$ respectively, and the sum of n+n' is greater than 14.

In the compounds of formulas 1 and 3: The oligonucleotide $(X)_b$ may be present or absent, and b represents an integer which is greater than or equal to four if $(X)_b$ is present. In the compounds of formulas 2 and 3: The symbol * represents base pairing between the nucleotides located on either side thereof. In the above compounds of formula 1: The oligonucleotides, $(X)_m$ and $(X)_{m'}$, represent an oligonucleotide having the sequences (a) 3'-CUG-5' and 5'-GAC-3', (b) 3'-GCG-5' and 5'-AGC-3', (c) 3'-CGG-5' and 5'-GCC-3' or (d) 3'-CGC-5' and 5'-GCG-3', respectively and each * represents base pairing between the nucleotides located on either side thereof.

In the above compounds of formula 2: The integers m and m' range from two to eight inclusive. The oligonucleotide $(X)b$ has one of the following sequences: 3'-AGGUU-5', 3'-AGGG-5', 3'-AAGGC-5' or 3'-GGUG-5'.

In the above compounds of formula 3: The symbol $(X)_n$ represents an oligonucleotide having a predetermined sequence which is capable of hybridizing with an RNA target sequence to be cleaved. The oligonucleotides, $(X)_n$ and $(X)_{n'}$, do not naturally occur covalently bound to the sequences 3'-A-A-G-5' and 5'-C-U-G-A-3', respectively, and such RNA target sequences are not present within formula 3. The segment —N—N— are nucleotides that have a predetermined sequence to the RNA target sequence. The symbols n and n' represent integers which define the number of nucleotides in the oligonucleotides $(X)_n$ and $(X)_{n'}$ respectively, and the sum of n+n' is greater than 12. The integers m and m' are greater than or equal to 4.

In the above compounds of formula 4: The symbol X represents a nucleotide which may be the same or different. The oligonucleotides, $(X)_t$ and $(X)_{t'}$, have a sequence from a portion of a tRNA molecule. The integers, t and t', define the number of nucleotides in the oligonucleotide with the proviso that the sum of t+t' is greater than 50. The symbol Y represents a synthetic non-naturally occurring oligonucleotide compound which compound comprises nucleotides whose sequence defines a conserved catalytic region and nucleotides whose sequence is capable of hybridizing with a predetermined target sequence to be cleaved.

In another embodiment, the oligonucleotides, $(X)_t$ and $(X)_{t'}$ of formula 4, are derived from a tyrosine tRNA molecule of *Nicotiana rustica*.

In several embodiments, each of m and m' of formulas 2 or 3 are four.

In several embodiments, the nucleotide $(X)_b$ of formula 1 or 3 is present. In several embodiments, if $(X)_b$ of formula 1 or 3 is present, then the integer b of $(X)_b$ is equal to four. In several embodiments, the oligonucleotide $(X)_b$ of formula 1 or 3 has the sequence 5'-G-U-G-A-3'. In several embodiments, the oligonucleotide 3'-$(X)_n$- of formula 1, 2 or 3 is 3'-$(X)_{n-1}$-A-. In several embodiments, the oligonucleotide 3'-$(X)_{n'}$- of formula 1, 2 or 3 is 3'-$(X)_{n-2}$-C-A-. In several embodiments, the nucleotide $(X)_a$ of formula 1, 2 or 3 is absent. The oligonucleotides $(X)_n$, $(X)_{n'}$, N—N—$(X)_{n'}$ (of formula 1, 2, 3, or 4) represents the arms or flanking sequences of a ribozyme which hybridize to respective portions of a target RNA sequence. The arms may hybridize along the full length of the target RNA or part thereof. The sequence 3'- . . . AAG-$(X)_m$—$(X)_b$—$(X)_{m'}$—$(X)_n$-AGXAGUC- . . . -5' of formulas 1–3 represents the catalytic region. The catalytic region may also form part of the hybridizing region. The catalytic region may contain one or more additional nucleotides which do not adversely effect catalytic activity. Such additions could be readily tested for ribozyme activity without undue experimentation.

In another embodiment, there is provided a composition which comprises a compound of any of formulas 1, 2, or 3 in association with an acceptable carrier. In several embodiments, there is provided a oligonucleotide transfer vector containing a nucleotide sequence which on transcription gives rise to a compound of formula 1, 2, 3, or 4.

In several embodiments, there is provided a transfer vector, as mentioned hereinabove, that may be a bacterial plasmid, a bacteriophage DNA, a cosmid, or an eukaryotic viral DNA. In one embodiment, there is provided a transfer vector that may be a bacterial plasmid, a bacteriophage DNA, a cosmid, or plant viral DNA. In one embodiment, there is provided a transfer vector, as mentioned hereinabove, that contains the promoter sequences for RNA polymerase II or RNA polymerase III. In several embodiments, there is provided a host cell transformed by the transfer vector as mentioned hereinabove. In several embodiments, there is provided a host cell, as mentioned hereinabove, which may be a prokaryotic host cell or an eukaryotic host cell. In several embodiments, the prokaryotic host cell, as mentioned hereinabove, is an *E. coli* host cell. In several embodiments, the eukaryotic host cell, as mentioned hereinabove, is a monkey COS host cell, a Chinese hamster ovary host cell, a mammalian host cell or a plant host cell. In one embodiments, the eukaryotic host cell, as mentioned hereinabove, is a monkey COS host cell, a Chinese hamster ovary host cell, a mammalian host cell, a plant host cell or a plant protoplast host cell.

In one embodiment, there is provided a packaged oligonucleotide transfer vector, as mentioned hereinabove, that contains a nucleotide sequence which on transcription gives rise to the compound of formula 4. In one embodiment, there is provided a packaged oligonucleotide transfer vector, as mentioned hereinabove, which is a plant DNA virus, a geminivirus or an infective phage particle. In one embodiment, there is provided a packaged oligonucleotide transfer vector, as mentioned hereinabove, which contains the promoter sequences for RNA polymerase II or RNA polymerase III.

In accordance with another aspect of this invention, there is provided a composition for enhanced RNA cleavage comprising a first synthetic non-naturally occurring oligonucleotide compound which compound comprises nucleotides whose sequence defines a conserved catalytic region and nucleotides whose sequence is capable of hybridizing with a predetermined target sequence to be cleaved and a second synthetic non-naturally occurring oligonucleotide which does not contain the predetermined target sequence and is complementary to at least a portion of the compound. In another embodiment, the composition, as discussed hereinabove, is in association with an acceptable carrier. Additionally, the second synthetic non-naturally occurring oligonucleotide, as discussed hereinabove, may include, but are not limited to, one of the sequences listed in Table 8. Furthermore, the second synthetic non-naturally occurring oligonucleotide may be replaced with a solvent which may also enhance ribozymes (of the present invention) cleavage rates and may include, but are not limited to, one of the solvents listed in Table 8.

An aspect of this invention provides a composition as discussed hereinabove wherein the oligonucleotide is an oligoribonucleotide or an oligodeoxyribonucleotide which may be substituted or modified in its sugars, bases or phosphodiester linkages. Accordingly, oligonucleotide derivatives or modifications may be made at the level of the sugar, base, monophosphate groupings or phosphodiester linkages. It is preferred that the oligonucleotide be an oligoribonucleotide, however, other substitutions or modifications in the nucleotide are possible providing that endonuclease activity is not lost. Such derivatives or modifications are described hereinbelow.

In several embodiments, the synthetic non-naturally occurring oligonucleotide compound of (a) the composition and (b) of formula 4, discussed hereinabove, has the structure:

Formula 1a

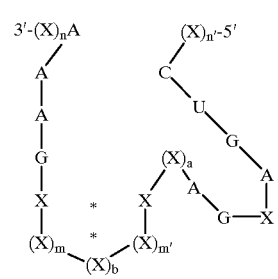

wherein each X represents a nucleotide which is the same or different and may be modified or substituted in its sugar, phosphate or base; wherein each of A, C, U, and G represents a ribonucleotide which may be unmodified or modified or substituted in its sugar, phosphate or base; wherein 3'—AAG . . . AGUCX—5' defines a conserved catalytic region; wherein each of $(X)_nA$ and $(X)_{n'}$ represents an oligonucleotide having a predetermined sequence which is capable of hybridizing with an RNA target sequence to be cleaved, and does not naturally occur covalently bound to the sequences 3'-A-A-G-5' and 5'-C-U-G-A-3', respectively, such RNA target sequence not being present within the compound; wherein each * represents base pairing between the nucleotides located on either side thereof; wherein each solid lie represents a chemical linkage providing covalent bonds between the nucleotides located on either side thereof; wherein a represents an integer which defines a number of nucleotides with the proviso that a may be 0 or 1 and if 0, the A located 5' of $(X)_a$ is bonded to the X located 3' of $(X)_a$; wherein each of m and m' represents an integer which is greater than or equal to 1; and wherein $(X)_b$ represents an oligonucleotide and b represents an integer which is greater than or equal to four.

In several embodiments, the synthetic non-naturally occurring oligonucleotide compound of (a) the composition and (b) of formula 4, discussed hereinabove, has the structure:

Formula 1b

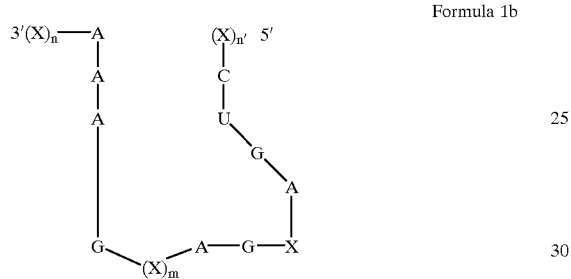

wherein each X is the same or different and represents a ribonucleotide or a deoxyribonucleotide which may be modified or substituted in its sugar, phosphate or base; wherein each of A, C, U, and G represents a ribonucleotide which may be unmodified or modified or substituted in its sugar, phosphate or base; wherein 3'—AAG . . . AGUCX—5' defines a conserved catalytic region; wherein each of $(X)_n A$ and $(X)_{n'}$ represents an oligonucleotide having a predetermined sequence which is capable of hybridizing with an RNA target sequence to be cleaved, and does not naturally occur covalently bound to the sequences 3'-A-A-G-5' and 5'-C-UG-A-3', respectively, such RNA target sequence not being present within the compound; wherein each solid line represents a chemical linkage providing covalent bonds between the nucleotides located on either side thereof; wherein m represents an integer from 2 to 20; and wherein none of the nucleotides $(X)_m$ are Watson-Crick base paired to any other nucleotide within the compound.

In several embodiments, the synthetic non-naturally occurring oligonucleotide compound of (a) the composition and (b) of formula 4, discussed hereinabove, has the structure:

Formula 1c

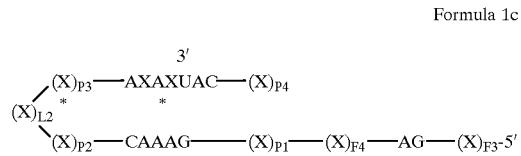

wherein each X is the same or different and represents a ribonucleotide or a deoxyribonucleotide which may be modified or substituted in its sugar, phosphate or base; wherein each of A, C, U, and G represents a ribonucleotide which may be unmodified or modified or substituted in its sugar, phosphate or base; wherein $3'(X)_{P4} \ldots (X)_{P1}$—5' defines a conserved catalytic region; wherein each of $(X)_{F4}$, and $(X)_{F3}$ represents an oligonucleotide having a predetermined sequence which is capable of hybridizing with an RNA target sequence to be cleaved; wherein each solid line is represents a chemical linkage providing covalent bonds between the nucleotides located on either side thereof; wherein F3 represents an integer which defines the number of nucleotides in the oligonucleotide with the proviso that F3 is greater than or equal to 3; wherein F4 represents an integer which defines the number of nucleotides in the oligonucleotide with the proviso that F4 is from 3 to 5; wherein each of $(X)_{P1}$ and $(X)_{P4}$ represents an oligonucleotide having a predetermined sequence such that $(X)_{P4}$ base-pairs with 3–6 bases of $(X)_{P1}$; wherein P1 represents an integer which defines the number of nucleotides in the oligonucleotide with the proviso that P1 is from 3 to 6 and the sum of P1 and F4 equals 9; wherein each of $(X)_{P2}$ and $(X)_{P3}$ represents an oligonucleotide having a predetermined sequence such that $(X)_{P2}$ base-pairs with at least 3 bases of $(X)_{P3}$; wherein each * represents base pairing between the nucleotides located on either side thereof; wherein each solid line represents a chemical linkage providing covalent bonds between the nucleotides located on either side thereof; wherein each of the dashed lines independently represents either a chemical linkage providing covalent bonds between the nucleotides located on either side thereof or the absence of any such chemical linkage; and wherein $(X)_{L2}$ represents an oligonucleotide which may be present or absent with the proviso that L2 represents an integer which is greater than or equal to 3 if $(X)_{L2}$ is present.

In formulas 1, 2, 3, 1a, and 1b, the integers n and n' that define the number of nucleotides in $(X)_n$ and $(X)_{n'}$, respectively, may range from five to two hundred, and preferably may range from six to twenty. In formulas 1, 2, 3, and 1a, the integers m and m' that define the number of nucleotides in $(X)_m$ and $(X)_{m'}$, respectively, may range from four to twenty, and preferably may range from four to five. In formulas 1, 2, 3, and 1a, the integer b that defines the number of nucleotides in $(X)_b$ may range from one to eight, but preferably may range from one to four. In formula 1b, the integer m that define the number of nucleotides in $(X)_m$ may range from two to thirty, and preferably may range from four to ten. In formula 1c, the integer P1 that defines the number of nucleotides in $(X)_{P1}$ may range from three to ten, but preferably may range from three to six. In formula 1c, the integers P2 and P3 that define the number of nucleotides in $(X)_{P2}$ and $(X)_{P3}$, respectively, may range from three to twenty, and preferably may range from three to ten. In formula 1c, the integer P4 that defines the number of nucleotides in $(X)_{P4}$ may range from three to ten, but preferably may range from three to six. In formula 1c, the integer L2 that defines the number of nucleotides in $(X)_{L2}$ may range, if $(X)_{L2}$ present, from three to twenty, but preferably may range from three to ten. In formula 1c, the integer F3 that defines the number of nucleotides in $(X)_{F3}$ may range from three to twenty, but preferably may range from three to ten. In formula 1c, the integer F4 that defines the number of nucleotides in $(X)_{F4}$ may range from three to twenty, but preferably may range from three to five. Additionally, each of $(X)_m$ and $(X)_{m'}$ of formulas 1, 2, 3, or 1a may be, but is not limited to, an oligonucleotide having one of the sequences listed in Table 1, Table 2, and Table 4. Additionally, the oligonucleotide $(X)_b$ of formulas 1, 2, 3, or 1a may include, but are not limited to, one of the sequences listed in Table 3. Additionally, each of $(X)_n$ and $(X)_{n'}$ of formulas 1, 2, 3, 1a, or 1b may include, but are not limited to, one of the sequences listed in Tables 6 and Table 7 wherein $(X)_n$ and $(X)_{n'}$ in the tables are helix III and helix I respectively.

The sequence $(X)_m—(X)_b—(X)_m$ as represented in formulas 1, 2, 3 or 1a, may be short in length and may be absent of base pairing between $(X)_m$ and $(X)_{m'}$. For convenience, these types of ribozymes are called minizymes. The sequences $(X)_m—(X)_b—(X)_{m'}$ of formulas 1–4 may include, but are not limited to, one of the sequences listed as minizyme variants in Table 5.

Endonuclease activity of the ribozyme (of formula 1, 2, 3, or 4) is readily, simply and routinely tested by incubating the ribozyme with its substrate and thereafter assessing whether cleavage of a the substrate takes place. For example, cleavage of a target mRNA takes place after the trinucleotide sequence XUX' where X and X' represent any ribonucleotide, and which may be the same or different and U represents a ribonucleotide having the base uridine. Preferred cleavage sites, XUX', include GUC, GUU, GUA and UUC. By way of example, suitable reaction conditions may comprise a temperature from about 4 degree(s) C. to about 60 degree(s) C. (preferably about 20 degree(s) to 55 degree(s) C.), pH from about 7.0 to about 9.0 and salt (such as $Mg^{2+}$) from about 1 to about 100 mM (preferably 1 to 20 mM). Ribozymes containing a small number of nucleotides in each of the groups $(X)_n$ and $(X)_{n'}$ of formulas 1–3 (such as four nucleotides) would generally be incubated at lower temperatures, such as about 20 degree(s) C. to about 25 degree(s) C. to aid duplexing of complementary nucleotide sequences in the ribozyme sequences $(X)_n$ and $(X)_{n'}$ and the substrate. The ribozyme would generally be in an equimolar ratio to the substrate or in excess thereof. However, as the ribozyme may act as an enzyme, cleaving substrate without consumption, the ratio of ribozyme to substrate is not of importance.

A target RNA containing a suitable cleavage site such as GUC site may be incubated with a ribozyme (of formula 1, 2, 3, or 4) or a composition (as described hereinabove) wherein one of the components is a ribozyme (which may be a compound of formula 1, 2, 3, 4, 1a, 1b, or 1c) which, for example, may contain one or more modifications within the catalytic region of the ribozyme. The nucleotide sequences $(X)_n$ and $(X)_{n'}$ of formulas 1–2 are selected so as to be complementary (that is, capable of forming base pairs) to nucleotide sequences flanking the cleavage site in the target RNA. The nucleotide sequences $(X)_n$ of formula 3 are selected so as to be complementary (that is, capable of forming base pairs) to nucleotide sequences flanking the cleavage site in the target RNA, whereas the nucleotide sequences —N—N— $(X)_{n'}$ of formula 3 are selected so as to be complementary (that is, capable of forming base pairs) to part of nucleotide sequences flanking the cleavage site in the target RNA. On incubation of the ribozyme or ribozyme composition and its substrate, an enzyme/substrate complex is formed as a result of base pairing between complementary nucleotides in the ribozyme and the substrate. Nucleotide sequences $(X)_n$ and $(X)_{n'}$ of the formulas 1–3 and nucleotide sequences flanking the cleavage site in the substrate may form a double stranded duplex as a result of base pairing, which base pairing is well known in the art [See for example: Sambrook, 1989]. The formation of a double stranded duplex between complementary nucleotides may be referred to as hybridization [Sambrook, 1989]. Hybridization or duplex formation between the ribozyme and its substrate can be readily assessed, for example, by labelling one or both components, such as with a radiolabel, and then subjecting the reaction mixture to polyacrylamide gel electrophoresis under non-denaturing conditions [Sambrook, 1989]. If the target is cleaved on incubation with the ribozyme it is active and is within the scope of this invention. Accordingly, a ribozyme containing a nucleotide derivative may be simply tested for endonuclease activity in a routine manner.

As will be readily appreciated by workers in the field to which this invention relates, the cleavage of a target RNA may be readily assessed by various methods well known in the art [See for example: Sambrook, 1989]. Cleavage may, for example, be assessed by running the reaction products (where the substrate is radioactively labelled) on acrylamide, agarose, or other gel systems, and then subjecting the gel to autoradiography or other analytical technique to detect cleavage fragments [Sambrook, 1989].

The nucleotides of the sequences $(X)_n$ and $(X)_{n'}$ of formulas 1–4 may be of any length and sequence sufficient to enable hybridization formation with complementary nucleotides in the target RNA, as described herein. The nucleotides may be in the form of deoxyribonucleotides, ribonucleotides, deoxyribonucleotide ribonucleotide hybrids, or derivatives thereof as herein described. These flanking sequences $((X)_n$ and $(X)_{n'}$ of formulas 1–4) may be chosen to optimize stability of the ribozyme from degradation. For example, deoxyribonucleotides are resistant to the action of ribonucleases. Modified bases, sugars or phosphate linkages of nucleotides, such as phosphoramidate, or phosphorothioate linkages in the phosphate backbone of the nucleotide sequences, may also provide resistance to nuclease attack. Binding affinity may also be optimized in particular circumstances, by providing nucleotides solely in the form of ribonucleotides, deoxyribonucleotides, or combinations thereof. In some circumstances it may be necessary to optimize the composition of the sequences $(X)_n$ and $(X)_{n'}$ of formulas 1–4, to maximize target RNA cleavage. The cleavage activity of ribozymes having flanking nucleotide sequences which hybridize to target sequences and which are comprised wholly of deoxyribonucleotides may, in some circumstances, have reduced activity. In such circumstances optimization may involve providing a mixture of deoxyribonucleotides and ribonucleotides in the nucleotide sequences $(X)_n$ and $(X)_{n'}$ of formulas 1–4. For example, nucleotides in the ribozyme which are proximal to the cleavage site in a target RNA may be in the form of ribonucleotides.

The respective 3' and 5' termini of the sequences $X_n$ and $(X)_{n'}$ (of formula 1, 2, 3, 4, 1a, 1b, or 1c) or alternatively the 3' and 5' end termini of the ribozyme, may be modified to stabilize the ribozyme from degradation. For example, blocking groups may be added to prevent terminal nuclease attack, in particular 3'–5' progressive exonuclease activity. By way of example, blocking groups may be selected from optionally substituted alkyl, optionally substituted phenyl, optionally substituted alkanoyl. Optional substituents may be selected from $C_1$–$C_5$ alkyl; halogen such as F, Cl or Br; hydroxy; amino; $C_1$–$C_5$ alkoxy and the like. Alternatively, nucleotide analogues such as phosphothioates, methylphosphonates or phosphoramidates or nucleoside derivatives (such as alpha-anomers of the ribose moiety) which are resistant to nuclease attack may be employed as terminal blocking groups.

Alternatively, groups which alter the susceptibility of the ribozyme molecule to other nucleases may be inserted into the 3' and/or 5' end of the ribozyme (of formula 1, 2, 3, 4, 1a, 1b, or 1c). For example, 9-amino-acridine attached to the ribozyme may act as a terminal blocking group to generate resistance to nuclease attack on the ribozyme molecules and/or as an intercalating agent to aid endonucleolytic activity. It will be readily appreciated that a variety of other chemical groups, e.g. spermine or spermidine could be used in a related manner.

It is also possible to stabilize the ribozyme (of formula 1, 2, 3, 4, 1a, 1b, or 1c) from degradation by embedding it in a RNA molecule, for example, as described hereinabove in formula 4. Such RNA molecules embedded with a ribozyme molecule may include, but are not limited to, tRNA, mRNA, rRNA or other RNA molecules. Further, it is possible to insert the ribozyme in a DNA molecule as well.

Ribozymes of this invention (of formula 1, 2, 3, 4, 1a, 1b, or 1c) may be covalently or non-covalently associated with affinity agents such as proteins, steroids, hormones, lipids, nucleic acid sequences, intercalating molecules (such as acridine derivatives, for example 9-amino acridine) or the like to modify binding affinity for a substrate nucleotide sequence or increase affinity for target cells, or localization in cellular compartments or the like. For example, the ribozymes of the present invention may be associated with RNA binding peptides or proteins which may assist in bringing the ribozyme into juxtaposition with a target nucleic acid such that hybridization and cleavage of the target sequence may take place. Nucleotide sequences may be added to the respective 3' and 5' termini of the sequences $(X)_n$ and $(X)_{n'}$ of formulas 1–4 or alternatively the 3' and 5' end termini of the ribozyme to increase affinity for substrates. Such additional nucleotide sequences may form triple helices with target sequences [Strobel, 1991] which may enable interaction with intramolecularly folded substrate. Alternatively, modified bases (non-natural or modified bases as described in Principles of Nucleic Acid Structure [Sangar, 1984]) within the additional nucleotide sequences may be used that will associate with either single stranded or duplex DNA generating base pair, triplet, or quadruplet, interactions with nucleotides in the substrate. Suitable bases would include inosine, 5'-methylcytosine, 5'-bromouracil and other such bases as are well known in the art, as described, for example, in Principles of Nucleic Acid Structure [Sangar, 1984].

The ribozymes of this invention (of formula 1, 2, 3, 4, 1a, 1b, or 1c) may be produced by nucleotide synthetic techniques which are well known in the art, and described for example by Carruthers et al., Foehler et al. and Sprat et al. [Carruthers, 1987; Foehler, 1986; Sprat, 1984]. Generally, such synthetic procedures involve the sequential coupling of activated and protected nucleotide bases to give a protected nucleotide chain, whereafter protecting groups may be removed by suitable treatment. Alternatively, the ribozymes in accordance with this invention may be produced by transcription of nucleotide sequences encoding said ribozymes in host-cells or in cell free systems utilizing enzymes such as T3, SP6 or T7 RNA-polymerase. Further means for producing the ribozymes of this invention are further discussed hereinbelow [Sambrook, 1989].

Nucleotides represented in formulas 1, 2, 3, 4, 1a, 1b, and 1c comprise a sugar, base, and a monophosphate group or a phosphodiester linkages. Accordingly, nucleotide derivatives or modifications may be made at the level of the sugar, base, monophosphate groupings or phosphodiester linkages. It is preferred that the nucleotides in formulas 1–4 be ribonucleotides, however, other substitutions or modifications in the nucleotide are possible providing that endonuclease activity is not lost. More specifically, it is preferred that the catalytic region be comprised of ribonucleotides. In one aspect of this invention, the sugar of the nucleotide may be a ribose or a deoxyribose such that the nucleotide is either a ribonucleotide or a deoxyribonucleotide, respectively. Furthermore, the sugar moiety of the nucleotide may be modified according to well known methods in the art [See for example: Sangar, 1984; Sober, 1970]. This invention embraces various modifications to the sugar moiety of nucleotides as long as such modifications do not abolish cleavage activity of the ribozyme. Examples of modified sugars include replacement of secondary hydroxyl groups with halogen, amino or azido groups; 2'-methylation; conformational variants such as the O2'-hydroxyl being cis-oriented to the glycosyl $C_1'$—N link to provide arabinonucleosides, and conformational isomers at carbon $C_1'$ to give alpha-nucleosides, and the like.

Accordingly, the base of the nucleotide may be adenine, guanine, cytosine, methyl cytosine, uracil, thymine xanthine, hypoxanthine, inosine, or other methylated bases. Nucleotide bases, deoxynucleotide bases, and ribonucleotide bases are well known in the art and are described, for example in Principles of Nucleic Acid Structure [Sangar, 1984]. Furthermore, nucleotide, ribonucleotide, and deoxyribonucleotide derivatives, substitutions and/or modifications are well known in the art [See for example: Sangar, 1984; Sober, 1970], and may be made with the proviso that endonuclease activity of the ribozyme is not lost. As mentioned previously, endoribonuclease activity may be readily and routinely assessed.

In addition, a large number of modified bases are found in nature, and a wide range of modified bases have been synthetically produced [See for example: Sangar, 1984; Sober, 1970]. For example, amino groups and ring nitrogens may be alkylated, such as alkylation of ring nitrogen atoms or carbon atoms such as $N_1$ and $N_7$ of guanine and $C_5$ of cytosine; substitution of keto by thioketo groups; saturation of carbon double bond carbon double bonds, and introduction of a C-glycosyl link in pseudouridine. Examples of thicketo derivatives are 6-mercaptopurine and 6-mercaptoguanine. Bases may be substituted with various groups, such as halogen, hydroxy, amine, alkyl, azido, nitro, phenyl and the like. The phosphate moiety of nucleosides or the phosphodiester linkages of oligonucleotides are also subject to derivatization or modifications, which are well known in the art. For example, replacement of oxygen with nitrogen, sulphur or carbon derivatives to respectively give phosphoramidates, phosphorothioates and phosphonates. Substitutions of oxygen with nitrogen, sulphur or carbon derivatives may be made in bridging or non bridging positions. It has been well established from work involving antisense oligonucleotides [Uhlmann, 1990] that phosphodiester and phosphorothioate derivatives may efficiently enter cells (particularly when of short length), possibly due to association with a cellular receptor. Methylphosphonates are probably readily taken up by cells by virtue of their electrical neutrality.

A further aspect of the invention provides alternative linkages such as an amide, a sufonamide, a hydroxylamine, a thioformal, a formacetal, a 3'-thioformacetal, a sulfide, or an ethylene glycol function to replace the conventional phosphodiester linkage. These modifications may increase resistance towards cellular nucleases and/or improved pharmacokinetics.

Any combination of the above listed nucleotide modifications, substitutions, or derivatizations, made at the level of the sugar, base, or monophosphate groupings or phosphodiester linkages may be made providing that endonuclease activity of the ribozymes (of formula 1, 2, 3, 4, 1a, 1b, or 1c) included in this invention are not lost.

As hereinabove discussed in formulas 1, 2, 3, 4, 1a, 1b, or 1c, base pairing between nucleotides are depicted through the use of the symbol "*". Base pairing may be Watson-Crick base pairing or Non-Watson-Crick base pairing. In some instances, an admixture of Watson-Crick and Non-Watson-Crick base pairing yields ribozymes with increased catalytic activity.

Ribozymes of this invention (formulas 1, 2, 3, 4, 1a, 1b, or 1c) may be incorporated and expressed in cells as a part of a DNA or RNA transfer vector, or a combination thereof, for the maintenance, replication and transcription of the ribozyme sequences of this invention. Nucleotide sequences encoding the ribozymes of this invention (formulas 1, 2, 3, 4, 1a, 1b, or 1c) may be integrated into the genome of a eukaryotic or prokaryotic host cell for subsequent expression (for example as described [Sambrook, 1989]. Genomic integration may be facilitated by transfer vectors which integrate into the host genome. Such vectors may include nucleotide sequences, for example of viral or regulatory origin, which facilitate genomic integration. Methods for the insertion of nucleotide sequences into a host genome are described for example in Sambrook et al. and Hogan et al. [Sambrook, 1989; Hogan, 1986; 1989].

Genomically integrated nucleic acid sequences encoding the ribozymes of this invention (formulas 1, 2, 3, 4, 1a, 1b, or 1c) generally comprise a promoter operably linked to the nucleotide sequence encoding the ribozyme of this invention, and capable of expressing said ribozyme in a eukaryotic (such as animal or plant cells) or prokaryotic (such as bacteria) host cells. Additionally, the ribozymes of the present invention (formulas 1, 2, 3, 4, 1a, 1b, or 1c) may be prepared by methods known per se in the art for the synthesis of RNA molecules. (For example, according to recommended protocols of Promega, Madison, Wis., USA). In particular, the ribozymes of the invention may be prepared from a corresponding DNA sequence (DNA which on transcription yields a ribozyme, and which may be synthesized according to methods known per se in the art for the synthesis of DNA) operably linked to an RNA polymerase promoter such as a promoter for T7 RNA polymerase or SP6 RNA polymerase. A DNA sequence corresponding to a ribozyme of the present invention may be ligated into a DNA transfer vector, such as plasmid or bacteriophage DNA. Where the transfer vector contains an RNA polymerase promoter operably linked to DNA corresponding to a ribozyme, the ribozyme may be conveniently produced upon incubation with an RNA polymerase. Ribozymes may, therefore, be produced in vitro by incubation of RNA polymerase with an RNA polymerase promoter operably linked to DNA corresponding to a ribozyme, in the presence of ribonucleotides. In vivo, prokaryotic or eukaryotic cells (including mammalian and plant cells) may be transfected with an appropriate transfer vector containing genetic material corresponding to a ribozyme in accordance with the present invention, operably linked to an RNA polymerase polymer such that the ribozyme is transcribed in the host cell. Transfer vectors may be bacterial plasmids or viral RNA or DNA. Nucleotide sequences corresponding to ribozymes are generally placed under the control of strong promoters such as, for example, the lac, SV40 late, SV40 early, metallothionein, or lambda promoters. Ribozymes may be directly transcribed in-vivo from a transfer vector, or alternatively, may be transcribed as part of a larger RNA molecule. For example, DNA corresponding to ribozyme sequences may be ligated into the 3' end of a carrier gene, for example, after a translation stop signal. Larger RNA molecules may help to stabilize the ribozyme molecules against nuclease digestion within cells. On translation the carrier gene may give rise to a protein, whose presence can be directly assayed, for example, by enzymatic reaction. The carrier gene may, for example, encode an enzyme.

Ribozymes of this invention (formulas 1, 2, 3, 4, 1a, 1b, or 1c) may be involved in gene therapy techniques, where, for example, cells from a human suffering from a disease, such as HIV are removed from a patient, treated with the ribozyme to inactivate the infectious agent, and then returned to the patient to repopulate a target site with resistant cells. In the case of HIV, nucleotide sequences encoding ribozymes of this invention capable of inactivating the HIV virus may be integrated into the genome of lymphocytes or be present in the cells a transfer vector capable of expressing ribozymes of this invention. Such cells would be resistant to IV infection and the progeny thereof would also confer such resistance.

Ribozymes of this invention (formulas 1, 2, 3, 4, 1a, 1b, or 1c) may be incorporated and expressed in cells as a part of a DNA or RNA transfer vector, or a combination thereof, for the maintenance, replication and transcription of the ribozyme sequences of this invention. In-vivo, that is, within the cell or cells of an organism, a transfer vector such as a bacterial plasmid or viral RNA or DNA, encoding one or more ribozymes (formulas 1, 2, 3, 4, 1a, 1b, or 1c), may be transfected into cells [See for example: Llewellyn, 1987; Hanahan, 1983]. Once inside the cell, the transfer vector may replicate and be transcribed by cellular polymerases to produce ribozyme RNAs which may have ribozyme sequences of this invention; the ribozyme RNAs produced may then inactivate a desired target RNA. Alternatively, a transfer vector containing one or more ribozyme sequences may be transfected into cells or introduced into cells by way of micromanipulation techniques such as microinjection, such that the transfer vector or a part thereof becomes integrated into the genome of the host cell. Transcription of the integrated genetic material gives rise to ribozymes, which act to inactivate a desired target RNA.

Transfer vectors expressing ribozymes of this invention (formulas 1, 2, 3, 4, 1a, 1b, or 1c) may be capable of replication in a host cell for stable expression of ribozyme sequences. Alternatively, transfer vectors encoding ribozyme sequences of this invention may be incapable of replication in host cells, and thus may result in transient expression of ribozyme sequences. Methods for the production of DNA and RNA transfer vectors, such as plasmids and viral constructs are well known in the art and are described for example by Sambrook et al. [Sambrook, 1989]. Transfer vectors would generally comprise the nucleotide sequence encoding the ribozyme of this invention (formulas 1, 2, 3, 4, 1a, 1b, or 1c), operably linked to a promoter and other regulatory sequences required for expression and optionally replication in prokaryotic and/or eukaryotic cells. Suitable promoters and regulatory sequences for transfer vector maintenance and expression in plant, animal, bacterial, and other cell types are well known in the art and are described for example in Hogan [Hogan, 1986; 1989].

The ribozymes of the present invention (formulas 1, 2, 3, 4, 1a, 1b, or 1c) have extensive therapeutic and biological applications. For example, disease causing viruses in man and animals may be inactivated by administering to a subject infected with a virus, a ribozyme in accordance with the present invention (such as given in formulas 1, 2, 3, 4, 1a, 1b, or 1c) adapted to hybridize to and cleave RNA transcripts of the virus. Such ribozymes may be delivered by parenteral or other means of administration. Alternatively, a subject infected with a disease causing virus may be administered a non-virulent virus such as vaccinia or adenovirus which has been genetically engineered to contain DNA corresponding to a ribozyme operably linked to an RNA promoter, such that the ribozyme is transcribed in the cells of the host animal, transfected with the engineered virus, to effect cleavage and/or inactivation of the target RNA transcript of the disease causing virus.

The ribozymes of the present invention (formulas 1, 2, 3, 4, 1a, 1b, or 1c) have particular application to viral diseases caused for example, by the herpes simplex virus (HSV) or the AIDS virus (HIV). Further examples of human and animal disease which may be treated with the ribozymes of this invention include psoriasis, cervical preneoplasia, papilloma disease, bacterial and prokaryotic infection, viral infection and neoplastic conditions associated with the production of aberrant RNAs such as occurs in chronic myeloid leukemia. Diseases or infections which may be treated in plants with ribozymes of this invention include fungal infection, bacterial infections (such as Crown-Gall disease) and disease associated with plant viral infection.

The period of treatment would depend on the particular disease being treated and could be readily determined by a physician. Generally treatment would continue until the disease being treated was ameliorated. The ribozymes of the present invention (formulas 1, 2, 3, 4, 1a, 1b, or 1c) also have particular application to the inactivation of RNA transcripts in bacteria and other prokaryotic cells, plants and animals. In bacteria, RNA transcripts of, for example, bacteriophage, (which cause bacterial cell death) may be inactivated by transfecting a cell with a DNA transfer vector which is capable of producing a ribozyme in accordance with the present invention which inactivates the phage DNA. Alternatively, the ribozyme itself may be added to and taken up by the bacterial cell to effect cleavage of the phage RNA. Similarly, eukaryotic and prokaryotic cells in culture may, for example, be protected from infection or disease associated with mycoplasma infection, phage infection, fungal infection and the like.

RNA transcripts in plants may be inactivated using ribozymes (such as those of formulas 1, 2, 3, 4, 1a, 1b, or 1c) encoded by a transfer vector such as the Ti plasmid of *Agrobacterium tumefaciens*. When such vectors are transfected into a plant cell, the ribozymes are produced under the action of RNA polymerase and may effect cleavage of a specific target RNA sequence. Accordingly, plant viruses whose RNA sequence are known, or the RNA transcripts of plant genes, may be inactivated using ribozymes. Endogenous gene transcripts in plants, animals or other cell types may be inactivated using the ribozymes of the present invention (such as those of formulas 1, 2, 3, 4, 1a, 1b, or 1c). Accordingly, undesirable phenotypes or characteristics may be modulated. If may, for example, be possible using the ribozymes of the present invention to remove stones from fruit or treat hereditary diseases in humans which are caused by the production of a deleterious protein, or over production of a particular protein. Furthermore, for the in-vivo applications of the ribozymes of this invention in humans, animals, plants, and eukaryotic and prokaryotic cells, such as in phenotypic modification and the treatment of disease, it is necessary to introduce the ribozyme into cells whereafter, cleavage of target RNAs takes place. In vivo applications are highly suitable to the ribozyme of formula 4 as discussed in more detail hereinbelow.

Methods for the introduction of RNA and DNA sequences into cells, and the expression of the same in prokaryotic and eukaryotic cells are well known in the art for example as discussed by Cotten and Friedman [Cotten, 1990; Friedman, 1989]. The same widely known methods may be utilized in the present invention.

The ribozymes of this invention (formulas 1, 2, 3, 4, 1a, 1b, or 1c) may be incorporated into cells by direct cellular uptake, where the ribozymes of this invention would cross the cell membrane or cell wall from the extracellular environment. Agents may be employed to enhance cellular uptake, such as liposomes or lipophilic vehicle, cell permeability agents, such as dimethylsulfoxide, and the like. Ribozymes of the present invention (formulas 1, 2, 3, 4, 1a, 1b, or 1c) may be combined with pharmaceutically and veterinarally acceptable carriers and excipients which are well known in the art, and include carriers such as water, saline, dextrose and various sugar solutions, fatty acids, liposomes, oils, skin penetrating agents, gel forming agents and the like, as described for example in Remington's Pharmaceutical Sciences, 17th Edition, Mack Publishing Co., Easton, Pa., Edited by Ostol et al., which is incorporated herein by reference.

Agriculturally acceptable carriers and excipients are well known in the art and include water; surfactants; detergents; particularly biodegradable detergents; talc; inorganic and/or organic nutrient solutions; mineral earths and clays; calcium carbonate; gypsum; calcium sulfate; fertilizers such as ammonium sulfate, ammonium phosphate and urea; and natural products of vegetable origin such as, for example, grain, meals and flours, bark meals; and the like. The ribozymes of this invention (formulas 1, 2, 3, 4, 1a, 1b, or 1c) may be provided in a composition with one or more anti-viral, anti-fungal, anti-bacterial, anti-parasitic, anti-protazoan or anthelmintic agents, herbicides, pesticides or the like, for example as described in the Merck Index (1989) 11th Edition, Merck & Co. Inc.

By way of example only, therapeutic compositions of this invention may be directed against Herpes Simplex virus types 1 and 2, psoriasis, cervical preneoplasia, papilloma disease, and bacterial and prokaryotic infection. Such treatments may, for example, involve topical application of ribozyme to the site of disease. For example, in the treatment of Herpes virus lesions, ribozymes may be formulated into a cream containing a concentration of 1 nM to 1 mM ribozyme. The cream may then be applied to the site of infection over a 1 to 14 day period in order to cause amelioration of symptoms of the infection. Prior to the final development of topical formulations for the treatment of Herpes virus infection, effectiveness and toxicity of the ribozymes and formulations involving them may, for example, be tested on an animal model, such as scarified mouse ear, to which virus particles, such as $2 \times 10^6$ plaque forming units are added. A titre of infectious virus particles in the ear after treatment can then be determined to investigate effectiveness of treatment, amount of nuclease required and like considerations. Similar investigations in animal models prior to human trials may also be conducted, for example, in respect of the treatment of psoriasis, papilloma disease, cervical preneoplasia, and in diseases such as HIV infection, bacterial or prokaryotic infection, viral infection and various neoplastic conditions, which neoplastic conditions involve a deleterious RNA species.

Compositions for topical application are generally in the form of creams, where the ribozymes of this invention may be mixed with viscous components. The ribozymes of this invention (formulas 1, 2, 3, 4, 1a, 1b, or 1c) may be incorporated into liposomes or other barrier type preparations to shield the ribozymes from nuclease attack or other degradative agents (such as ribozymes and adverse environmental conditions such as UV light). Compositions may be provided as unit dosages, such as capsules (for example gelatin capsules), tablets, suppositories and the like. Injectable compositions may be in the form of sterile solutions of ribozyme in saline, dextrose or other media. Compositions for oral administration may be in the form of suspensions, solutions, syrups, capsules, tablets and the like. Ribozymes may also be provided in the form of sustained release articles, impregnated bandages, patches and the like. Pharmaceutical compositions which may be used in this invention are described, for example, in Remington's Pharmaceutical Sciences.

The present invention is further directed to a DNA cassette for a plant, said cassette comprising a genetic sequence and a promoter capable of directing expression of said genetic sequences wherein said genetic sequence on expression provides anti-sense or ribozyme RNA to (−) RNA or a portion thereof associated with a viroid. The DNA cassette may further be part of a DNA transfer vector suitable for transferring the DNA cassette into a plant cell and insertion into a plant genome. In a most preferred embodiment of the present invention, the DNA cassette is carried by broad host range plasmid pGA470 and which is capable of transformation into plant cells using Agrobacterium. The present invention, however, extends to other means of transfer such as genetic bullets (e.g. DNA-coated tungsten particles, high-velocity micro projectile bombardment) and electroporation amongst others (Maliga, 1993; Bryant, 1992; or Shimamoto, 1989).

The transgenic plant resistant to a virus characterized in that it contains in its genome a sequence which gives rise, on transcription, to the nucleic acid molecule mentioned above. This transgenic plant, including fruits, and seeds thereof, may be from alfalfa, apple, bean, canola (oilseed rape), cantaloupe, corn, cotton, courgette, cucumber, melon, papaya, pepper, potato, rice, soybean, squash, strawberry, sunflower, sweet pepper, tobacco, tomato, or walnut. Also included are the plant cells transformed by the above-mentioned transfer vector, as well as a prokaryotic or eukaryotic cell, plant or animal, comprising a nucleotide sequence which is, or on transcription gives rise to, nucleic acid molecule.

The present invention will now be illustrated by way of non-limiting Examples only, with reference to the following non-limiting Examples, and Figures.

Throughout EXAMPLES 1–3, various Tables (1–8) are referenced by number. These tables are hereby incorporated by number into the present application. Tables 1–8 can be found immediately preceding the references.

In EXAMPLES 1–3 below: The ribozyme variants were examined for cleavage efficiency relative to the control sequence from satellite of tobacco ringspot virus (satTobRSV). The ribozymes were generated as in vitro T7 RNA polymerase transcripts and purified by denaturing polyacrylamide gel electrophoresis. The standard reaction conditions were 50 mM Tris-HCl pH8, 10 mM $MgCl_2$, with a ribozyme to substrate ratio of about 10:1. Reactions were initiated by adding 1–4 ng of substrate to ribozyme pre-mixed with buffer and incubated at 37° C. Reactions were stopped by adding formamide loading buffer with EDTA and the mixtures then fractionated by denaturing polyacrylamide gel electrophoresis. The products were quantified by phosphorimaging. The target RNA was a RNA 21 residue synthetic substrate (5'-UUCCCCCUUUCGCCAGCUCCC-3' (SEQ. ID. NO:XX)) and is based on part of the lacZ gene.

EXAMPLE 1

A. Helix II variants (Tables 1–5)

Most ribozyme variants of the satTobRSV helix II sequence reduced rates of cleavage. The exceptions fall into classes: loop sequence variants that probably increase the rate and stability of stem formation, and two stem-length variants that give less stable stem structures.

i) Cleavage efficiency of helix II stem-length variants

The middle two base-pairs of helix II were replaced with 0-6-A-U base-pairs and the variants tested for cleavage efficiency (Table 1). The two outer G-C base-pairs were retained in all cases. Internal A-U base-pairs were chosen as providing the smallest increments in stem stability.

The most notable feature is the lack of any simple correlation between stem-length and cleavage rates (2 bp–3 bp>control>4 bp=7 bp=8 bp>5 bp=6 bp; FIG. 1). Several competing factors appear to influence cleavage efficiency:

ii) stem-length variants that give increased cleavage efficiency (Table 1)

The two base-pair stem variant G-C, C-G (Table 1, #1) had a faster initial rate of cleavage than the control but the final proportion of cleavage products was reduced. One three base-pair variant G-C, A-U, C-G (Table 1, #2) cleaved more rapidly and to the same extent as the satTobRSV-based ribozyme. However, the sequence of the stem appears to be important, as the three base-pair stem G-C, C-G, G-C (Table 1, #3) reduced cleavage efficiency.

iii) mutations of conserved G-C base pair in helix II (Table 2)

The G-C base-pair adjacent to the catalytic core is strictly conserved in naturally occurring hammerhead ribozyme sequences. Most mutations, however, could cleave the substrate with moderate efficiency, including one variant (A-G; Table 2, #1) that had similar cleavage rates to the control. Intriguingly, this variant gave negligible cleavage in the system reported by Ruffner et al. [Ruffner, 1990].

A. Helix II variants (Tables 1–5)

i) Cleavage efficiency of helix II stem-length variants

The middle two base-pairs of helix II were replaced with 0-6-A-U base-pairs and the variants tested for cleavage efficiency (Table 1). The two outer G-C base-pairs were retained in all cases. Internal A-U base-pairs were chosen as providing the smallest increments in stem stability.

The most notable feature is the lack of any simple correlation between stem-length and cleavage rates (2 bp–3 bp>control>4 bp=7 bp=8 bp>5 bp=6 bp; FIG. 1). Several competing factors appear to influence cleavage efficiency:

1) stem stability, the 7 and 8 base-pair stems cleave faster than the 5 and 6 base-pair stems;
2) stem flexibility, the fastest ribozymes are those with 2 or 3 base-pairs (however the 2 bp stem variant yielded a lower overall percentage of cleavage products); and
3) sequence context, ribozymes with the same number of base-pairs or similar thermodynamic stability cleave at different rates.

Presumably the 4 base-pair stem is the optimal solution in nature. Clearly, however, faster cleaving variants can be devised in any one particular case or conditions. It would be worthwhile to test the robustness of the faster 3 base-pair variant (Table 1, #2) against other targets.

ii) Cleavage efficiency of the conserved G-C base-pair in helix II. (Table 2)

The 5' G-C 3' base-pair in helix II, that is adjacent to the catalytic core, is conserved in nature. Ruffner et al. [Ruffner, 1990] extensively mutated this ribonucleotide pair and found several examples with moderate but lower rates of cleavage. The results herein results correlate well with those findings (Table 2), including elimination of cleavage activity with a 5' C-G 3' base-pair (Table 2, #10). One notable exception was a cytosine to adenine substitution. Indeed, the 5' G-A 3' nucleotide pair gave comparable cleavage rates relative to the control (Table 2, #1); whereas, Ruffner al. [Ruffner, 1990] reported almost no activity with this nucleotide pair.

As the 5'-G-C-3' base-pair eliminates cleavage activity while all other nucleotide pairs retain low to moderate cleavage efficiency, base-pairing of these two nucleotides of helix II may not occur in the active ribozyme conformation. This notion is consistent with minizyme activity.

iii) Cleavage efficiency of helix II loop variants. (Table 3)

Helix II loops that differed in both sequence and size were tested for cleavage efficiency. The structure of RNA tetraloops have been studied extensively in vitro, showing differences in conformation and stem stability. Based primarily on ribosomal RNA sequences, the tetraloops most commonly favored in nature are 5'-UUCG-3' and 5'-GNRA-3': both of which enhance stem stability. The loop of helix II from satTobRSV (5'-GUGA-3') conforms to the latter class. Not unexpectedly, one tetra-loop variant with improved cleavage efficiency, 5'-GGGA-3' (Table 3, #1), also fits this pattern.

Interestingly, two penta-loops also increased cleavage rates (5'-CGGAA-3', Table 3, #14; and 5'-UUGGA-3', Table 3, #15). Unfortunately, the effect of penta-loops on stem stability has not been formally examine either structurally or thermodynamically.

All tri-loop variants reduced cleavage efficiency, probably by preventing formation of the adjacent base pair, leading to a penta-loop bounded by an A-U base pair and resulting in a stem of reduced stability.

In conclusion, although the loop sequence is redundant for cleavage activity, mutants can vary considerably in cleavage efficiency (Table 3): a few may actually increase cleavage rates, but many are likely to reduce cleavage rates.

iv) Cleavage efficiency of helix II stem mismatches

The introduction of mismatches into the stem of helix II lowered cleavage efficiency (Table 4). There appears to be a good correlation between stem stability and cleavage efficiency (Table 4).

v) Cleavage efficiency of minizyme variants

Of seven minizyme variants tested, only the UUUU (Table 5, #1) variant cleaved with moderate efficiency. In previous experiments with ribozyme and substrate arranged in cis, one minizyme 5'-GCGC-3', gave a higher percentage of cleave products after one hour than the UUUU minizyme. In trans, cleavage with the GCGC minizyme occurred only in the first of several experiments. This particular ribozyme will need to be resequenced.

In view of the large variation in cleavage efficiencies between minizymes, and previous results with the GCGC variant, it is possible that there are minizymes capable of faster cleavage rates than the UUUU (Table 5, #1) minizyme. Interestingly, the 5' and 3' nucleotides of the UUUU (Table 5, #1) and GCGC minizymes also correspond in sequence and position to highly favored nucleotide pairs in the fill-sized helix II (see A.ii and Table 2; and [Ruffner, 1990]).

EXAMPLE 1A

Additional Ribozyme assays of stem II variants

Stem II consists of highly conserved tandem ((anti)-A (anti) base-pairs proximal to the catalytic core and a helical extension with canonical Watson-Crick base pairing (Haseloff et al. 1988). In many hammerhead self-cleaving domains, stem II is linked by a three to five nucleotide loop (Hertel et al. 1992). The nucleotide sequences of the stem extension and loop are highly variable. To assess the importance of the stem II variable region for cleavage activity, mutations were created by nucleotide substitutions, additions or deletions in either the stem or the loop (FIG. 4).

Figure 2:
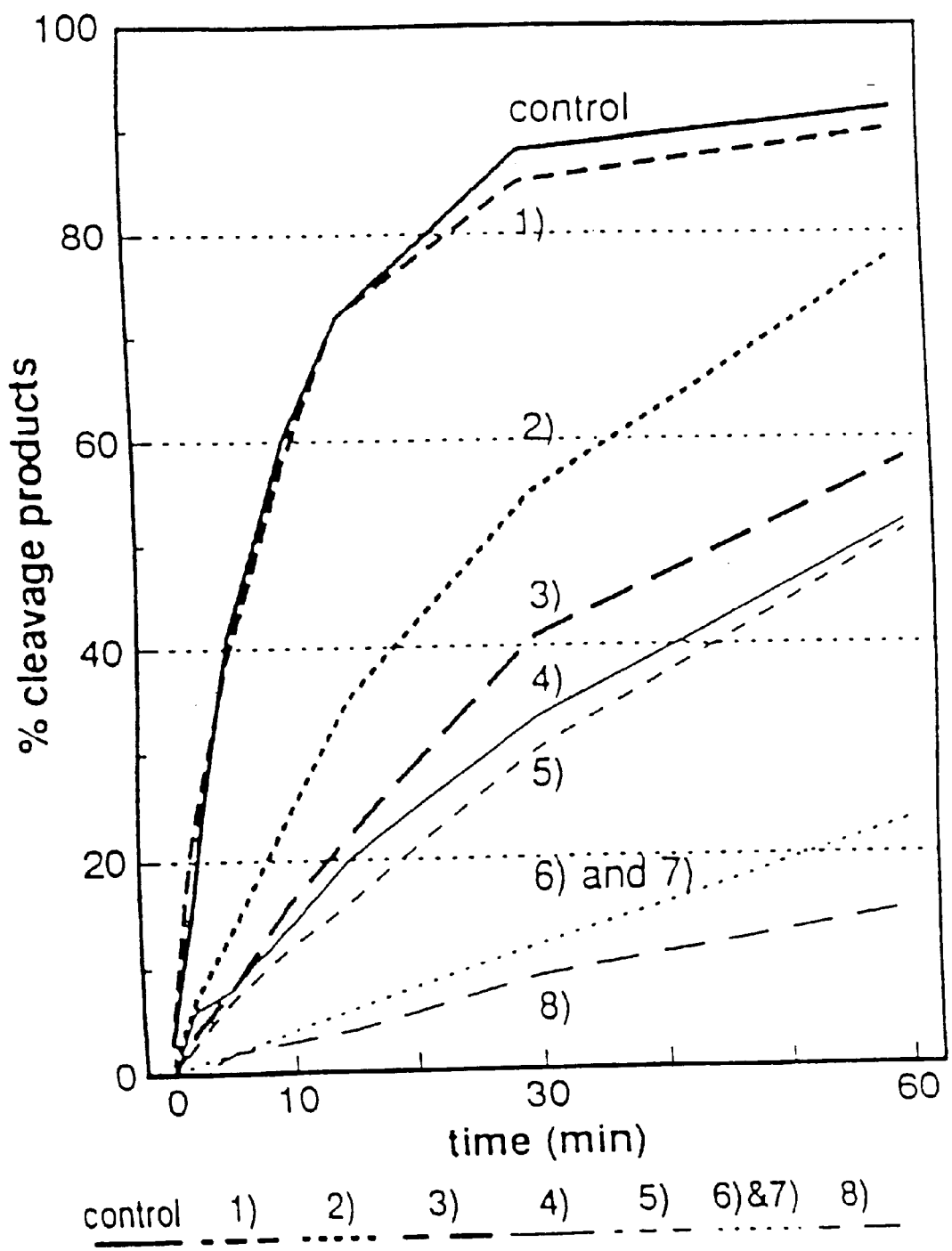
FIG. 2. Shows the cleavage efficiency of helix II ($(X)_m$ and $(X)_{m'}$ of formulas 1 and 2) conserved G-C base pair by plotting % cleavage as a function time in minutes. The data plotted is tabulated in Table 2 and each entry in Table 2 corresponds to each graph in the plot by number.

Mutant ribozymes with shorter stems of either five or six base pairs (Rz 2–5; FIG. 4) had rate constants up to 4.4 times greater than the seven base pair parent sequence. Reduced stem stability of the shorter stem ribozymes is likely to contribute to the increases rate constants, but further destabilization can greatly reduce cleavage rates. For example, increased loop size of five or six base paired ribozyme stem II variants (Rz 6–12; FIG. 4) sometimes gave very low relative rate constants (e.g. Rz 7–10). Similarly, Tuschel and Eckstein (1993) reported a modest 1.5 fold rate increase for one five base pair stem II ribozyme variant, but different loop sequences in this variant gave ribozymes with slower cleavage rates. In addition, low stem II stability in the form of a three base pair minizyme (McCall 1992) resulted in a 20 fold reduction in rate constant (FIG. 2: Rz 13), similar to reports by Tushel and Eckstein (1993) and Long and Uhlenbeck (1994).

Besides stability, the sequence and size of stem II appears to have additional effects that influence cleavage efficiency. For example, the length of stem II was increased incrementally with A-U base pairs (FIG. 4: Rz 14–18) but there was no linear relationship between stem length and rate constant. The ribozyme with ten base pairs (Rz 17) had faster cleavage rates than the eight (Rz 15), nine (Rz 16) and eleven (Rz 18) base paired variants but slower than the seven base paired forms (Rz 1, 14; FIG. 4).

Figure 4A:
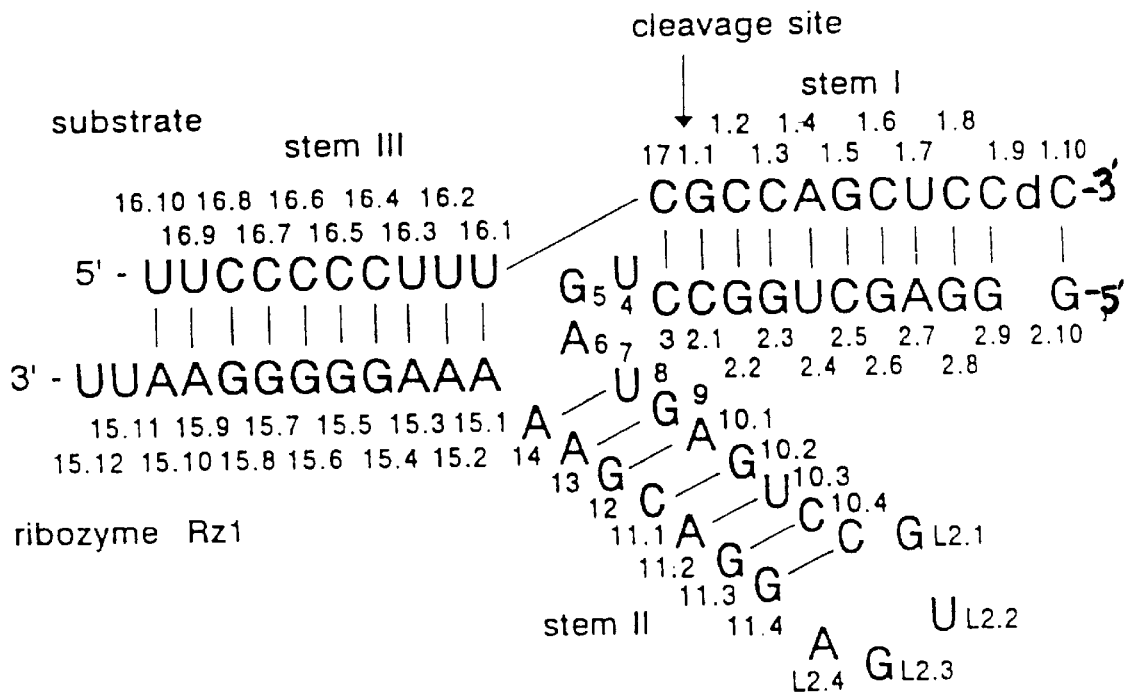
FIGS. 4A and 4B. Cleavage reaction of the parent ribozyme Rz 1.
Figure 4B:
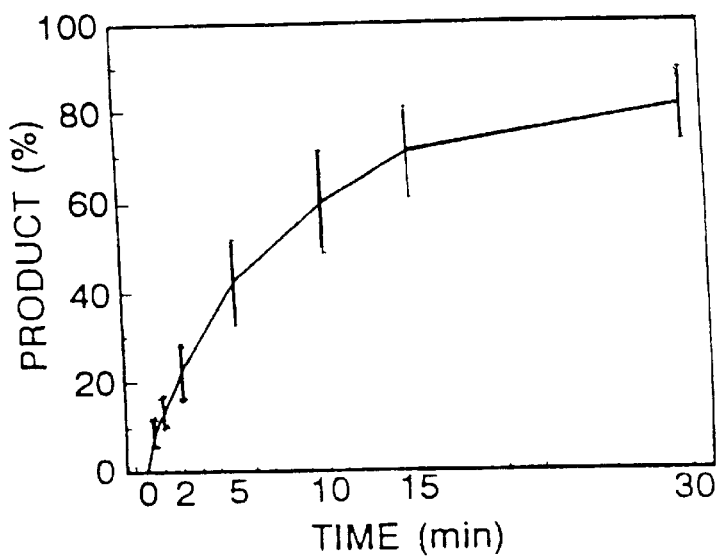

Variations in the size and sequence of the loop were also examined by randomly substituting three, four or five nucleotides for the parental tetraloop sequence 5'-GUGA-3' (FIG. 4; Rz 19–38). Although the majority of ribozyme loop variants had reduced rate constants, two ribozymes with tetraloops (Rz 22, 23) and two with pentaloops (Rz 33, 34) had increased cleavage rates.

Naturally occurring stem-loop structures within ribosomal RNAs strongly favor tetraloops with the consensus sequence 5-GNRA-3' (N, any nucleotide; R, purine; 25). The tetaloop sequence of the parent ribozyme 5'-GUGA-3' fits this pattern, as does one of the faster cleaving variants, Rz 22, 5'-GGGA-3'. However, a second faster cleaving tetraloop variant, Rz 23, 5'-GUGG-3', differs slightly from the 5'-GNRA-3' pattern. None (All) of the slower cleaving variants (Rz 24–32 do not conform to the 5'-GNRA-3' pattern. Similarly, Tuschel and Eckstein (1993) reported faster cleavage rates with a loop variant 5'-GAAA-3' than two other non-5'-GNRA-3' variants. It has been suggested that 5'-GNRA-3' sequences are biologically favored due to increased stability of the adjoining stem (Uhlenbeck 1990) or to specific three-dimensional conformation (SantaLucia et al. 1992). Another possibility is a greater capability of 5'-GNRA-3' sequences to form tertiary interactions (Biou et al. 1994; Pley et al. 1994 B). Interestingly, one tetraloop sequence, 5'-UUCG-3', that is also overrepresented in ribosomal RNAs (Woese et al. 1990) and adopts a similar conformation to the 5'-GNRA-3' tetraloop (Cheong, C. et al. 1990; Heus et al. 1991), give rise to a ribozyme variant (Rz 32) with the lowest rate constant of all tetraloop mutants examined (FIG. 4).

Systematic structural and functional studies of RNA triloops and pentaloops have not been reported. However, in our random sampling of six pentaloop variants (out of 1024 possible combinations), 33% gave increased rate constants. All three triloop variants that were tested, gave reduced rate constants.

EXAMPLE 2

B. Helix I and m variants (Tables 6 and Table 7 respectively)

i) The helix I (Table 6) variants demonstrate that maintenance of a stable base-pair 10 immediately adjacent to the cleaved ribonucleotide residue is critical for good cleavage rates.

ii) One helix I variant (Table 6, #1), in which continuous base-pairing extends for only three base-pairs, gave markedly increased cleavage rates.

iii) Increased stem stability of helix III generally correlated with increased cleavage rates, so long as the base-pairs proximal to the catalytic core were maintained.

B Helix I and III variants. (Tables 6 and Table 7)

Table 6 depicts cleavage efficiency of helix I variants. The two most significant findings are the crucial role of the base pair adjacent to the cleavage site and the possibility of significantly improving cleavage rates by reducing stem stability.

The substitution of the C residue with either A or G in the base pair adjacent to the cleavage site eliminated cleavage activity (Table 6, Table 7, and Table 8). Mutating the C residue to a U, allowing a G-U bond to form, greatly reduced cleavage efficiency (Table 6, #2). Even the strictly conserved G-C pair in helix II can be more readily modified (Table 2).

Stem mismatches elsewhere in helix I, however, sometimes gave increased cleavage rates. The most notable example includes one mutant in which only the first three base pairs adjacent to the cleavage site are retained before mismatching occurs (Table 6, #1). It is uncertain if the marked improvement in cleavage efficiency is due to structural properties of this modified helix I mutant or reduced stem stability. One simple test would be to use a shorter substrate as the target.

Unlike helix I, all helix III stem mismatches gave reduced cleavage rates. Cleavage efficiency seems most closely correlated with increased stem stability; with particular emphasis on maintenance of base pairing adjacent to the cleavage site. One minor anomaly appears to be the sequence 5'-AAUUGUGGGA-3' (SEQ. I.D. NO:15) (Table 7, #3) which appears to have poor base pairing possibilities and yet retains moderate cleavage efficiency.

In conclusion, helix III appears to have greater sequence specificity than helix I. It is uncertain, however, if this applies to other substrate sequences. At present, most short-armed ribozymes target an equal number of base pairs either side of the target. An uneven distribution of base pairs may prove optimal.

EXAMPLE 3

C. Enhancement of cleavage rates by complementary oligonucleotides. (Table 8)

i) DNA oligonucleotides of 8–10 residues complementary to either the catalytic core or the hybridizing arms of the ribozyme, increased cleavage rates.

ii) This enhancement of cleavage efficiency could be mimicked by complementary RNA oligonucleotides of six residues, but not by free nucleotides, spermine or polyethylene glycol, or denaturants such as formamide or urea.

C. Enhancement of cleavage rates by complementary oligonucleotides. (Table 8)

A series of different sized oligodeoxynucleotides were devised to complement different regions of the ribozyme. The aim was to test which regions of the ribozyme are most sensitive to interference by competing oligonucleotides. The oligodeoxynucleotides were pre-incubated with ribozyme in 5× excess, at 100° C./1' and snap cooled on ice. Specific binding of the oligonucleotides to the ribozyme was tested by RNaseH digestion. Surprisingly, these substrate analogs, rather than acting as typical enzyme inhibitors, actually increased cleavage efficiency (Table 8, #1–11). However, there appears to be an optimal stability range for the oligonucleotide-ribozyme interaction: high enough to allow binding, but low enough to allow displacement by the substrate. Improved cleavage efficiencies could also be achieved with complementary oligoribonucleotides (Table 8, #12–16). One possible explanation is that the oligonucleotides prevent formation or stabilization of inactive ribozyme conformers.

Enhancement of cleavage efficiency could not be achieved by the addition of free deoxynucleotide residues, spermine or polyethylene glycol, or by denaturants such as urea or formamide (Table 8, #17–28).

It may be useful to determine if the complementary oligonucleotide sequences could enhance activity when added in cis as part of the ribozyme transcript.

EXAMPLE 4

In vivo studies on the ribozymes of formula 4

The present invention is directed to a plant tyrosine tRNA (Stange and Beier, 1988) to deliver hammerhead ribozyme and antisense RNAs against a reporter gene, chloramphenicol acetyl transferase (CAT), to plant protoplasts using a vector derived from African cassava mosaic geminivirus (ACMV—Stanley, et al.). Geminiviruses are plant DNA viruses that rely on host components for replication, are localized in the nucleus and can replicate to high levels. For these reasons geminiviruses provide the basis for excellent vector systems for assaying plant gene expression.

Compared to work of Cotten and Birnsteil (1989), the present invention is different in several respects. First, in the present invention, a tyrosine tRNA from Nicotiana (tobacco) was used instead of methionine tRNA-Xenopus. Second, the present invention uses a CAT mRNA target which is synthesized in vivo (nuclear/cytoplasmic). Cotten and Birnsteil used a U7snRNA which was synthesized in vitro and then microinjected (cytoplasmic). The target site on the RNA target molecule was different as well; i.e.—a GUC (present invention) verses a CUC (Cotten and Birnsteil). The present invention used an antisense control as well as a mutant target in order to test the activity of the tRNA embedded ribozyme. Cotten and Birnsteil did not use such controls. Finally, most of the active tRNARz12 transcripts of the present invention are RNA polymerase III derived.

The present invention is directed to the design of improved hammerhead ribozymes (a) in vitro and (b) in vivo.

a) in vitro

In the present invention, new hammerhead ribozymes were designed from experiments performed on the satellite RNAs of tobacco ringspot virus (sTobRSV). Some of the ribozymes developed show higher rates of cleavage in vitro than the native sTobRSV ribozyme. The present invention is also directed to compositions partly consisting of these new hammerhead ribozymes.

b) in vivo

The present invention is also directed to tRNA embedded hammerhead ribozymes. A tRNA embedded hammerhead ribozyme is created by embedding a hammerhead ribozyme into a tRNA molecule. The tRNA embedded hammerhead ribozyme shows decreased effectiveness in vitro but significant enhancement in its activity in-vivo, relative to the non-embedded ribozyme. These results were based on in vivo cleavage of a target CAT mRNA molecule. Control studies further support the observed reductions in CAT activity as due to tRNA embedded hammerhead ribozyme function in vivo. The controls included the use of antisense molecules.

Materials and Methods
Plasmid constructions

All oligodeoxyribonucleotides were synthesized on an Applied Biosystems model 392 DNA synthesizer (Applied Biosystems). Molecular cloning and related techniques were carried out essentially as described by Sambrook, et al. 1989).

(i) tyrosine tRNA

A clone of the tyrosine tRNA was obtained from the laboratory of Hildberg Beier [Stange and Beier, 1986]; FIG. 9a) and subcloned as an AccI/SspI fragment into like digested pGEM3zf-(Promega) to make pGEMtRNA. A short oligodeoxyribonucleotide, containing three restriction enzyme recognition sites (BamHI, SmaI, EcoRI), was inserted within the anti codon loop of the tRNA by site directed mutagenesis [Kunkel, et al., 1987] to make pGEMtRNApoly. This is the site of subsequent insertions of both ribozyme and antisense sequences.

Figure 9B:
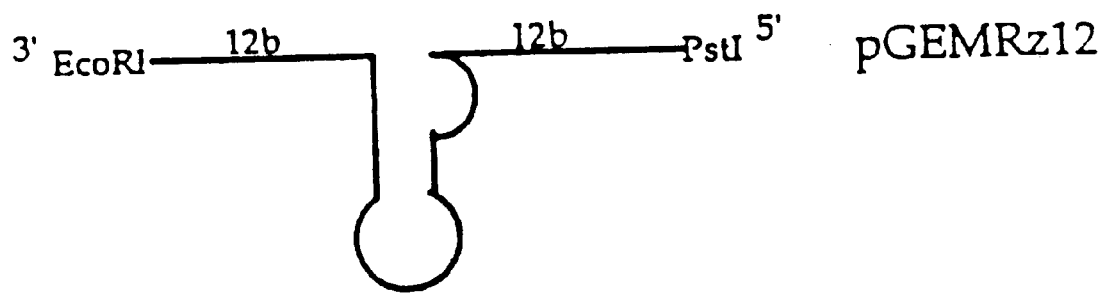

(ii) Ribozyme/Antisense (FIG. 9b)

Figure 9C:
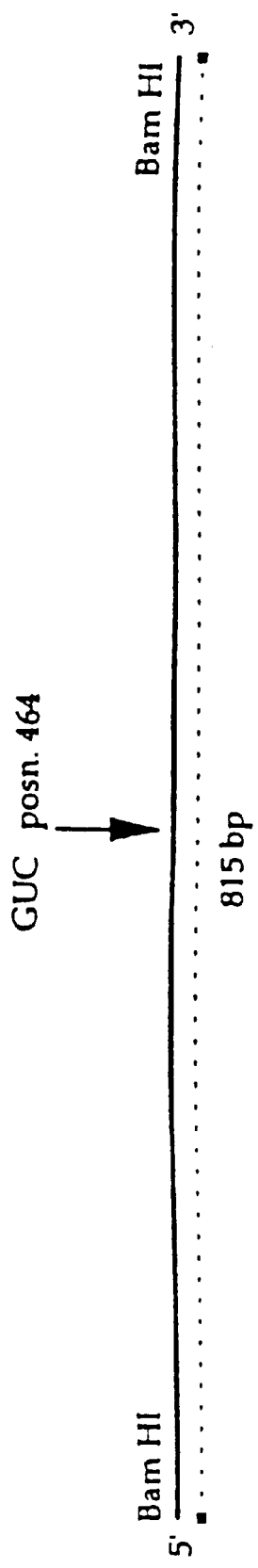

Overlapping oligodeoxyribonucleotides encoding ribozyme Rz12 contained the hammerhead motif plus 12 bases upstream and downstream of this motif. The double stranded oligodeoxyribonucleotide was cloned into EcoRi PstI digested pGEM4z to make pGEMRz12. This ribozyme is designed to cleave CAT mRNA at position 464 as shown in FIG. 9c. Antisense control, representing the equivalent hybridization to the CAT mRNA as the ribozyme sequence, is as described in Cameron and Jennings (1989). The ribozyme was subcloned into SmaI digested pGEMtR-NApoly as an end-filled EcoRi PstI fragment to make the clone pGEMtRNARz12. The antisense sequence was subcloned as a BamHI SnaBI fragment into BamHi SmaI digested pGEMtRNA poly to make the clone pGEMtR-NAAs24.

(iii) CAT substrate

The CAT sequence was as described in Haseloff and Gerlach, 1988 and Perriman, et al., 1993. Sequence length and ribozyme target site are diagrammed in FIG. 9c.

(iv) Mutant CAT substrate

The GUC target site at position 464 on the CAT gene was mutated to a GUG by site directed mutagenesis [Kunkel, et al., 1987] using a specifically designed oligodeoxyribonucleotide. This mutation maintains codon usage and does not affect in vivo CAT activity. The plasmid bearing mutated CAT sequence is called pGEMCM-2.

(v) Geminivirus vector construction

Figure 9D:
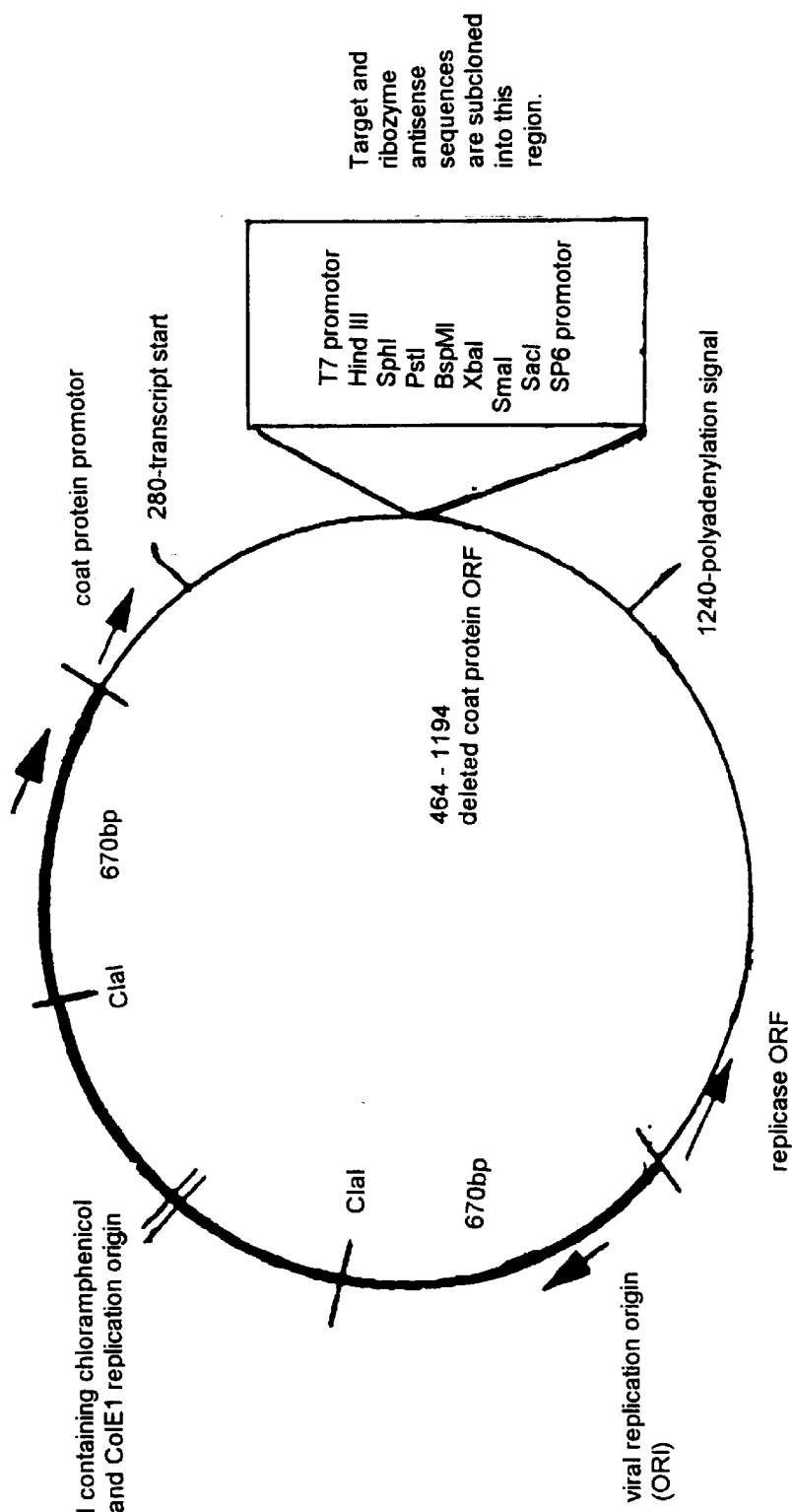

The infectious clone of the A component of the geminivirus African cassava mosaic virus (ACMV) was a gift from Stanley, et al., (1988). Modification to this vector included the insertion of a pUC19-derived plasmid carrying, bacterial origin of replication and chloramphenicol resistance gene [Chay and Feldstein, unpublished; FIG. 9d). In this construction a pUC19-derived poly linker ant T7 and SP6 RNA polymerase recognition sites were inserted in place of the coat protein open reading frame. Into this region were subcloned the wildtype (pACMVCAT) and mutant (pACMVCM2) targets as well as non-embedded (pACMVRz12, pACMV As24) and tRNA-embedded (pACMVtRNARz12, PACMVtRNAAs24) ribozyme and antisense sequences. Upstream of all sequences is the endogenous coat protein promoter, while downstream are coat protein termination and polyadenylation signals.

In vitro cleavage assay

RNAs for the in vitro assays were prepared by in vitro transcription as follows: 1–2 mg linearized template DNA, 40 MM Tris-HCI (pH 7.5) 6 mM MgCl$_2$, 2 mM spermidine, 10 mM NaCl, 10 mM DTT, 8 units RNasin (Promega), 1 mM rATP, rGTP, rUTP and 0.25 mM rCTP (Pharmacia) in a final volume of 50 ml. CAT and CM2 target RNa were transcribed in the presence of 60 pmoles of [a-$^{32}$P] CTP (Amersham; 400 Ci/mmol) using 25 units of T7 RNA polymerase (Bethesda Research Labs). The ribozyme sequences, pGEMRz12 and pGEMtRNARz12, were transcribed in the presence of 1 mM CTP and 25 units of RQ-1 DNaseI (Promega) to remove the DNA template. Transcript yields and the size and fidelity of RNAs were confirmed by electrophoresis through 6% polyacrylamide gel in 7M urea (denaturing PAGE).

CAT or CM2 target RNAs and ribozyme (Rz12 or tRNARz12) were mixed on ice prior to the addition of buffer (10 mM MgCl$_2$, 50 mM Tris-HCi, pH7.4). The reactions were immediately transferred to 30° C. for one hour. Reactions were terminated by the addition of EDTA to a final concentration of 50 mM followed by ethanol/sodium acetate precipitation. Cleavage rates were quantitated using an AMBIS Image Acquisition analyzer (AMBIS, Inc.).

Analysis of in vivo expression (i) Transfection

A cell culture of Nicotiana tabacum (cv. Xanthi) was used for protoplast isolation essentially as described by Howard, et al. (1987). Protoplasts were suspended at a concentration of 1.2×10$^6$/ml, with 700 ml aliquot used per transfection. Transfection was obtained by electroporation using a Hoefer PG200 progenitor II apparatus (Hoefer Scientific Instruments, San Francisco, California). Each electroporation involved the co-electroporation of the target construct (either pACMVCAT or pACMVCM2) with (a) control pACMVtRNA or either (b) the antisense constructs (pACMVAs24 or pACMVtRNAAs24), or (c) the ribozyme constructs (pACMVRz12 or pACMVtRNARz12), so that each event involved the same amount of input DNA. The amount and ratio of target to control, antisense or ribozyme construct was 1:3 (5 mg pACMVCAT or pACMVCM2: 15 mg pACMVtRNA, pACMVAs24, pACMVtRNAAs24, pACMVRz12 or pACMVtRNARz12). This results in approximately a six-fold molar excess of tRNA-embedded antisense/ribozyme inserts over the target molecule. Each construct pairing was replicated a minimum of three times for each protoplast isolation. The conditions for electroporation were 490 mF capacitance, 330 volts, single 8 msec pulse with the electrodes in the electroporation chamber separated by 0.4 mm. Following electroporation, cells were transferred to culture dishes and incubated in 3 ml growth media (5% coconut water, 95% MS organics [Gibco-BRL], 265 mM mannitol, 0.1 mg/ml kinetin, 0.2 mg/ml 2–4-D, 1.5 mM KH$_2$PO$_4$, 0.5 mg/ml each of nicotinic acid, pyroxidine and thiamine) at 26° C. for three days. At this time cells were harvested and assayed for CAT activity, ACMV DNA replication and mRNA levels.

(ii) CAT assays

Following incubation, 0.5 ml of cell suspension were harvested for CAT assays. The remaining 2.5 ml were used to isolate nucleic acids. Cells were collected at 80×g for 10 mins and resuspended in 200 ml 0.25M Tris-HCl (pH7.4) before being transferred to 1.5 ml eppendorf tubes. The cells were sonicated and extracts were centrifuged at 14,000×g for 10 mins to remove cell debris. Protein concentrations were determined using Bradford assay kit (Biorad). Equivalent amounts of protein for each extract were incubated at 37° C. for 60 mins in the presence of 5 ml of 10 mM acetyl-Coenzyme A (Sigma) and 18 picomoles of C$^{14}$ chloramphenicol (Amersham). Reactions were stopped by the addition of 700 ml ethyl acetate. The ethyl acetate phase was dried and suspend in 10 ml of ethyl acetate for separation on silica gel thin layer chromatography in 5% methanol and 95% chloroform. Radioactive products were detected by autoradiograph and then quantitated using an AMBIS Image Acquisition analyzer to determine the proportion of $C^{14}$ chloramphenicol that had been acetylated. The average rates of acetylation were plotted using Lotus Freelance graphics (Lotus, Cambridge, Mass.).

(iii) DNA isolation

Cells were collected as for the CAT assays and resuspended in 200 ml TE. An equal volume of 2×SDS extraction buffer (0.1 mM Tris, pH7.4, 2 mM EDTA, 2% SDS) was added and the solution mixed. Proteinase K (Boehringer Mannheim) was added to 100 mg/ml and the solution incubated at 37° C. for 30 minutes. Following this, samples were extracted with equal volumes of phenol/chloroform and then nucleic acids precipitated in ethanol/sodium acetate. Nucleic acid samples were treated with 10 mg RNase A (Sigma) to remove contaminating RNA prior to restriction enzyme digestion. DNAs were suspended at a concentration of 0.5 mb/ml. Routinely 1–2 mg of total DNA was digested with either DpnI or MboI and analyzed by southern blot analysis.

(iv) RNA isolation

Total RNA was isolated from cells using Trizol solution (Gibco BRL) as per manufacturers specifications. RNA was suspended at a final concentration of 1 mg/ml and was analyzed by electrophoresis through non- denaturing 1% agarose.

(v) Reverse transcriptase-PCR (RT-PCR) analysis of in vivo CAT mRNA. First strand cDNA synthesis was carried out with 5 mg of total RNA using 200 units of Superscript reverse transcriptase (Gibco-BRL). cDNA synthesis was carried out at 45° C. to minimize any interference by RNA secondary structure. The first strand primer was oligo dT with an 18 base unique sequence ("TAG"—Lincoln & Karrer, unpublished) at the 5' end of the primer. This TAG sequence was used to prime for subsequent PCT amplifications. Dual PCR reactions were carried out on reaction samples. Primer 1 which primes at positions 198 to 216 on the CAT sequence was designed to amplify full length CAT sequence. Primer 2 anneals at positions 470 to 488, just 3' of the ribozyme cleavage site and acts as a positive control for the presence of CAT RNA, cleaved or uncleaved. Conditions for the PCR reaction were verified to be within linear range of amplification and were as follows: 52° C. 22 mins, 72° C. 40 mins, 30 cycles of 94° C. 40secs; 52° C. 2 mins; 72° C. 3 mins followed by 72° C. 15 mins. Amplification was carried out using either 1+TAG or 2+TAG primer pairs. ⅙ of the PCR reactions were loaded on agarose gels and southern blotted to determine the extent of amplification of the CAT sequence by the two primer pairs. Southern blotting was carried out as described in Sambrood, et al. (1989). Filters were analyzed by autoradiograph and total counts determined using an AMBIS image acquisition analyzer.

Results

Efficiency of in vitro cleavage by the linear and tRNA embedded ribozymes

Figure 10A:
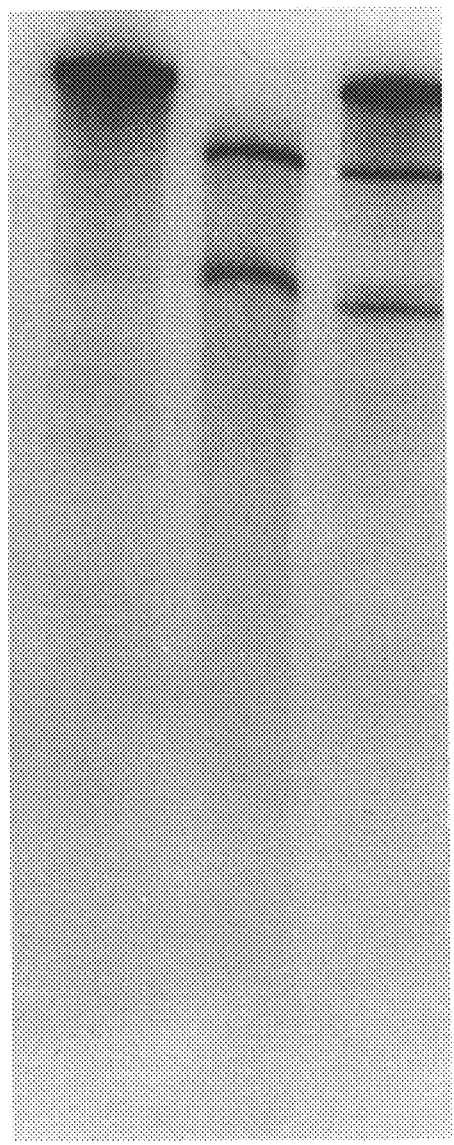
FIGS. 10A–10B. In vitro cleavage by linear and tRNA embedded ribozymes. (10a). Autoradiograph of in vitro cleavage reaction at 30° C. for 1 hour. The CAT substrate but not the ribozymes were radioactively labelled in these reactions. The lanes labelled 1 to 3 represent: 1, CAT RNA incubated alone; 2, CAT RNA+Rz12; 3, CAT RNA+ tRNARz12. The RNA species are as follows: Sub, CAT substrate RNA; 5'P, cleavage product 5' of target site; 3'P, cleavage product 3' of cleavage site. (10b) Bar graph of in vitro cleavage reactions showing average % cleavage of CAT transcript in three independent cleavage reactions. Y axis shows % cleavage and error bars represent 2 standard deviations.
Figure 10B:
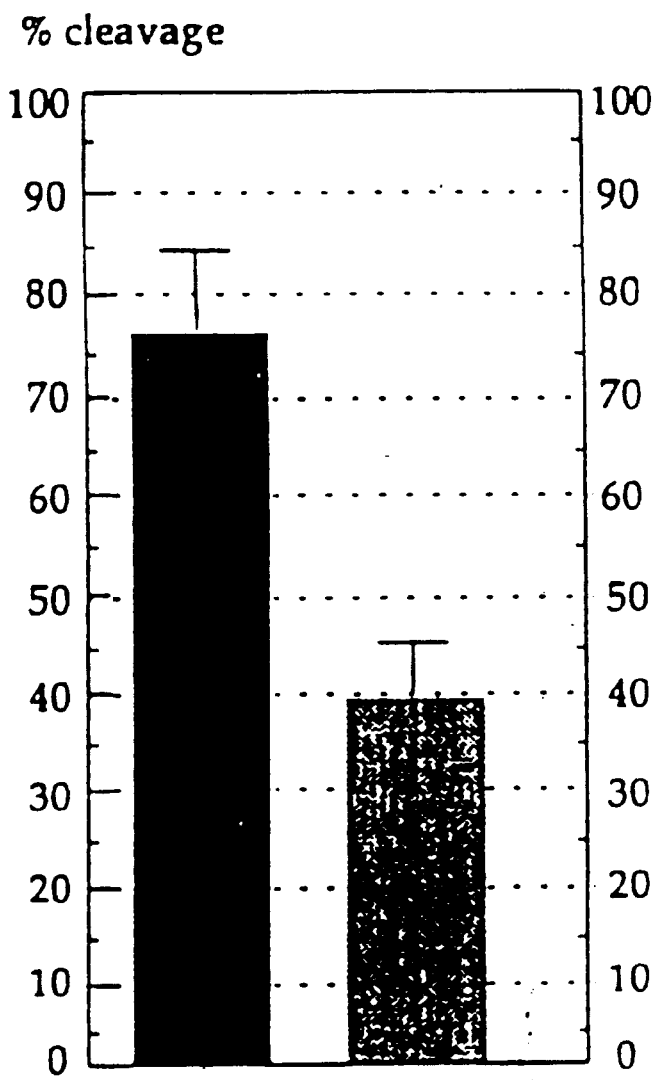

In vitro cleavage assays were carried out to test the efficiency of the linear and tRNA embedded ribozyme constructs in cleaving the CAT transcript. As shown in FIG. 10a, cleavage of the CAT RNA was dependent upon the addition of either the linear or tRNA-embedded in ribozyme sequences. Both constructs cleaved the CAT RNA efficiently although as shown in FIG. 10b, the non-embedded ribozyme (linear) cleaved more efficiently than the tRNA-embedded form. In the present example, a reduction in substrate was used as a measurement of cleavage in these in vitro assays. This quantity is the percentage of substrate calculated to have been cleaved to form the two product bands visible in FIG. 10a after one hour incubation at 30° C., based on radioactivity associated with bands for transcript and the two cleavage products.

In three independent experiments CAT RNA was cleaved to the average extent of 75% when incubated with the linear ribozyme. For the tRNA embedded ribozyme, the average extent of CAT RNA cleavage was only 38%. These results, including standard deviations, are shown in FIG. 10b. Incubation of the CAT transcript with the linear and tRNA-embedded antisense transcripts did not yield these cleavage products. Additionally, incubation of the mutant target transcript, CM2, with the two ribozyme transcripts also showed no accumulated cleavage products (data not shown). Significantly reduced levels of in vitro CAT activity in the presence of the tRNARz12 ribozyme Having shown that both ribozymes are capable of cleaving the substrate RNA in vitro, is the relative effects of these on CAT gene expression from Xanthi tobacco suspension cells was examined. In seven separate experiments using different protoplast preparations, the addition of the tRNA-embedded ribozyme gene construct resulted in greater suppression of CAT activity than was observed after the addition of the constructions expressing the antisense sequence in the non-embedded or tRNA-embedded form or a construction bearing the non-embedded ribozyme (FIGS. 10a and 10b). These results are in contrast to those obtained for the in vitro assays, in which the non-embedded ribozyme was more efficient at cleaving the CAT transcript. The mutated CAT target, CM2, did not show the enhanced CAT gene suppression observed for the wildtype CAT target. A CAT assay showing the effect on CAT activity compared with the effect on CM2 activity of the tRNARz12 transcript is shown in FIGS. 12a and 12b. Results obtained for each experiment were normalized by assignment of a value of 100% to the expression of pACMVCAT or pACMVCM2 in the presence of pACMVtRNA and in the absence of any of the antisense or ribozyme constructs (FIGS. 11a and 11b).

Figure 11A:
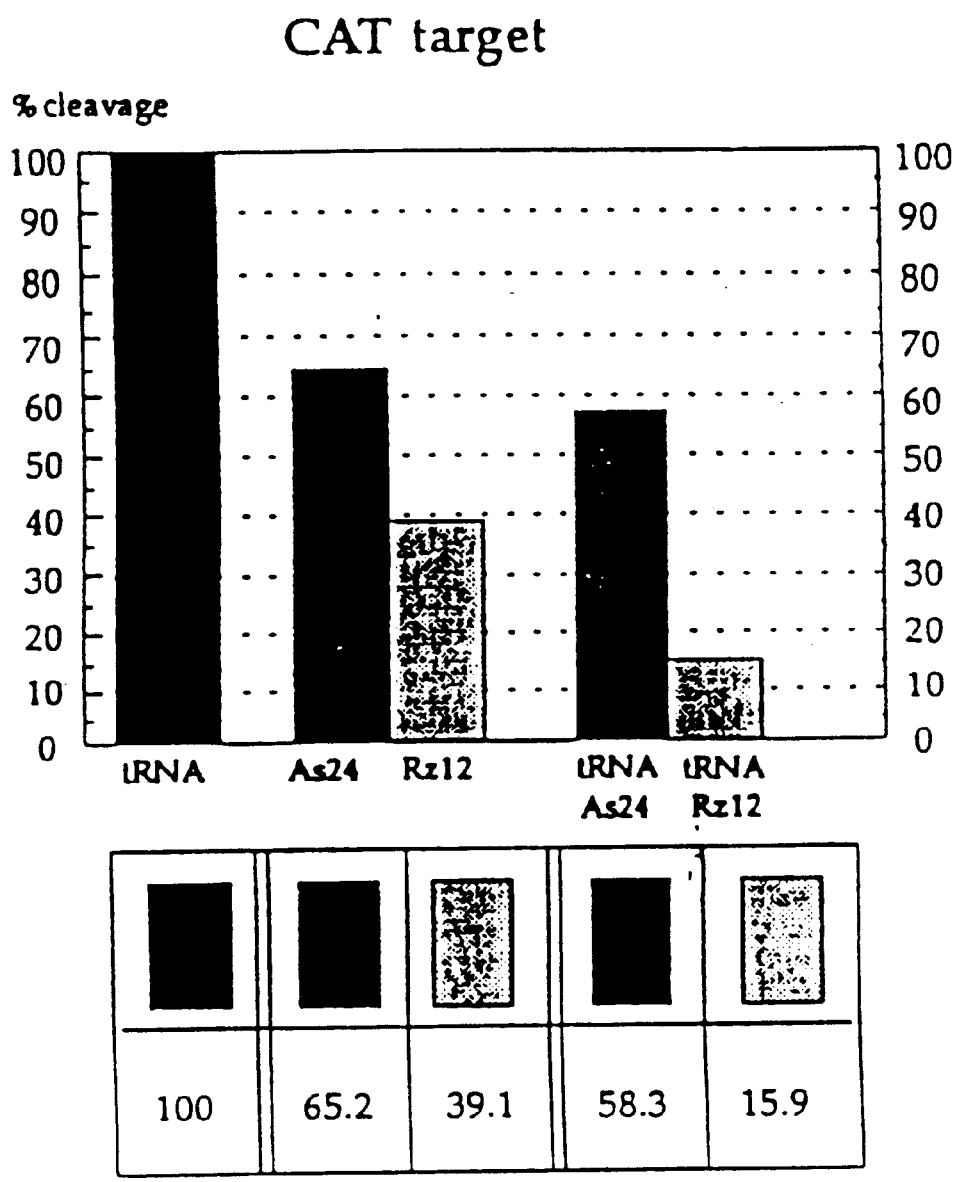
FIGS. 11A–11B. Relative expression of the wildtype (CAT) (11A) and mutant (CATMUT2) (11B) genes in the presence of pACMVtRNA (control), pACMVAs24 or pACMVtRNAAs24 (antisense), pACMVRz12 or pACMVtRNARz12 (ribozyme) in *Nicotiana tabacum* protoplasts. The figures show the results from seven separate protoplast isolations. Each bar represents the mean relative value of CAT or mutant CAT expression, upon addition of the antisense or ribozyme in the tRNA-embedded form. Control CAT or CATMUT2 activity has been normalized as 100%. Each protoplast isolation and subsequent electroporation involved at least triplicate samples of each of the construct combinations: i.e.; CAT (or CATMUT2)+control, CAT (or CATMUT2)+antisense (tRNA embedded or non-embedded) and CAT (or CATMUT2)+ribozyme (tRNA embedded or non-embedded).
Figure 11B:
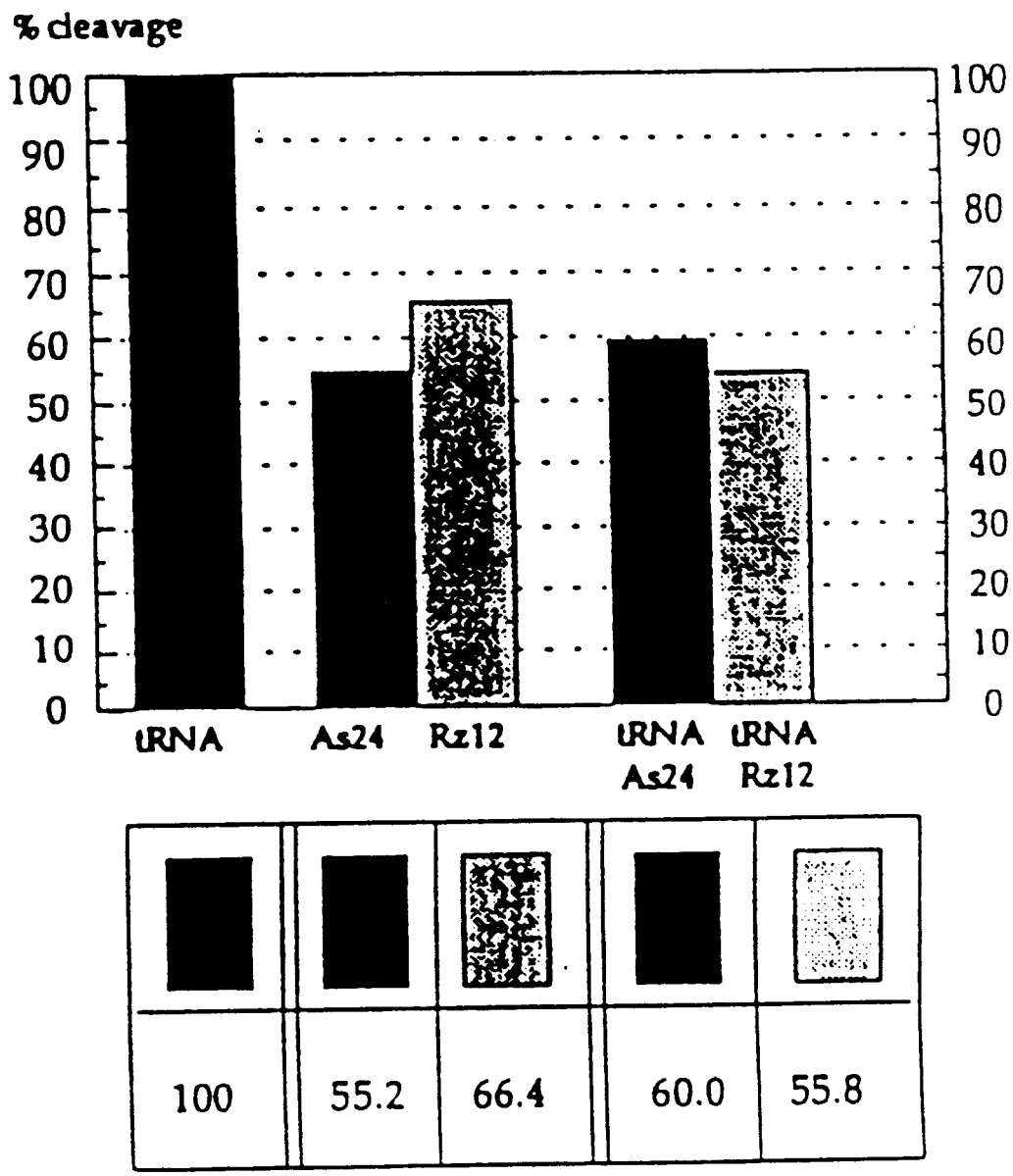
Figure 12A:
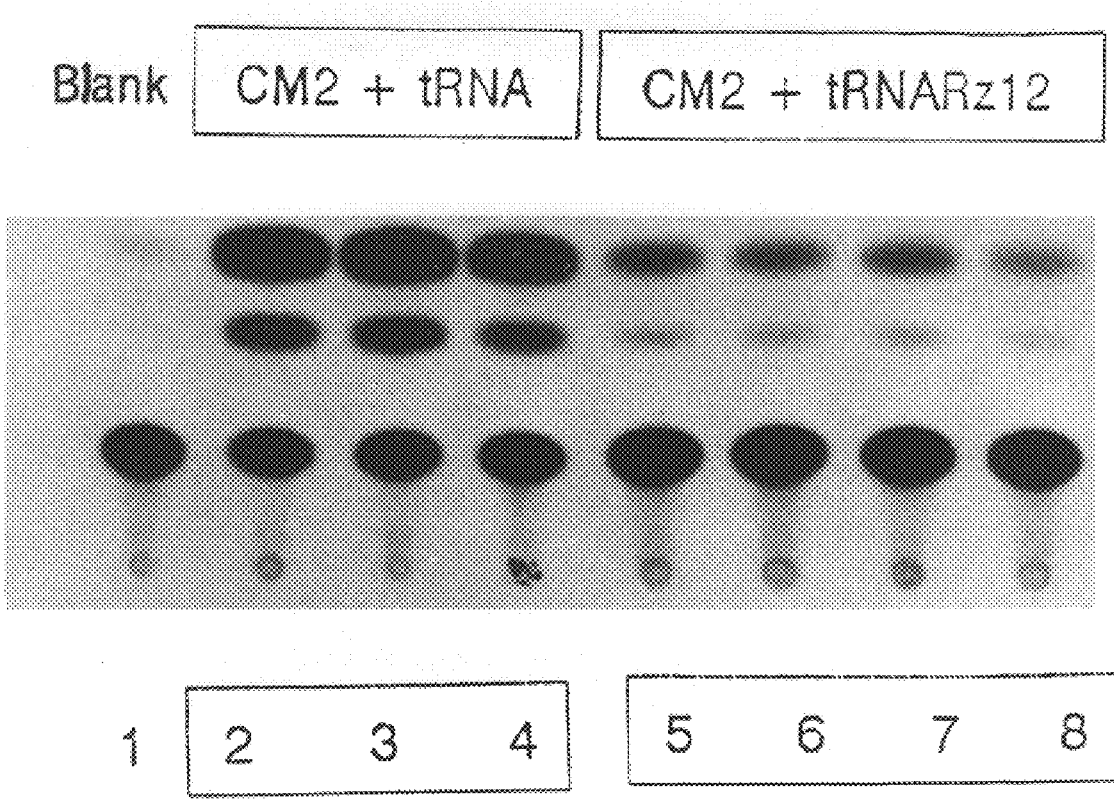
FIGS. 12A–12B. Autoradiograph of thin layer chromatography plate showing relative CAT (12A) or CATMUT2 (12B) activity in the presence of pACMVtRNA or pACMVtRNARz12. For CAT+tRNA or CM2+tRNA, three independent electroporations are shown (labelled 2–4). For CAT+tRNARz12 or CM2+tRNARz12, four independent electroporations are shown (labelled 5–8). Control lanes (1) are mock inoculated protoplasts.
Figure 12B:
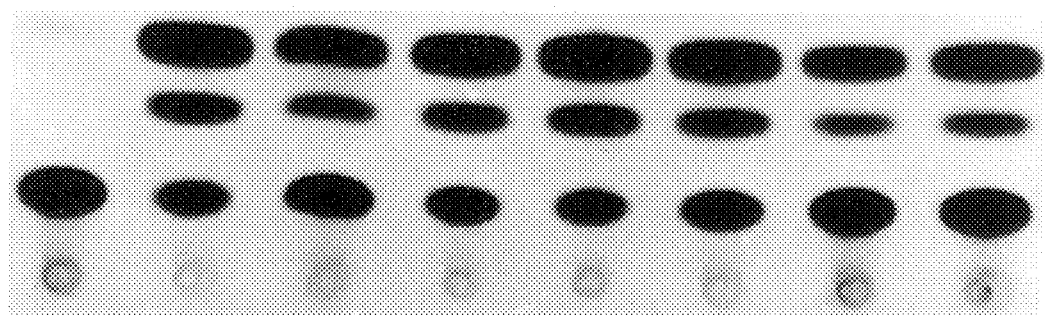

As shown in FIGS. 11a and 11b, the average reduction of the CAT gene expression, when the antisense gene construct is delivered as a non-embedded sequence is to about 60% of the control value. By comparison, the non-embedded and tRNA-embedded ribozymes were able to reduce CAT activity to 40% and 15% of controls, respectively. When the target sequence was CM2, which is the CAT target, all four constructs reduce CAT activity to the 60% level. Table 9 shows T-test analysis of pair-wise comparisons of CAT activity in the presence of either of the ribozyme or antisense constructs and the CAT and CM2 target. These T tests include each data point which make up the means shown in FIGS. 12a and 12b. For each construct pairing this represents 24 separate electroporation events. At>99% confidence level, 1. The tRNARz12 construct caused significantly lower levels of CAT activity than either of the antisense or the non-embedded ribozyme sequences when targeting the CAT construct,
2. CAT activity for the CAT construct in the presence of the tRNARz12 construct was significantly lower than that for the CM2 mutant target construct, with the same ribozyme constructs produced significantly different levels of CAT activity.
3. For the CM2 target, none of the two antisense or two ribozyme constructs produced significantly different levels of CAT activity.

TABLE 9

T-test analysis of co-transfected CAT (CATMUT2) + antisense or ribozyme constructs. T-tests were carried out comparing each of the points which make up the means shown in Figures 11a and 11b. Partwise comparisons of each of two construct combinations were carried out. A T-value greater than 99% indicates the values are significantly different in one another.

| Co-transfections | T value > 99% level of Probability |
|---|---|
| CAT + Rz12 v CAT + As24 | YES |
| CAT + tRNAAs24 v CAT + tRNARz12 | YES |
| CAT + tRNARz12 v CAT + Rz12 | YES |
| CAT + tRNAAs24 v CAT + As24 | NO |
| CAT + tRNARz12 v CM2 + tRNARz12 | YES |
| CAT + tRNAAs24 v CM2 + tRNAAs24 | NO |
| CAT + As24 v CM2 + As24 | NO |
| CAT + Rz12 v CM2 + As24 | NO |
| CM2 + tRNARz12 v CM2 + tRNAAs24 | NO |
| CM2 + Rz12 v CM2 + As24 | NO |

Analysis of replication of pACMV target, antisense and ribozyme constructs

Figure 13A:
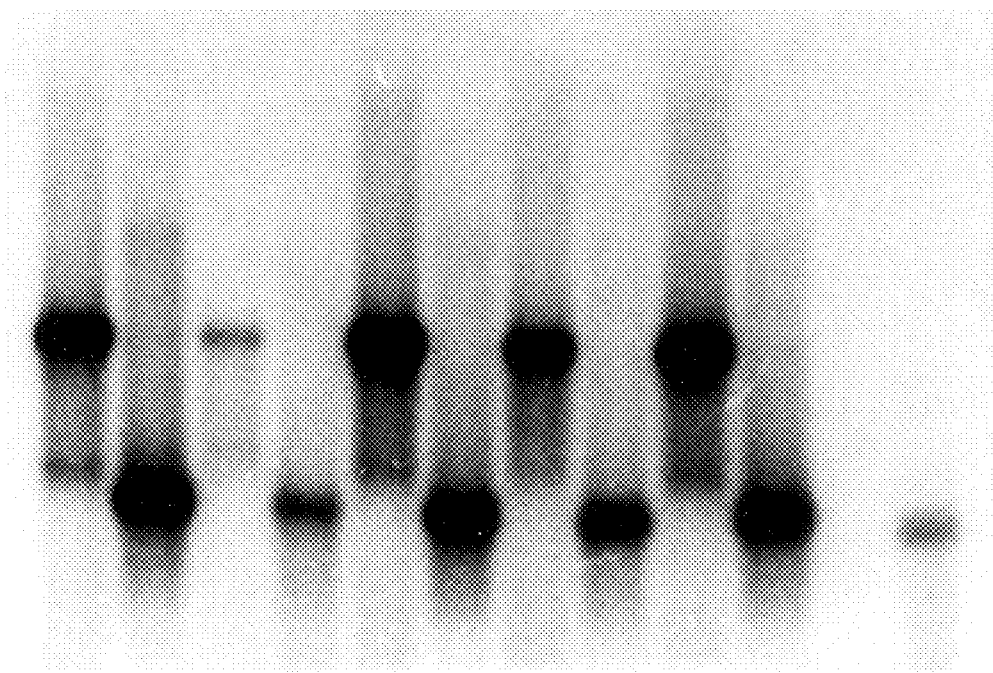
FIGS. 13A–13B. Analysis of CAT mRNA level in vivo. Southern blot of RT-PCR products from total RNA isolated from electroporated *Nicotiana tabacum* protoplasts. The two blots (FIGS. 11a and 11b) show accumulated products of full length CAT mRNA and CAT mRNA 3' of the GUC cleavage site. The lanes for the CAT and CM2 full length CAT mRNA, 4+tRNARz12-3' CAT mRNA, 5,+tRNAAs24–full length CAT mRNA, 6+tRNAAs24-3' CAT mRNA, 7+Rz12-full length CAT mRNA, 8–Rz12-3' CAT mRNA, 9+As24–full length CAT mRNA, 10+As24-3' CAT mRNA. Blots were probed with ssDNA representing full length CAT sequence. Also, see Table 10: Ratio of accumulation of 3' product to full length CAT product. Table 10 shows the ratio of these products for each of the construct combinations. These ratios are the accumulated data from two independent experiments.
Figure 13B:
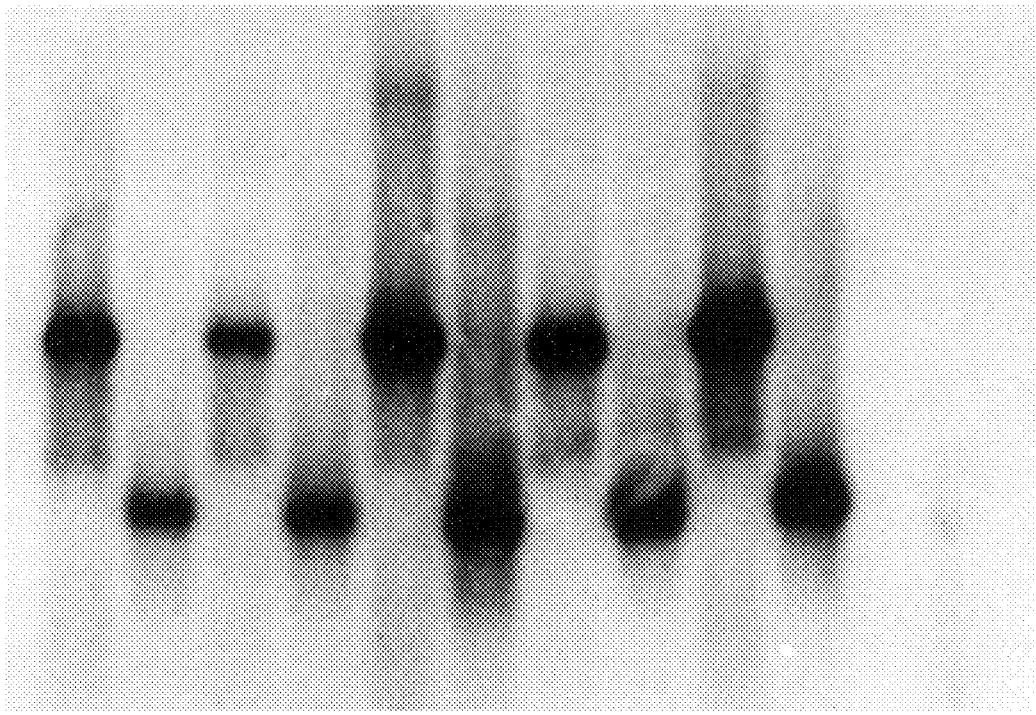
Figure 14A:
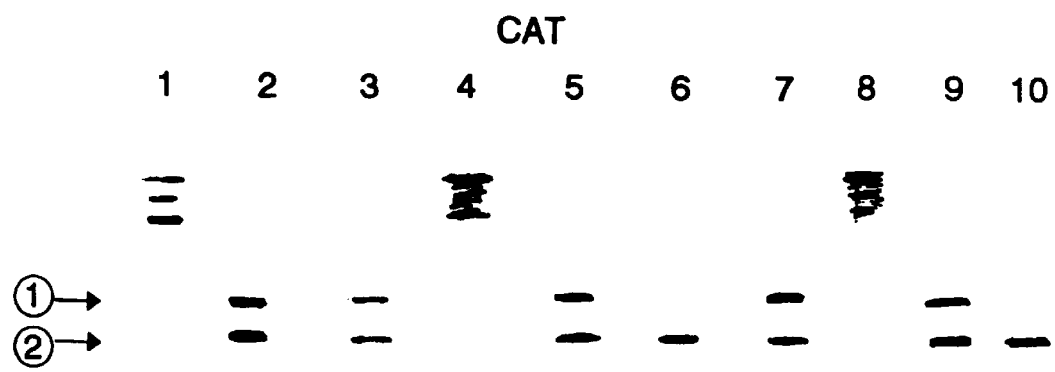
FIGS. 14A–14B. Lane 1: 20 ng pACMVCAT or pACMVCM2 MboI restricted. Lane 2: 20 ng pACMVCAT or pACMVCM2 DpnI restricted. Lane 3: 1 ug transfected DNA (time zero), pACMVCAT/CM2 input only, DpnI restricted. Lane 4: 1 ug transfected DNA (time zero), pACMVCAT/CM2 input only, MboI restricted. Lane 5: 1 ug transfected DNA (time: 3 days), pACMVCAT/CM2 input only, DpnI restricted. Lane 6: 1 ug transfected DNA (time: 3 days), pACMVCAT/CM2 input only, MboI restricted. Lane 7: 1 ug transfected DNA (time zero), pACMVCAT/CM2 +pACMVtRNARz12, DpnI restricted. Lane 8: 1 ug transfected DNA (time zero), pACMVCAT/CM2+ pACMVtRNARz12, MboI restricted. Lane 9: 1 ug transfected DNA (time: 3 days), pACMVCAT/CM2+ pACMVtRNARz12, DpnI restricted. Lane 10: 1 ug transfected DNA (time zero), pACMVCAT/CM2 +pACMVtRNARz12, MboI restricted. (14a) CAT: Southern blot of DNA from 3 day old or time zero cells with either DpnI or mboI. Any replicated DNA will be cut with mboI. Band 2 represents CAT/CM2 insert and is maintained in mboI digests signifying replicated DNA. Band 2 is present in equal amounts in Lanes 6 and 10 representing pACMVCAT/CM2 input only and pACMVCAT/CM2+ pACMVtRNARz12 respectively. Band 1 is on input DNA only and is lost in mboI digests. (14b) CATMUT2: Southern blot of DNA from 3 day old or time zero cells with either DpnI or mboI. Any replicated DNA will be cut with mboI. Band 2 represents CAT/CM2 insert and is maintained in mboI digests signifying replicated DNA. Band 2 is present in equal amounts in Lanes 6 and 10 representing pACMVCAT/CM2 input only and pACMVCAT/CM2+ pACMVtRNARz12 respectively. Band 1 is on input DNA only and is lost in mboI digests. This blot doesn't show that lane 1 DNA is completely resistant to mboI digestion.
Figure 14B:
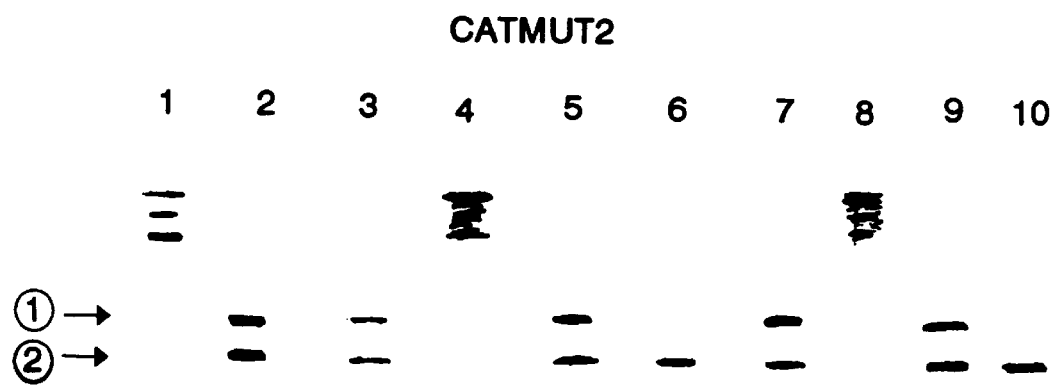

To ensure that the observed reduction in CAT activity was not due to inhibition of replication of the pACMVCAT or pACMVCM2 construct, in the presence of the tRNARz12 ribozyme, DNA was analysed at one and three days post transfection in the presence and absence of the tRNARz12 ribozyme. Methylation sensitive isoschizomers, DpnI and MboI were used to differentiate replicated from input pACMV sequences. As, shown in FIGS. 14a and 14b, both the CAT and CM2 constructs replicate to equivalent levels in the presence or absence of the tRNARz12 construct. Also, all four pACMV expressing ribozyme and antisense constructs replicate. Reduced levels of accumulated CAT mRNA correlate with reduced CAT activity: The effect the ribozymes had on the accumulation of CAT mRNA within the cell was examined using FIGS. 13a and 13b which shows a southern blot of two PCR amplified products derived from total RNA isolated form protoplasts electroporated with CAT target and either of the two antisense or two ribozyme constructs. The blots, which were probed with radiolabelled CAT sequence, show amplification products for both the CAT and CM2 target sequences. The two amplified products represent either full length (primers 1+TAG) or truncated (primers 2+TAG) CAT mRNA. The truncated is derived from amplification of CAT message downstream of the GUC target site and therefore provides an internal control to observe ribozyme mediated cleavage. As shown in Table 10, it was observed that amplification of these two products approximated a 1:1 ratio in the presence of all antisense/ribozyme constructs for the CAT and CM2 targets except in the case of CAT+tRNARz12. For the tRNARz12 ribozyme, the ratio of the downstream product to the full length product was 3.3. That is, the product amplifying downstream of the cleavage site was amplified three times more than the full length product. Amplification has been determined to be in the linear range by carrying out a time course of cycles from 10 through 40 with aliquots removed at 10 cycle intervals (data not shown). With confidence, it may be said that the amplification obtained is representative of the actual amounts of CAT mRNA present within each of the isolated RNA samples.

TABLE 10

Ratio of accumulation of 3' product to full length CAT product. (An explanation of these products is given hereinabove as well as in Figures 13a and 13b which illustrate a southern blot of these products.) The Table below shows the ratio of these products for each of the construct combinations. These ratios are the accumulated data from two independent experiments.

| + | CAT tRNA | tRNA Rz12 | tRNA As24 | Rz12 | As24 |
|---|---|---|---|---|---|
|  | 1.05 | 3.3 | 0.85 | 1.24 | 0.77 |
| + | CM2 tRNA | tRNA Rz12 | tRNA As24 | Rz12 | As24 |
|  | 0.75 | 1.28 | 0.78 | 0.83 | 0.73 |

Discussion

The present invention shows that transfection of tobacco protoplasts with self-replicating vectors expressing both a target sequence, CAT, and a tRNA-embedded ribozyme that is capable of cleaving the CAT message, results in significant reduction in CAT activity. Unlike previous in vivo ribozyme mediated destruction over substrate sequence to the cell [Cameron and Jennings, 1989; Cotten and Birnsteil, 1989; Sioud, et al., 1992; Steinecke, et al., 1992; Perriman, et al., 1993]. The results obtained herein from the internal control, in which the GUC target site on the CAT mRNA has been mutated to a GUG, suggest that the reduction observed for the wildtype CAT sequence is indeed a ribozyme mediated one. That is, the mutant target, CM2, showed an inhibition in the presence of the tRNARz12 sequence comparable to what was observed for antisense constructions, suggesting that the increased reduction observed for the wildtype target is due to the ribozyme cleavage of the CAT mRNA.

This conclusion is also supported from the analysis on the accumulation of CAT mRNA within the electroporated protoplasts. Reverse-transcriptase PCR on RNA obtained from transfected tobacco cells showed that the ratio of the downstream PCR product to the full length product was markedly elevated, demonstrating intracellular cleavage. The ratio of 3.3 reported herein is similar to that obtained by Cantor, et al. 1993] and Dropulic, et al. (1992) in assays using a ribozyme against HIV. While it was possible to observe reduction in full length CAT mRNA, it was not possible to detect cleavage products using an RNase protection assay. Reports on the stability of CAT message suggest that in stably transformed cells, the half-life is around 70 minutes. In transiently transformed cells, the half-life may be shorter [Gallie, et al., 1991]. In considering that the cleavage products would also have elevated susceptibility to exonuclease activity, the chances are low of protecting, and therefore observing intracellular accumulation of cleavage products. Instability of the cleavage products also suggests that the observed ratio for the RT-PCR amplification in the presence of the tRNARz12 ribozyme may be greater than that pertaining, if all cleavage products were detected. Much of the 3' cleavage product, which is represented by the truncated PCR product (primers 2+TAG), once produced intracellularly, is probably rapidly degraded.

Unlike the results of Cotten and Birnsteil (1989), a reduced level of in vitro cleavage by the tRNA-embedded ribozyme over that obtained for the non-embedded ribozyme was observed. Despite this reduced level in vitro, the tRNA-embedded ribozyme presented herein significantly reduced CAT activity in vivo. The tRNA constructions were designed so that two putatively active promoter sequences are present. The first being the endogenous RNA polymerase II based coat protein promoter and the second is the RNA polymerase III promoter internal to the tRNA sequence. Although Cotten and Birnsteil observed reduced transcription of their tRNARz construct over that of the wildtype tRNA sequence, it was noted that no such reductions occurred. The predominant transcript in the chimeric system presented herein was the RNA polymerase III transcript (manuscript in preparation). This is similar to results obtained by Kinsey and Sandemeyer (1991) when delivering tyrosine tRNA to yeast cells containing an upstream RNA polymerase II promoter. Additionally, it was found that processing rates of the tRNARz12 and tRNAAs24 transcripts were comparable to wildtype tRNA in S100 wheat germ extracts (manuscript in preparation). From these results one can concluded that most of the active tRNARz12 transcripts are RNA polymerase III derived.

Demonstration that hammerhead ribozymes can specifically target and cleave specific mRNA sequences in vivo in both plant and animal systems has been limited. While some success has been obtained in delivering single non-embedded ribozymes in animal systems [Sarver, et al., 1990; Droupilic, et al., 1992; L'Huillier, et al., 1992; Cantor, et al., 1993; Zhao, et al., 1993], it is likely that the ribozyme requires additional stabilizing sequence 5' and/or 3' to enable sufficient time to anneal to and cleave the designated target. While Sullenger and Cech (1993) show an enhanced effect of ribozymes when the target and ribozyme are sequestered within the same molecule, this approach is certainly not applicable to many therapeutic situations. This is particularly the case if the target sequence is plant or animal genome derived or of viral origin.

One could believe that tRNA molecules are excellent candidates for enhancing the ribozymes effectiveness in vivo. The results of Cotten and Birnsteil 1989) in Xenopus oocytes combined with the results presented herein on plant cells suggest that a tRNA delivery system has a number of advantages over traditional approaches to gene stability. Firstly, the tRNA is a small and ubiquitous sequence. Secondly, RNA polymerase III may transcribe to high levels within the cell, thus providing us with a means of producing large amounts of the desired transcript. Finally measurements of tRNA stability within plant systems estimate the half-life to be in the order of 45 hours [Karnail and Wasternack, 1992] making them ideal for delivery of ribozyme sequences.

TABLE 1

Cleavage efficiency of helix II stem-length variants.
In Formula 1: $(X)_n$ is 5'-AAAGGGGGAA-3' (SEQ ID NO: 12); $(X)_{n'}$ is 5'-GGGAGCUGGC-3' (SEQ ID NO: 2); $(X)_a$ is absent; $(X)_b$ is 5'-GUGA-3'; 5'-...AXG...-3' is 5'-...AUG...-3';
and $(X)_{m'}$ and $(X)_m$ are given below. See FIG. 1 for Plot.

| | % cleavage products | | | | | | | |
|---|---|---|---|---|---|---|---|---|
| | 0 | 2 | 5 | 10 | 15 | 30 | 60 | 120 min |
| control<br>$(X)_{m'}$ 5'-GUCC-3'<br>$(X)_m$ 5'-GGAC-3'<br>stem length variants | 3 | 15 | 41 | 60 | 72 | 88 | 92 | 94 |
| 1) 2 base pairs<br>$(X)_{m'}$ 5'-GC-3'<br>$(X)_m$ 5'-GC-3' | 4 | 24 | 60 | 68 | 70 | 73 | 76 | |

TABLE 1-continued

Cleavage efficiency of helix II stem-length variants.
In Formula 1: $(X)_n$ is 5'-AAAGGGGGAA-3' (SEQ ID NO: 12); $(X)_{n'}$ is 5'-GGGAGCUGGC-3' (SEQ ID NO: 2); $(X)_a$ is absent; $(X)_b$ is 5'-GUGA-3'; 5'-...AXG...-3' is 5'-...AUG...-3';
and $(X)_{m'}$ and $(X)_m$ are given below. See FIG. 1 for Plot.

| | % cleavage products | | | | | | | |
|---|---|---|---|---|---|---|---|---|
| | 0 | 2 | 5 | 10 | 15 | 30 | 60 | 120 min |
| 2) 3 base pairs<br>$(X)_{m'}$ 5'-GAC-3'<br>$(X)_m$ 5'-GUC-3' | 2 | 36 | 68 | 83 | 88 | 91 | 91 | 93 |
| 3) 3 base pairs<br>$(X)_{m'}$ 5'-GCC-3'<br>$(X)_m$ 5'-GGC-3' | 3 | 26 | 44 | 68 | 69 | 74 | 79 | |
| 4) 4 base pairs<br>$(X)_{m'}$ 5'-GAUC-3'<br>$(X)_m$ 5'-GAUC-3' | 1 | 6 | 15 | 31 | 47 | 68 | 86 | |
| 5) 5 base pairs<br>$(X)_{m'}$ 5'-GAUAC-3'<br>$(X)_m$ 5'-GUAUC-3' | 0 | 3 | 8 | 15 | 23 | 44 | 68 | |
| 6) 6 base pairs<br>$(X)_{m'}$ 5'-GAUAUC-3'<br>$(X)_m$ 5'-GAUAUC-3' | 0 | 3 | 8 | 20 | 32 | 48 | 75 | 69 |
| 7) 7 base pairs<br>$(X)_{m'}$ 5'-GAUAUAC-3'<br>$(X)_m$ 5'-GUAUAUC-3' | 1 | 7 | 15 | 28 | 41 | 67 | 85 | 94 |
| 8) 8 base pairs<br>$(X)_{m'}$ 5'-GAUAUAUC-3'<br>$(X)_m$ 5'-GAUAUAUC-3' | 1 | 6 | 13 | 27 | 38 | 60 | 83 | 91 |
| 9) 3 base pairs<br>$(X)_{m'}$ 5'-GCG-3'<br>$(X)_m$ 5'-CGC-3' | 1 | 29 | 53 | 78 | 82 | 89 | 91 | |

TABLE 2

Cleavage efficiency of helix II conserved G-C base pair.
In Formula 1: $(X)_n$ is 5'-AAAGGGGGAA-3' (SEQ ID NO: 12); $(X)_{n'}$ is 5'-GGGAGCUGGC-3' (SEQ ID NO: 2); $(X)_a$ is absent; $(X)_b$ is 5'-GUGA-3'; 5'-...AXG...-3' is 5'-...AUG...-3'; and $(X)_{m'}$ and $(X)_m$ are given below. See FIG. 2 for Plot.

| | % cleavage products | | | | | | | |
|---|---|---|---|---|---|---|---|---|
| | 0 | 2 | 5 | 10 | 15 | 30 | 60 | 120 min |
| control<br>$(X)_{m'}$ 5'-GUCC-3'<br>$(X)_m$ 5'-GGAC-3'<br>variants of conserved G-C base pair | 3 | 15 | 41 | 60 | 72 | 88 | 92 | 94 |
| 1) A-G<br>$(X)_{m'}$ 5'-GUCC-3'<br>$(X)_m$ 5'-GGAA-3' | 3 | 21 | 39 | 58 | 72 | 85 | 90 | 92 |
| 2) U-A<br>$(X)_{m'}$ 5'-AUCC-3'<br>$(X)_m$ 5'-GGAU-3' | 1 | 7 | 13 | 24 | 35 | 55 | 78 | 88 |
| 3) C-A<br>$(X)_{m'}$ 5'-AUCC-3'<br>$(X)_m$ 5'-GGAC-3' | 0 | 4 | 8 | 16 | 22 | 41 | 58 | 65 |
| 4) C-C<br>$(X)_{m'}$ 5'-CUCC-3'<br>$(X)_m$ 5'-GGAC-3' | 0 | 6 | 8 | — | 20 | 33 | 52 | 66 |
| 5) A-U<br>$(X)_{m'}$ 5'-UUCC-3'<br>$(X)_m$ 5'-GGAA-3' | 0 | 3 | 7 | 12 | 16 | 30 | 51 | 75 |
| 6) U-C<br>$(X)_{m'}$ 5'-CUCC-3'<br>$(X)_m$ 5'-GGAU-3' | 0 | 1 | 3 | 5 | 7 | 13 | 23 | 43 |
| 7) G-A<br>$(X)_{m'}$ 5'-AUCC-3'<br>$(X)_m$ 5'-GGAG-3' | 0 | 1 | 2 | 4 | 6 | 12 | 23 | 40 |

TABLE 2-continued

Cleavage efficiency of helix II conserved G-C base pair.
In Formula 1: $(X)_n$ is 5'-AAAGGGGGAA-3' (SEQ ID NO: 12); $(X)_{n'}$ is 5'-GGGAGCUGGC-3' (SEQ ID NO: 2); $(X)_a$ is absent; $(X)_b$ is 5'-GUGA-3'; 5'-...AXG...-3' is 5'-...AUG...-3'; and $(X)_{m'}$ and $(X)_m$ are given below. See FIG. 2 for Plot.

| | % cleavage products | | | | | | | |
|---|---|---|---|---|---|---|---|---|
| | 0 | 2 | 5 | 10 | 15 | 30 | 60 | 120 min |
| 8) G-U | 0 | 0 | 2 | 3 | 4 | 9 | 15 | 30 |
| $(X)_{m'}$ 5'-UUCC-3' | | | | | | | | |
| $(X)_m$ 5'-GGAG-3' | | | | | | | | |
| 9) U-U | 1 | 5 | 10 | 21 | 25 | 48 | 66 | 80 |
| $(X)_{m'}$ 5'-UUCC-3' | | | | | | | | |
| $(X)_m$ 5'-GGAU-3' | | | | | | | | |
| 10) G-C | | | | | | | | 0 |
| $(X)_{m'}$ 5'-CUCC-3' | | | | | | | | |
| $(X)_m$ 5'-GGAG-3' | | | | | | | | |

TABLE 3

Figure 3A:
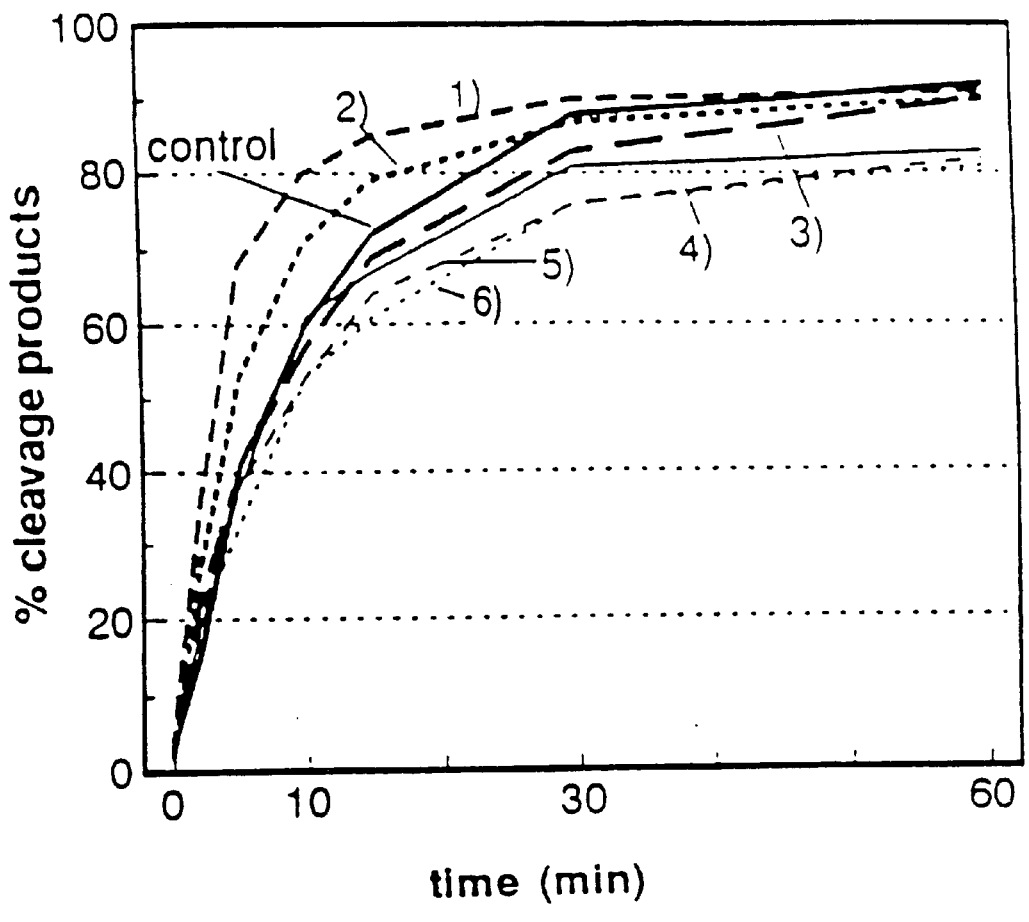
FIGS. 3A–3C. Shows the cleavage efficiency of helix II ($(X)_m$ and $(X)_{m'}$ of formulas 1 and 2) loop variants by plotting % cleavage as a function time in minutes. The data plotted is tabulated in Table 3 and each entry in Table 3 corresponds to each graph in the plot by number.
Figure 3B:
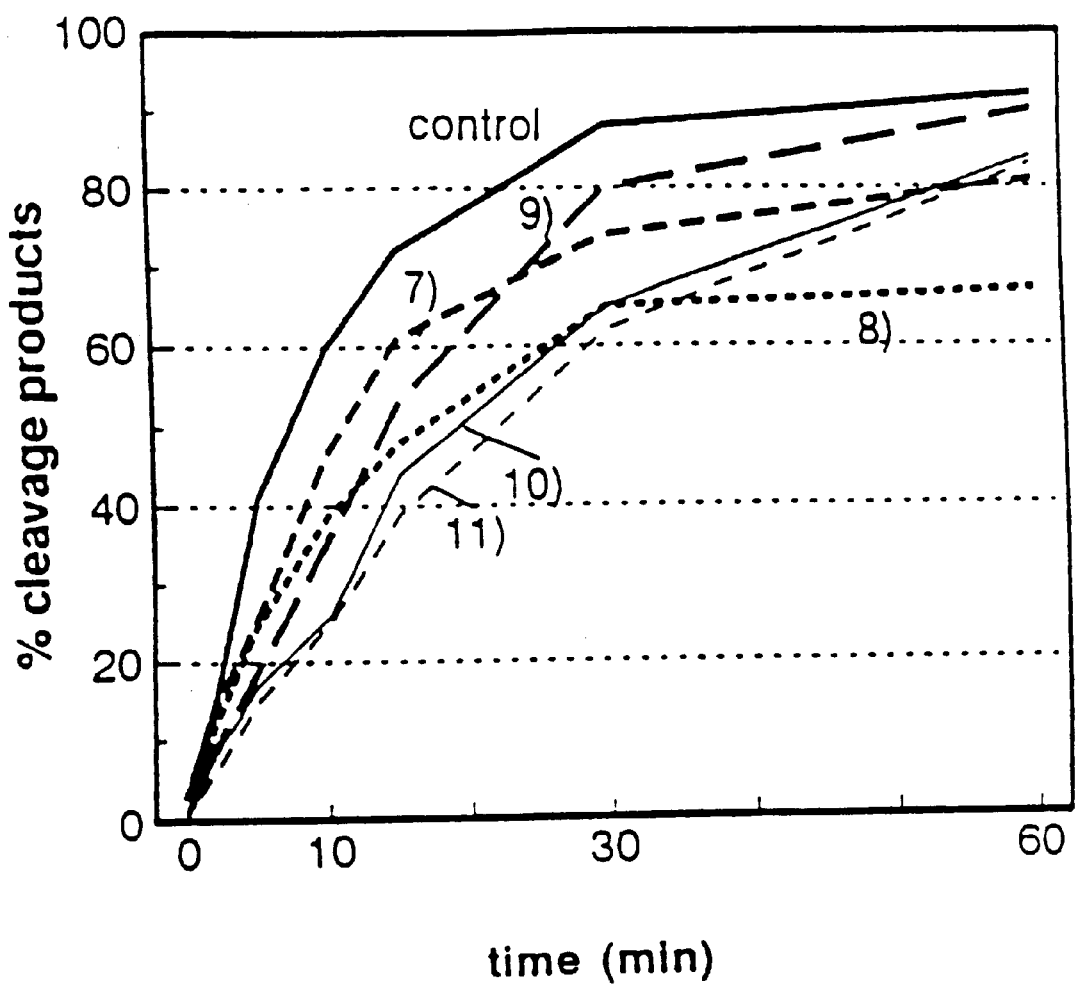
Figure 3C:
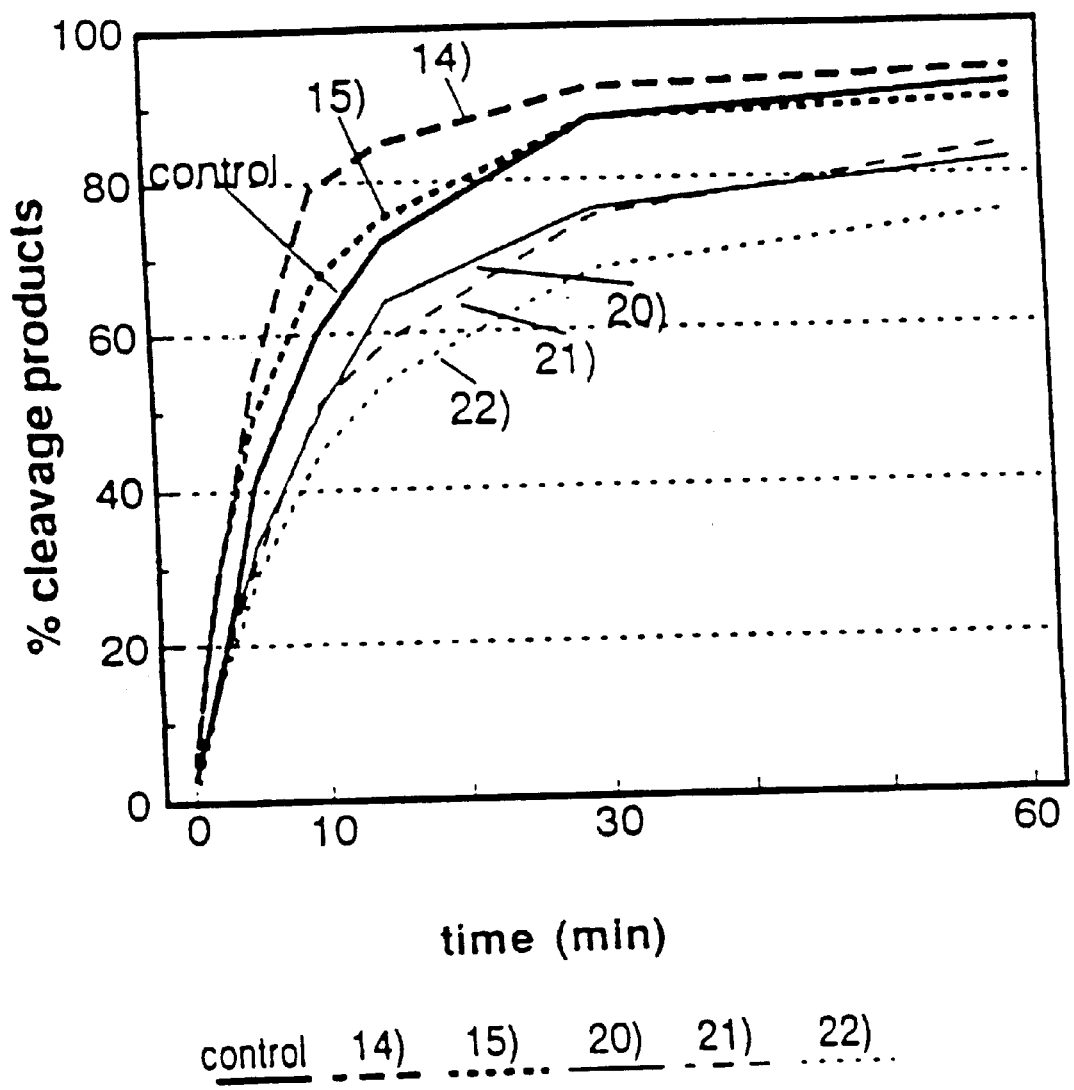

Cleavage efficiency of helix loop variants.
(In Formula 1: $(X)_n$ is 5'-AAAGGGGGAA-3' (SEQ ID NO: 12); $(X)_{n'}$ is 5'-GGGAGCUGGC-3' (SEQ ID NO: 2); $(X)_a$ is absent; $(X)_{m'}$ is 5'-GUCC-3'; $(X)_m$ 5'-GGAC-3'; 5'-...AXG...-3' is 5'-...AUG...-3'; and $(X)_b$ are given below. See FIGS. 3A–3C for Plots.

| | % cleavage products | | | | | | | |
|---|---|---|---|---|---|---|---|---|
| | 0 | 2 | 5 | 10 | 15 | 30 | 60 | 120 min |
| control $(X)_b$ 5'-GUGA-3' | 3 | 15 | 41 | 60 | 72 | 88 | 92 | 94 |
| loop variants | | | | | | | | |
| 1) $(X)_b$ 5'-GGGA-3' | 4 | 36 | 68 | 80 | 85 | 90 | 91 | 93 |
| 2) $(X)_b$ 5'-GUGG-3' | 2 | 27 | 53 | 71 | 79 | 87 | 90 | 92 |
| 3) $(X)_b$ 5'-GUGU-3' | 2 | 23 | 41 | 57 | 69 | 83 | 90 | 91 |
| 4) $(X)_b$ 5'-UGGC-3' | 2 | 19 | 38 | 61 | 67 | 81 | 83 | 86 |
| 5) $(X)_b$ 5'-GGCA-3' | 0 | 21 | 38 | 53 | 64 | 76 | 82 | 85 |
| 6) $(X)_b$ 5'-GUGC-3' | 2 | 19 | 33 | 53 | 61 | 76 | 81 | 88 |
| 7) $(X)_b$ 5'-GUUA-3' | 0 | 14 | 26 | 47 | 61 | 74 | 81 | 83 |
| 8) $(X)_b$ 5'-GGGC-3' | 0 | 12 | 25 | 39 | 48 | 65 | 67 | 74 |
| 9) $(X)_b$ 5'-UCAG-3' | 0 | 9 | 19 | 36 | 53 | 80 | 90 | 92 |
| 10) $(X)_b$ 5'-GACU-3' | 0 | 8 | 17 | 26 | 44 | 65 | 84 | 92 |
| 11) $(X)_b$ 5'-UUCG-3' | 0 | 6 | 15 | 25 | 39 | 62 | 83 | 93 |
| 12) $(X)_b$ 5'-CCGG-3' | | | | | | | | 84 |
| 13) $(X)_b$ 5'-UUUU-3' | | | | | | | | 84 |
| 14) $(X)_b$ 5'-CGGAA-3' | 5 | 28 | 54 | 79 | 85 | 92 | 94 | 96 |
| 15) $(X)_b$ 5'-UUGGA-3' | 5 | 29 | 49 | 67 | 75 | 88 | 90 | 93 |
| 16) $(X)_b$ 5'-GUGUU-3' | | | | | | | | 85 |
| 17) $(X)_b$ 5'-UUCGA-3' | | | | | | | | 84 |
| 18) $(X)_b$ 5'-GGGGU-3' | | | | | | | | 81 |
| 19) $(X)_b$ 5'-GCUUA-3' | | | | | | | | 66 |
| 20) $(X)_b$ 5'-GAC-3' | 3 | 17 | 33 | 50 | 64 | 76 | 82 | 85 |
| 21) $(X)_b$ 5'-GAG-3' | 3 | 16 | 31 | 51 | 59 | 75 | 84 | 88 |
| 22) $(X)_b$ 5'-GUG-3' | 0 | 14 | 29 | 45 | 54 | 68 | 75 | 83 |
| 23) $(X)_b$ 5'-ACA-3' | | | | | | | | 80 |
| 24) $(X)_b$ 5'-UGA-3' | | | | | | | | 77 |
| 25) $(X)_b$ 5'-GCU-3' | | | | | | | | 68 |

TABLE 4

Cleavage efficiency of helix II stem mismatches.
In Formula 1: $(X)_n$ is 5'-AAAGGGGGAA-3' (SEQ ID NO: 12); $(X)_{n'}$ is 5'-GGGAGCUGGC-3' (SEQ ID NO: 2); $(X)_a$ is absent; $(X)_b$ is 5'-GUGA-3'; 5'-...AXG...-3' is 5'-...AUG...-3'; and $(X)_{m'}$ and $(X)_m$ are given below.

| | % cleavage products | | | | | | | |
|---|---|---|---|---|---|---|---|---|
| | 0 | 2 | 5 | 10 | 15 | 30 | 60 | 120 min |
| control | 3 | 15 | 41 | 60 | 72 | 88 | 92 | 94 |
| $(X)_{m'}$ 5'-GUCC-3' | | | | | | | | |
| $(X)_m$ 5'-GGAC-3' | | | | | | | | |
| stem mismatches | | | | | | | | |
| 1) $(X)_{m'}$ 5'-GUCG-3' | 0 | 9 | 28 | 49 | 53 | 65 | 65 | 71 |
| $(X)_m$ 5'-GGAC-3' | | | | | | | | |
| 2) $(X)_{m'}$ 5'-GUCC-3' | 0 | 1 | 2 | 3 | 6 | 8 | 11 | 12 |
| $(X)_m$ 5'-CAAC-3' | | | | | | | | |
| 3) $(X)_{m'}$ 5'-GUCC-3' | | | | | | | | 51 |
| $(X)_m$ 5'-CGAC-3' | | | | | | | | |
| 4) $(X)_{m'}$ 5'-GUCU-3' | | | | | | | 50 | |
| $(X)_m$ 5'-GUAC-3' | | | | | | | | |
| 5) $(X)_{m'}$ 5'-GUCC-3' | | | | | | | 37 | |
| $(X)_m$ 5'-AGAC-3' | | | | | | | | |
| 6) $(X)_{m'}$ 5'-GUCC-3' | | | | | | | 28 | |
| $(X)_m$ 5'-UAAC-3' | | | | | | | | |
| 7) $(X)_{m'}$ 5'-GUCC-3' | | | | | | | 5 | |
| $(X)_m$ 5'-UUAC-3' | | | | | | | | |
| 8) $(X)_{m'}$ 5'-GUCC-3' | | | | | | | 4 | |
| $(X)_m$ 5'-ACAC-3' | | | | | | | | |

TABLE 5

Cleavage efficiency of minizyme variants.
In Formula 1: $(X)_n$ is 5'-AAAGGGGGAA-3' (SEQ ID NO: 12); $(X)_{n'}$ is 5'-GGGAGCUGGC-3'(SEQ ID NO: 2); $(X)_a$ is absent; 5'-...AXG...-3' is 5'-...AUG...-3'; and 5'-$(X)_{m'}$-$(X)_b$-$(X)_m$-3' is given below.

| | % cleavage products | | | | | | | |
|---|---|---|---|---|---|---|---|---|
| | 0 | 2 | 5 | 10 | 15 | 30 | 60 | 120 min |
| control | 3 | 15 | 41 | 60 | 72 | 88 | 92 | 94 |
| $(X)_{m'}$ 5'-GUCC-3' | | | | | | | | |
| $(X)_m$ 5'-GGAC-3' | | | | | | | | |
| $(X)_b$ 5'-GUGA-3' | | | | | | | | |
| minizyme variants | | | | | | | | |
| 5'-$(X)_{m'}$-$(X)_b$-$(X)_m$-3' | | | | | | | | |
| 1) 5'-UUUU-3' | 0 | 0 | 0 | 2 | 6 | 12 | 26 | 48 |
| 2) 5'-UUCG-3' | | | | | | | | 6 |
| 3) 5'-GUGA-3' | | | | | | | | 5 |
| 4) 5'-GGGC-3' | | | | | | | | 1 |
| 5) 5'-UCAG-3' | | | | | | | | 0 |
| 6) 5'-AAAC-3' | | | | | | | | 0 |
| 7) 5'-ACGC-3' | | | | | | | | 0 |

TABLE 6

Figure 6:
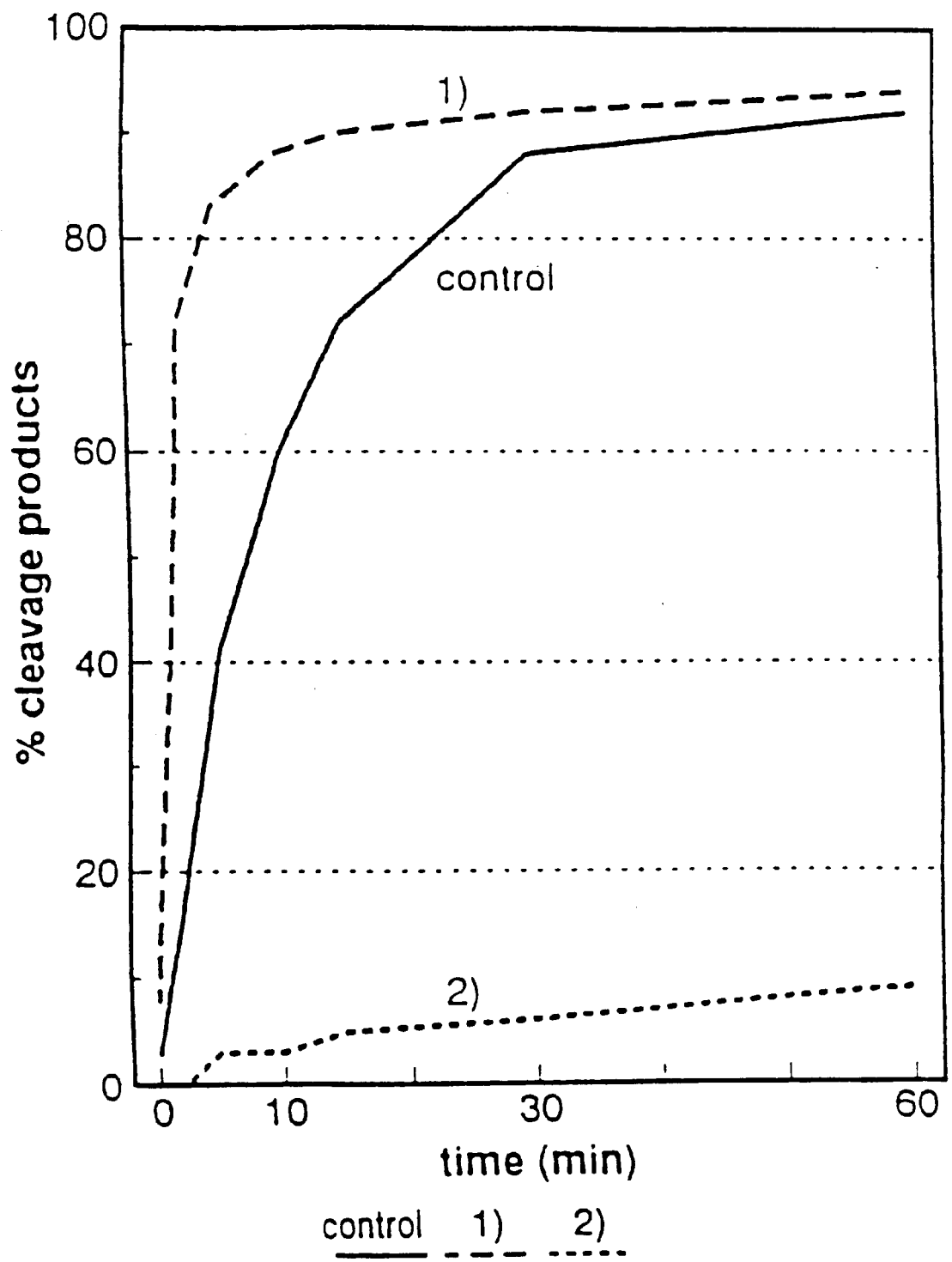
FIG. 6. Shows the cleavage efficiency of helix I ($(X)_{n'}$ of formulas 1 and 2; or —N—N—$(X)_{n'}$ of formula 3) sequence variants by plotting % cleavage as a function time in minutes. The data plotted is tabulated in Table 6 and each entry in Table 6 corresponds to each graph in the plot by number.

Cleavage efficiency of helix I sequence variants.
In Formulas 1, 2, or 3: $(X)_n$ is 5'-AAAGGGGGAA-3' (SEQ ID NO: 12); $(X)_a$ is absent; $(X)_b$ is 5'-GUGA-3'; $(X)_{m'}$ is 5'-GUCC-3'; $(X)_m$ 5'-GGAC-3'; 5'-...AXG...-3' is 5'-...AUG...-3'; and 3'-$(X)_n$-5' or 3'-N-N-$(X)_n$-5' is given below. See FIG. 6 for Plot.

| | % cleavage products | | | | | | | |
|---|---|---|---|---|---|---|---|---|
| | 0 | 2 | 5 | 10 | 15 | 30 | 60 | 120 min |
| control | 3 | 15 | 41 | 60 | 72 | 88 | 92 | 94 |
| substrate helix I: | | | | | | | | |
| 5'-GCCAGCUCCC-3' (SEQ ID NO: 1) | | | | | | | | |
| ribozyme helix I: 3'-$(X)_n$-5' or 3'-N-N-$(X)_n$-5' | | | | | | | | |
| 5'-GGGAGCUGGC-3' (SEQ ID NO: 2) | | | | | | | | |
| ribozyme helix I sequence variants | | | | | | | | |
| 1) 5'-GGUGAGCGGC-3' (SEQ ID NO: 3) | 8 | 72 | 83 | 68 | 90 | 92 | 94 | 95 |
| 2) 5'-GGGAGCUGGU-3' (SEQ ID NO: 4) | 0 | 0 | 3 | 3 | 5 | 6 | 9 | 17 |
| 3) 5'-GGAGCUCUAU-3' (SEQ ID NO: 5) | 0 | 0 | 0 | 0 | 1 | 1 | 2 | 4 |
| 4) 5'-GGUCUGUGGC-3' (SEQ ID NO: 6) | — | 25 | 51 | 66 | 77 | 83 | 88 | |
| 5) 5'-GGGGAUGCGC-3' (SEQ ID NO: 7) | — | 22 | 37 | 64 | 73 | 84 | 90 | 92 |
| 6) 5'-GGACGGUGCC-3' (SEQ ID NO: 8) | — | 2 | 4 | 8 | 11 | 20 | 40 | 61 |
| 7) 5'-GGGAGCUGGA-3' (SEQ ID NO: 9) | | | | | | | 0 | |
| 8) 5'-GGGAGCUGGG-3' (SEQ ID NO: 10) | | | | | | | 0 | |

TABLE 7

Figure 7:
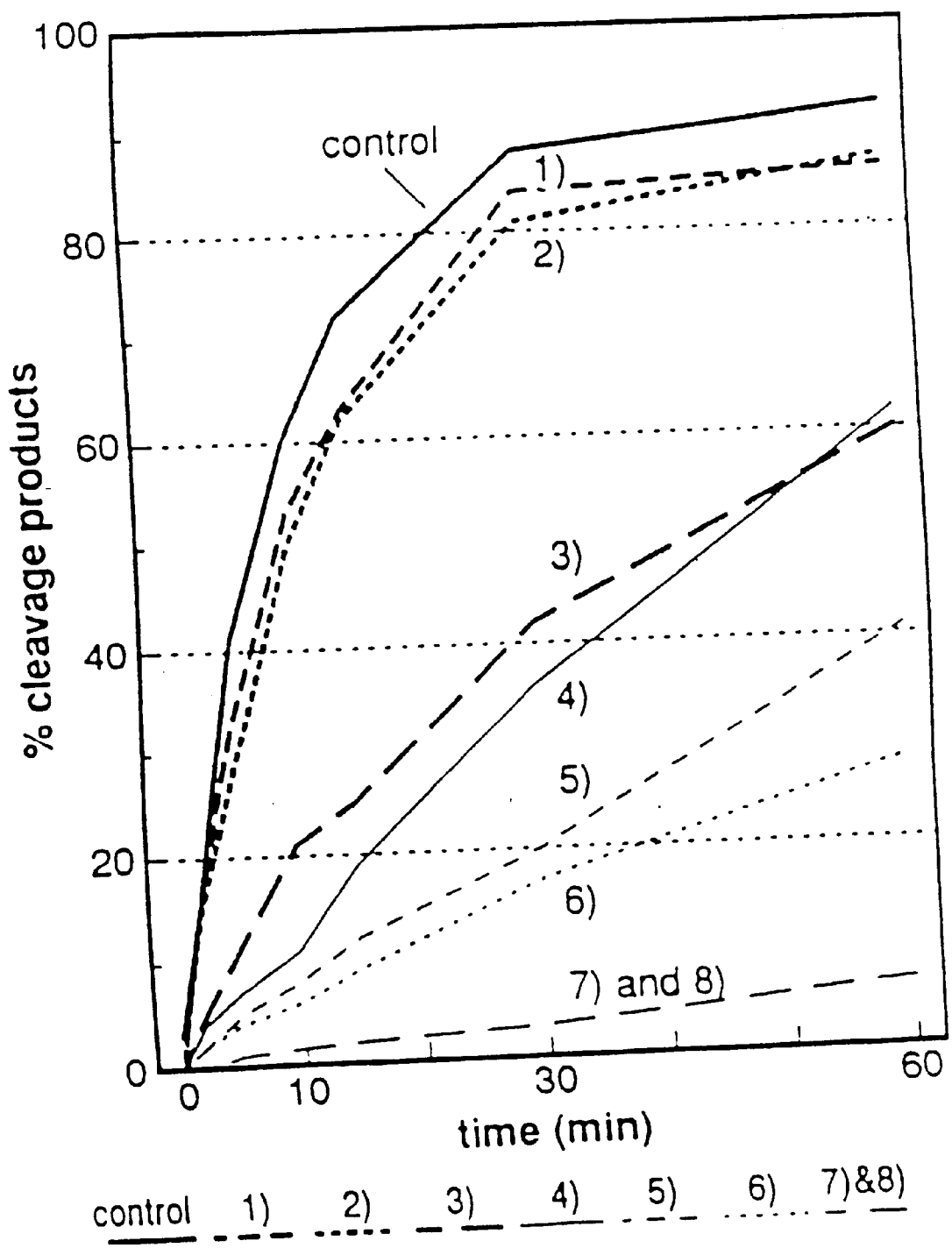
FIG. 7. Shows the cleavage efficiency of helix III ($(X)_n$ of formulas 1 and 2) sequence variants by plotting % cleavage as a function time in minutes. The data plotted is tabulated in Table 7 and each entry in Table 7 corresponds to each graph in the plot by number.

Cleavage efficiency of helix III sequence variants.
In Formula 1: $(X)_{n'}$ is 5'-AAAGGGGGAA-3' (SEQ ID NO: 2); $(X)_a$ is absent; $(X)_b$ is 5'-GUGA-3'; $(X)_{m'}$ is 5'-GUCC-3'; $(X)_m$ 5'-GGAC-3'; 5'-...AXG...-3' is 5'-...AUG...-3'; $(X)_n$ is given below. See FIG. 7 for Plot.

| | % cleavage products | | | | | | | |
|---|---|---|---|---|---|---|---|---|
| | 0 | 2 | 5 | 10 | 15 | 30 | 60 | 120 min |
| control | 3 | 15 | 41 | 60 | 72 | 88 | 92 | 94 |
| substrate helix III | | | | | | | | |
| 5'-UUCCCCCUUU-3' (SEQ ID NO: 11) | | | | | | | | |
| ribozyme helix III: $(X)_n$ | | | | | | | | |
| 5'-AAAGGGGGAA-3' (SEQ ID NO: 12) | | | | | | | | |
| ribozyme helix III sequence variants: $(X)_n$ | | | | | | | | |
| 1) 5'-AAAGUGGAUG-3' (SEQ ID NO: 13) | 1 | 15 | 33 | 53 | 63 | 84 | 86 | 90 |
| 2) 5'-AAGGGGGGAA-3' (SEQ ID NO: 14) | 1 | 14 | 28 | 50 | 62 | 81 | 87 | 89 |
| 3) 5'-AAUUGUGGGA-3' (SEQ ID NO: 15) | 0 | 5 | 11 | 21 | 25 | 42 | 60 | 70 |
| 4) 5'-AAUGGGUGAA-3' (SEQ ID NO: 16) | 0 | 4 | 7 | 11 | 19 | 36 | 62 | 81 |
| 5) 5'-AAUAGGGGAA-3' (SEQ ID NO: 17) | 0 | 2 | 5 | 8 | 12 | 20 | 41 | 64 |
| 6) 5'-ACAGGGGGAA-3' (SEQ ID NO: 18) | 0 | 2 | 4 | 6 | 9 | 17 | 28 | 49 |
| 7) 5'-AAGCGGAGUG-3' (SEQ ID NO: 19) | 0 | 0 | 1 | 2 | 2 | 3 | 6 | 9 |
| 8) 5'-AUAGGGGGAA-3' (SEQ ID NO: 20) | 0 | 0 | 1 | 1 | 2 | 3 | 7 | 12 |
| 9) 5'-AAGGGGGAUA-3' (SEQ ID NO: 21) | 0 | 0 | 0 | 0 | 1 | 2 | 3 | 5 |
| 10) 5'-AAGAUGGGGG-3' (SEQ ID NO: 22) | 0 | 0 | 0 | 0 | 0 | 1 | 1 | |
| 11) 5'-CAAGGGGGAA-3' (SEQ ID NO: 23) | | | | | | | 0 | |

TABLE 8

Figure 8:
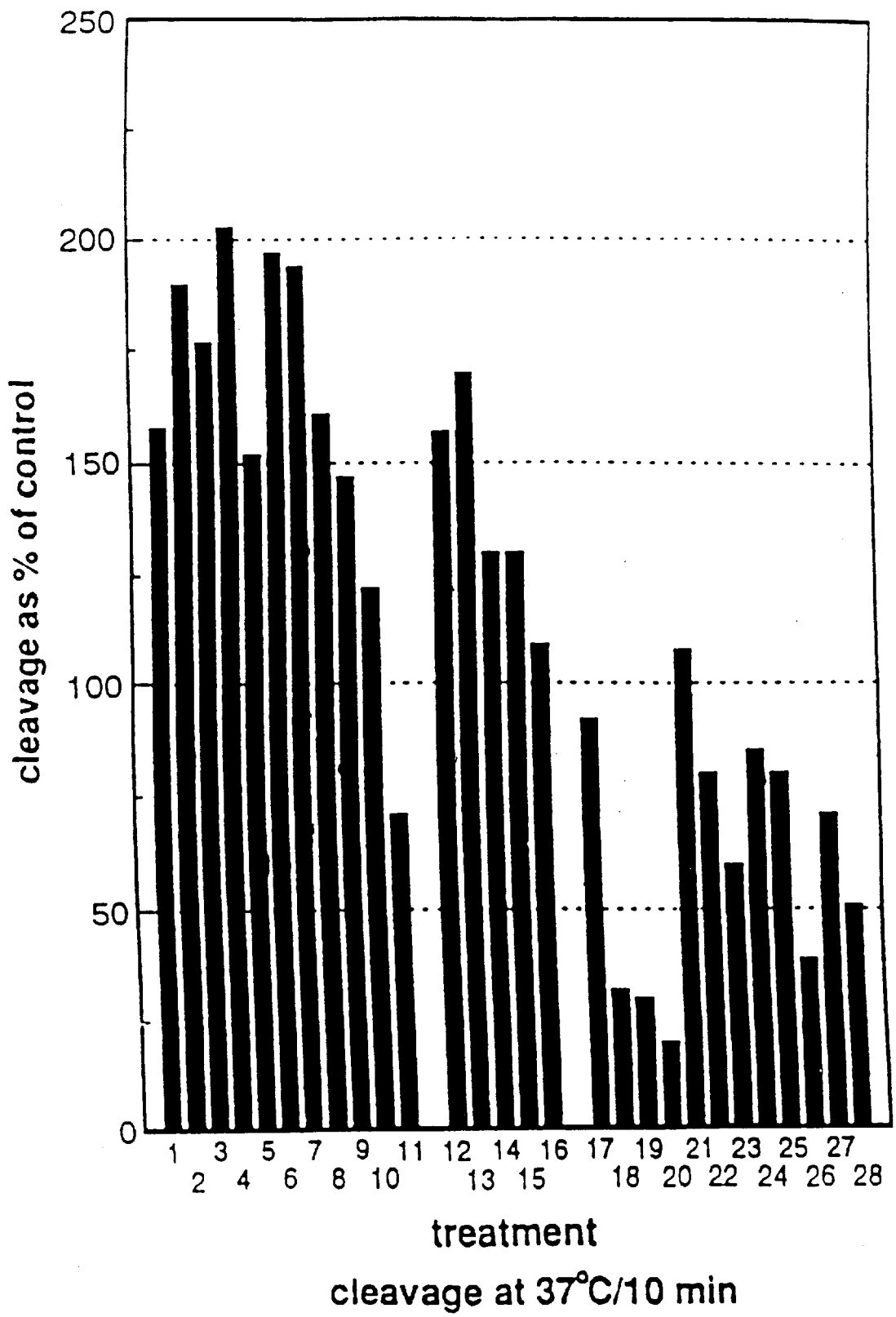
FIG. 8. Shows the effect of oligonucleotides, complementary to the ribozyme, on cleavage efficiency by plotting cleavage as % of control verses a 10 minute interval. The data plotted is tabulated in Table 8 and each entry in Table 8 corresponds to each graph in the plot by number.

Effect of oligonucleotides, complementary to the ribozyme, on cleavage efficiency.
(In Formula 1; $(X)_n$ is 5'-AAAGGGGGAA-3' (SEQ ID NO: 12), $(X)_{n'}$ is 5'-GGGAGCUGGC-3' (SEQ ID NO: 2), $(X)_a$ is absent, $(X)_b$ is 5'-GUGA-3', $(X)_{m'}$ is 5'-GUCC-3', $(X)_m$ 5'-GGAC-3', and 5'-...AXG...-3' is 5'-...AUG...-3'). See FIG. 8 for Plot.

| Complementary Oligonucleotide | cleavage as % of control (37° C./10 min) |
|---|---|
| 1) 5'-dCCCCCTTT-3' | 158 |
| 2) 5'-dTTTTCGTC-3' | 190 |
| 3) 5'-dCTCATCAG-3' | 177 |
| 4) 5'-dGCCAGCTC-3' | 203 |
| 5) 5'-dTTCCCCCTTT-3' (SEQ ID NO: 24) | 152 |
| 6) 5'-dCCCTTTTTCG-3' (SEQ ID NO: 25) | 197 |

TABLE 8-continued

Effect of oligonucleotides, complementary to the ribozyme, on cleavage efficiency.
(In Formula 1; $(X)_n$ is 5'-AAAGGGGGAA-3' (SEQ ID NO: 12), $(X)_{n'}$ is 5'-GGGAGCUGGC-3' (SEQ ID NO: 2), $(X)_a$ is absent, $(X)_b$ is 5'-GUGA-3' , $(X)_{m'}$ is 5'-GUCC-3' , $(X)_m$ 5'-GGAC-3' , and 5'-...AXG...-3' is 5'-...AUG....-3' ). See FIG. 8 for Plot.

|  | cleavage as % of control (37° C./10 min) |
|---|---|
| 7) 5'-dTCAGGCCAG-3' (SEQ ID NO: 26) | 194 |
| 8) 5'-dGCCAGCTCCC-3' (SEQ ID NO: 27) | 161 |
| 9) 5'-dNNNNNNNNNT-3' (SEQ ID NO: 31) (N = dA, dC, dG or dT) | 147 |
| 10) 5'-dAGGCCAGCTCCC-3' (SEQ ID NO: 28) | 122 |
| 11) 5'-dTTCCCCCTTTTTTG-3' (SEQ ID NO: 29) | 71 |
| 12) 5'-CUUUUCG-3' | 157 |
| 13) 5'-GCCAGC-3' | 170 |
| 14) 5'-GGCCAGCU-3' | 130 |
| 15) 5'-AGGCCAGCUC-3' (SEQ. ID NO. 30) | 130 |
| 16) 5'-NNNNNNNG-3' (N = A, C, G or U) | 109 |
| 17) 0.1 mM dATP, dCTP, dGTP, dTTP | 92 |
| 18) 5 mM spermine | 32 |
| 19) 10 mM spermine | 30 |
| 20) 50 mM spermine | 20 |
| 21) 5% polyethylene glycol 8000 | 108 |
| 22) 10% polyethylene glycol 6000 | 80 |
| 23) 15% polyethylene glycol 8000 | 60 |
| 24) 0.5M urea | 85 |
| 25) 1M urea | 80 |
| 26) 3M urea | 39 |
| 27) 10% formamide | 71 |
| 28) 20% formamide | 51 |

REFERENCES

Altman, S. (1987) *Adv. Enzyvmol.* 62:1.
Baer, M. F., et al. (1990) *Methods Enzymol.* 181:569.
Been, M. D., and Cech, T. R. (1988) *Science* 239:1412
Biou, V. et al. (1994) *Science* 263:1404–1410.
Boehm, S., (1987) *FEBS Letters,* 220: 283–287.
Bruening, G., (1989) *Methods in Enzymology,* 180:546–558.
Bruening, G. (1990) *Seminars in Virol.* 1:127.
Bryant, J. (1992) *Tibtech* 10:342–343.
Buzayan et al., (1986) *Proc. Natl. Acad. Sci. USA* 83:8859–8862.
Cameron et al., (1989) *Proc. Natl. Acad. Sci. USA,* 86:9139–9143.
Cantor, G. H., et al. (1993) *Proc. Natl. Acad. Sci. U.S.A.* 90:10932–10936.
Carruthers et al. (1987) *Methods in Enzymology,* 154: 287–313).
Castanotto, D., et al. (1992) *Critical Rev. in Eukaryotic gene Exp.* 2:331–337.
Cech, T. R., (1987) *Science.* 236: 1532–1539.
Cech, T. R., et al. (1981) *Cell* 27:487.
Cheong, C. et al. (1990) *Nature* 346:680–682.
Chuat, J. et al., (1989) *Biochemical and Biophysical Research Communications,* 162: 1025–1029.
Cotten, M., (1990) *Tibtech* 8: 174–178.
Cotten, M. et al., (1989) *The EMBO Journal,* 8: 3861–3866.
Dahm, S. C., et al., (1990) *Biochimie* 72:819–823.
Dropulic, B., et al. (1992) *J. Virol.* 66:1432–1441.
Eckner, R. et al., (1991) *The EMBO Journal,* 10: 3513–3522.
Epstein, L. M., and Gall, J. G., (1987) *Cell* 48:535.
Epstein, L. M., and Gall, J. G., (1989) *Cold Spring Harbour Symp. Quant. Biol.* 52:261.
Evans, G. J., et al. (1992) *Biochem. Soc. Trans.* 20:344S.
Foehler et al. (1986) *Nucleic Acids Research* 14: 5399–407.
Forster et al., (1987) *Cell,* 50:9–16.
Forster, A. C. et al., (1988) *Nature,* 334:265–267.
Forster, A. C. and Symons, R. H., (1987) *Cell,* 49: 211–220.
Freier, S. M. et al. (1986) *Proc. Nat. Acad. Sci. USA* 83:9373–9377.
Friedman, T., (1989) *Science* 244: 1275–1280.
Gallie, D. R., et al. (1991) *Mol. Gen. Genet.* 228:258–264.
Goodchild, J., et al., (1991) *Archives to Biochem & Biophys.* 284:386–391.
Green, R., and Szostak, J. W. (1992) *Science* 258:1910.
Goodchild, J. et al., (1990) Poster No. 12 at Conf in San Diego.
Haseloff, J. and W. L. Gerlach, (1988) *Nature,* 334:585–591.
Haseloff et al., (1989), *Gene,* 82:43–52.
Herschlag, D., and Cech, T. R. (1990) *Nature* 344:405.
Hertel, K. J. et al. (1992) *Nucleic Acids Res.* 20:3252.
Heus, H. A. et al. (1991) *Science* 253:191–194.
Hogan, B. et al., (1986) Manipulating the Mouse Embryo, A Laboratory Manual, Cold Spring Harbor.
Hogan, B. et al., (1989) *Science,* 244: 1275.
Homann, M., et al. (1993) *Nucleic Acid Res.* 28:2809–2814.
Howard, E. A., et al. (1987) *Planta* 170:535–540.
Huillier, A. et al., Ribozyme Mediated Suppression of Lactalbumin Expressed in C1271 Cells by T7/Vaccinia Virus, (Abstract from conference proceedings).
Hutchins, C. J. et al., (1986) *Nucleic Acids Res.* 14:3627–3635.
Jefferies, A. C., et al., (1989) *Nucleic Acids Res.* 17:1371–1377.
Joyce, G. F. (1992) *Sci. Am.* 267:90.
Karnail, U. and Wasternack, C. (1992) *J. Biochem.* 24:493–497.
Kikuchi, Y. et al., (1991) *Nucleic Acids Res.* 19:6751–6755.
Kinsey, P. T. and Sandmeyer, S. S. (1991) *Nucleic Acid Res.* 19:1317–1324.
Koizumi et al., (1988) *FEBS Letters,* 228:228–230.
Koizumi et al., (1989) *Nucleic Acids Res.* 17:7059–7071.
Kruger, K., et al. (1982) *Cell* 31:147.
Kunkel, T. A., et al. (1987) *Methods in Enzymology* 154:367–382.
Lamb, J. W. & Hay, R. T., (1990) *J. Gen. Virol.,* 71:2257–2264.
L'Huillier, P. J. L., et al. (1992) *The EMBO J.* 11:4411–4418.
Llewellyn et al., (1987), *J. Mol. Biol.,* 195: 115–123.
Long, D. M. et al. (1994) *Proc. Natl. Acad. Sci. U.S.A.* 91:6977–6981.
Maliga, P. (1993) *Tibtech* 11:101–106.
Mazzolini, L., et al. (1992) *Plant Molecular Biology* 20:715–731.
McCall, M. J. et al. (1992) *Proc. Natl. Acad. Sci. U.S.A.* 89:5710–5714.
McClain et al., (1987) *Science* 238:527–530.
Miller, W. A. et al., (1991) *Virology,* 183:711–720.
Nichols, M., et al. (1988) *Proc. Natl. Acad. Sci. U.S.A.* 85:1379.
Noller, H. F., et al. (1992) *Science* 256:1416.
Pace, N. R., and Smith, D., (1990) *J. Biol. Chem.* 265:3587.
Pan, T., and Uhlenbeck, O. C. (1992) *Nature* 358:560.
Perriman et al., (1992), *Gene,* 113:157.
Perriman, R., et al. (1993) *Antisense Res. & Dev.* 3:253–263.
Perreault et al., (1990), *Nature,* 344:565–567.
Perreault, J. P., et al., (1991) *Biochem.* 30:4020–4025.
Piccirilli, J. A., et al. (1992) *Science* 256:1420.
Pley, H. W., et al. (1994 A) *Nature* 372:68–74.
Pley, H. W., et al. (1994 B) *Nature* 372:111–113.

Prody et al., (1986), *Science* 231: 1577–1580.
Pyle, A. M. (1993) *Science* 261:709–714.
Robertson, D. L., and Joyce, G. F. (1990) *Nature* 344:467.
Ruffner, D. E. et al., (1990) *Biochemistry*, 29: 10695–10702.
Ruffner, D. E. et al., (1989) *Gene*, 82:31–41.
Sambrook, J. et al., (1989), Molecular Cloning, A laboratory Manual, 2nd Edition, Cold Spring Harbor Press.
Sampson, et al., (1987) Cold Spring Harbor Sym Quant. Biol. 52:267–275.
Sangar, W. (1984), Principles of Nucleic Acid Structure, Springer-Verlag, N.Y.
Sarver, N. et al., (1990) *Science*, 247:1222–1224.
Saville, B. J. and Collins, R. A. (1990) *Cell* 61:685.
Saxena, S. et al., (1990) *J. Biol. Chem.*, 265:17106–17109.
Scanlon, K. et al., (1991) *Proc. Natl. Acad. Sci. USA*, 88:10591–10595.
Sheldon, C. C. & Symons, R. H., (1989) *Nucleic Acids Res.* 17:5679–5686.
Sheldon, C. C. & Symons, R. H., (1989) *Nucleic Acids Res.* 17:5665–5678.
Shimamoto, K., Terada, R., Izawa, T., and Fujimoto, H. (1989) *Nature* 338:274–276.
Sioud, M. and Drlica, K. (1991) *Proc. Natl. Acad. Sci. U.S.A.* 88:7303–7307.
Sioud, M., et al. (1992) *J. Mol. Biol.* 223:831–835.
Strobel, S. A. et al., (1991) *Nature* 350: 172–174 and references therein.
Sober, H. (1970), CRC Handbook of Biochemistry, Second edition.
Sprout et al. (Oligonucleotide Synthesis—A Practical Approach, IRL Press, Oxford (1984) M. J. Gait—Editor, pp. 83–115).
Sullenger, B. A. and Cech, T. R. (1993) *Science* 262:1566–1569.
Stange, N. and Beier, D. (1986) *Nucleic Acid Res.* 14:8961.
Steinecke, P., et al. (1992) *The EMBO J.* 11:1525–1530.
Symons, R. H., (1989) *TIBS*, 14:445–450.
Symons, R. H., (1990) *Seminars in Virol.* 1:117.
Tabler, M. & Tsagris, M., (1991) *Gene*, 108:175–183.
Taylor, J., (1990) *Seminars in Virol.* 1:135.
Tuschl, T. et al. (1993) *Proc. Nat. Acad. Sci. USA* 90:6991–6994.
Uhlenbeck et al., (1987) *Nature*, 328:596–600.
Uhlmann et al., (1990), *Chem. Revs.*, 90:544–584.
Waugh, D. S., et al. (1989) Science 244:1569.
Woese, C. R. et al. (1990) *Proc. Nat. Acad. Sci. USA* 90:8467–8471.
Yang, et al., (1990) *Biochemistry* 29:11156–11160.
Zaug, A. J. et al, (1984), *Science*, 224:574–578
Zaug, A. J. & Cech, T. R., (1986a), *Science*, 231:473–474.
Zaug, A. J. et al., (1986b) *Nature*, 324:429–433.
Zaug, A. J., and Cech, T. R. (1986) *Biochemistry* 25:4478.
Zhao, J. J. and Pick, L. (1993) *Nature* 365:448–451.

What is claimed is:

1. A composition comprising a first synthetic non-naturally occurring oligonucleotide compound which compound comprises nucleotides whose sequence defines a conserved catalytic region and nucleotides whose sequence hybridizes with a predetermined target sequence and a second synthetic non-naturally occurring oligonucleotide compound which does not contain the predetermined target sequence and is complementary to at least a portion of the first oligonucleotide compound, wherein the first synthetic non-naturally occurring oligonucleotide compound has the structure:

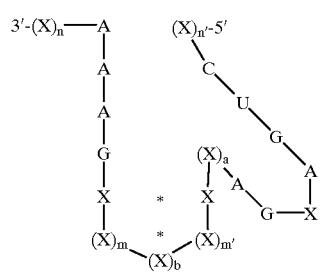

wherein each X represents a nucleotide which is the same or different and may be modified or substituted in its sugar, phosphate or base;

wherein each of A, C, U, and G represents a ribonucleotide which may be unmodified or modified or substituted in its sugar, phosphate or base;

wherein 3'—AAG . . . AGUCX—5' defines a conserved catalytic region;

wherein each of $(X)_nA$ and $(X)_{n'}$ represents an oligonucleotide having a predetermined sequence which hybridizes with an RNA target sequence, and does not naturally occur covalently bound to the sequences 3'-A-A-G-5' and 5'-C-U-G-A-3', respectively, such RNA target sequence not being present within the compound;

wherein each * represents base pairing between the nucleotides located on either side thereof;

wherein each solid line represents a chemical linkage providing covalent bonds between the nucleotides located on either side thereof;

wherein a represents an integer which defines a number of nucleotides with the proviso that a may be 0 or 1 and if 0, the A located 5' of $(X)_a$ is bonded to the X located 3' of $(X)_a$;

wherein each of m and m' represents an integer which is greater than or equal to 1; and wherein $(X)_b$ represents an oligonucleotide and b represents an integer which is greater than or equal to 4.

2. A composition comprising a first synthetic non-naturally occurring oligonucleotide compound which compound comprises nucleotides whose sequence defines a conserved catalytic reaction and nucleotides whose sequence hybridizes with a predetermined target sequence and a second synthetic non-naturally occurring oligonucleotide compound which does not contain the predetermined target sequence and is complementary to at least a portion of the first compound, wherein the first synthetic non-naturally occurring oligonucleotide compound has the structure:

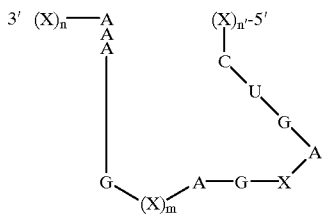

wherein each X is the same or different and represents a ribonucleotide or a deoxyribonucleotide which may be modified or substituted in its sugar, phosphate or base;

wherein each of A, C, U, and G represents a ribonucleotide which may be unmodified or modified or substituted in its sugar, phosphate or base;

wherein 3'—AAG . . . AGUCX—5' defines a conserved catalytic region;

wherein each of $(X)_nA$ and $(X)_{n'}$ represents an oligonucleotide having a predetermined sequence which hybridizes with an RNA target sequence, and does not naturally occur covalently bound to the sequences 3'-A-A-G-5' and 5'-C-U-G-A-3', respectively, such RNA target sequence not being present within the compound;

wherein each solid line represents a chemical linkage providing covalent bonds between the nucleotides located on either side thereof;

wherein m represents an integer from 2 to 20; and wherein none of the nucleotides $(X)m$ are Watson-Crick base paired to any other nucleotide within the compound.

3. A composition comprising a first synthetic non-naturally occurring oligonucleotide compound which compound comprises nucleotides whose sequence defines a conserved region and nucleotides whose sequence hybridizes with a predetermined target sequence and a second synthetic non-naturally occurring oligonucleotide compound which does not contain the predetermined target sequence and is complementary to at least a portion of the first compound, wherein the first synthetic non-naturally occurring oligonucleotide compound has the structure:

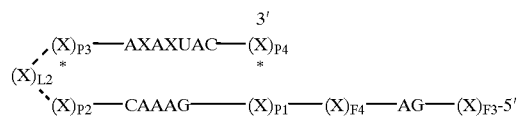

wherein each X is the same or different and represents a ribonucleotide or a deoxyribonucleotide which may be modified or substituted in its sugar, phosphate or base;

wherein each of A, C, U, and G represents a ribonucleotide which may be modified or substituted in its sugar, phosphate or base;

wherein $3'(X)_{P4} \ldots (X)_{P1}$—5' defines a conserved region;

wherein each of $(X)_{F4}$ and $(X)_{F3}$ represents an oligonucleotide having a predetermined sequence which hybridizes with an RNA target sequence;

wherein F3 represents an integer which defines the number of nucleotides in the oligonucleotide with the proviso that F3 is greater than or equal to 3;

wherein F4 represents an integer which defines the number of nucleotides in the oligonucleotide with the proviso that F4 is from 3 to 5;

wherein each of $(X)_{P1}$ and $(X)_{P4}$ represents an oligonucleotide having a predetermined sequence such that $(X)_{P4}$ base-pairs with 3–6 bases of $(X)_{P1}$;

wherein P1 represents an integer which defines the number of nucleotides in the oligonucleotide with the proviso that P1 is from 3 to 6 and the sum of P1 and F4 equals 9;

wherein each of $(X)_{P2}$ and $(X)_{P3}$ represents an oligonucleotide having a predetermined sequence such that $(X)_{P2}$ base-pairs with at least 3 bases of $(X)_{P3}$;

wherein each * represents base pairing between the nucleotides located on either side thereof;

wherein each solid line represents a covalent bond between the nucleotides located on either side thereof;

wherein each of the dashed lines independently represents either a covalent bond between the nucleotides located on either side thereof or the absence of any such bond; and wherein $(X)_{L2}$ represents an oligonucleotide which may be present or absent with the proviso that L2 represents an integer which is greater than or equal to 3 if $(X)_{L2}$ is present.

4. A compound having the formula:

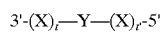

wherein each $(X)_t$ and $(X)_{t'}$ represents an oligonucleotide having a sequence which corresponds to a portion of a tyrosine tRNA molecule of *Nicotiana rustica;* wherein each of t and t' represents an integer which defines the number of nucleotides in the oligonucleotide with the proviso that the sum of t+t' is greater than 50; and wherein Y is an oligonucleotide moiety having the structure:

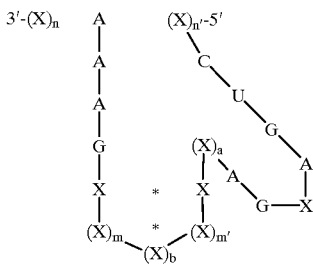

wherein each X represents a nucleotide which is the same or different and may be modified or substituted in its sugar, phosphate or base;

wherein each of A, C, U, and G represents a ribonucleotide which may be unmodified or modified or substituted in its sugar, phosphate or base;

wherein 3'—AAG . . . AGUCX—5' defines a conserved region;

wherein each of $(X)_nA$ and $(X)_{n'}$ represents an oligonucleotide having a predetermined sequence which hybridizes with an RNA target sequence, and does not naturally occur covalently bound to the sequences 3'-A-A-G-5' and 5'-C-U-G-A-3', respectively, such RNA target sequence not being present within the compound;

wherein each * represents base pairing between the nucleotides located on either side thereof;

wherein each solid line represents a covalent bond between the nucleotides located on either side thereof;

wherein a represents an integer which defines a number of nucleotides with the proviso that a may be 0 or 1 and if 0, the A located 5' of $(X)_a$ is bonded to the X located 3' of $(X)_a$;

wherein each of m and m' represents an integer which is greater than or equal to 1; and wherein $(X)_b$ represents an oligonucleotide and b represents an integer which is greater than or equal to 4.

5. The compound of claim 4, wherein the oligonucleotides $(X)_t$ and $(X)_{t'}$ are derived from a tyrosine tRNA molecule of *Nicotiana rustica*.

6. An oligonucleotide transfer vector containing a nucleotide sequence which on transcription gives rise to the compound of claim 4.

7. The transfer vector of claim 6, wherein the transfer vector is selected from a group consisting of a bacterial plasmid, a bacteriophage DNA, a cosmid, and plant viral DNA.

8. The transfer vector of claim 7, wherein the transfer vector comprises the promoter sequences for RNA polymerase II or RNA polymerase III.

9. A host cell transformed by the transfer vector of claim 7.

10. The host cell of claim 9, wherein the host cell is a prokaryotic host cell or an eukaryotic host cell.

11. The prokaryotic host cell of claim 10, wherein the prokaryotic host cell is an *E. coli* host cell.

12. The eukaryotic host cell of claim 10, wherein the eukaryotic host cell is a monkey COS host cell, a Chinese hamster ovary host cell, a mammalian host cell, a plant host cell or a plant protoplast host cell.

13. A packaged oligonucleotide transfer vector containing a nucleotide sequence which on transcription gives rise to the compound of claim 4.

14. The packaged oligonucleotide transfer vector of claim 13, wherein the packaged oligonucleotide transfer vector is a plant DNA virus, a geminivirus or an infective phage particle.

15. The packaged oligonucleotide transfer vector of claim 14, wherein the packaged oligonucleotide transfer vector contains the promoter sequences for RNA polymerase II or RNA polymerase III.

16. A compound having the formula:

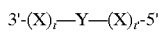

wherein each $(X)_t$ and $(X)_{t'}$ represents an oligonucleotide having a sequence which corresponds to a portion of a tyrosine tRNA molecule of *Nicotiana rustica*;

wherein each of t and t' represents an integer which defines the number of nucleotides in the oligonucleotide with the proviso that the sum of t+t' is greater than 50; and wherein Y is an oligonucleotide moiety having the structure:

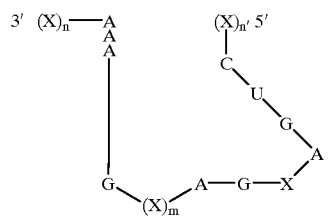

wherein each X is the same or different and represents a ribonucleotide or a deoxyribonucleotide which may be modified or substituted in its sugar, phosphate or base;

wherein each of A, C, U, and G represents a ribonucleotide which may be unmodified or modified or substituted in its sugar, phosphate or base;

wherein 3'—AAG . . . AGUCX—5' defines a conserved region;

wherein each of $(X)_nA$ and $(X)_{n'}$ represents an oligonucleotide having a predetermined sequence which hybridizes with an RNA target sequence, and does not naturally occur covalently bound to the sequences 3'-A-A-G-5' and 5'-C-U-G-A-3', respectively, such RNA target sequence not being present within the compound;

wherein each solid line represents a covalent bond between the nucleotides located on either side thereof;

wherein m represents an integer from 2 to 20; and wherein none of the nucleotides $(X)_m$ are Watson-Crick base paired to any other nucleotide within the compound.

17. The compound of claim 16, wherein the oligonucleotides $(X)_t$ and $(X)_{t'}$ are derived from a tyrosine tRNA molecule of *Nicotiana rustica*.

18. A oligonucleotide transfer vector containing a nucleotide sequence which on transcription gives rise to the compound of claim 16.

19. The transfer vector of claim 18, wherein the transfer vector is selected from a group consisting of a bacterial plasmid, a bacteriophage DNA, a cosmid, and plant viral DNA.

20. The transfer vector of claim 19, wherein the transfer vector comprises the promoter sequences for RNA polymerase II or RNA polymerase III.

21. A host cell transformed by the transfer vector of claim 19.

22. The host cell of claim 21, wherein the host cell is a prokaryotic host cell or an eukaryotic host cell.

23. The prokaryotic host cell of claim 22, wherein the prokaryotic host cell is an *E. coli* host cell.

24. The eukaryotic host cell of claim 22, wherein the eukaryotic host cell is selected from the group consisting of a monkey COS host cell, a Chinese hamster ovary host cell, a mammalian host cell, a plant host cell and a plant protoplast host cell.

25. A packaged oligonucleotide transfer vector containing a nucleotide sequence which on transcription gives rise to the compound of claim 16.

26. The packaged oligonucleotide transfer vector of claim 25, wherein the packaged oligonucleotide transfer vector is a plant DNA virus, a gemini virus or an infective phage particle.

27. The packaged oligonucleotide transfer vector of claim 26, wherein the packaged oligonucleotide transfer vector contains the promoter sequences for RNA polymerase II or RNA polymerase III.

28. A compound having the formula:

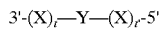

3'-(X)$_t$—Y—(X)$_{t'}$-5' wherein each (X)$_t$ and (X)$_{t'}$ represents an oligonucleotide having a sequence which corresponds to a portion of a plant tRNA molecule;

wherein each of t and t' represents an integer which defines the number of nucleotides in the oligonucleotide with the proviso that the sum of t+t' is greater than 50; and wherein Y is an oligonucleotide moiety having the structure:

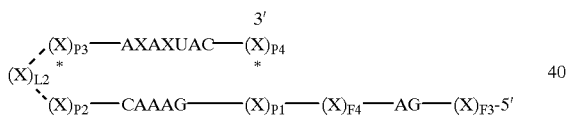

wherein each X is the same or different and represents a ribonucleotide or a deoxyribonucleotide which may be modified or substituted in its sugar, phosphate or base;

wherein each of A, C, U, and G represents a ribonucleotide which may be unmodified or modified or substituted in its sugar, phosphate or base;

wherein 3'(X)$_{P4}$ . . . (X)$_{P1}$—5' defines a conserved region;

wherein each of (X)$_{F4}$ and (X)$_{F3}$ represents an oligonucleotide having a predetermined sequence which hybridizes with an RNA target sequence;

wherein F3 represents an integer which defines the number of nucleotides in the oligonucleotide with the proviso that F3 is greater than or equal to 3;

wherein F4 represents an integer which defines the number of nucleotides in the oligonucleotide with the proviso that F4 is from 3 to 5;

wherein each of (X)$_{P1}$ and (X)$_{P4}$ represents an oligonucleotide having a predetermined sequence such that (X)$_{P4}$ base-pairs with 3–6 bases of (X)$_{P1}$;

wherein P1 represents an integer which defines the number of nucleotides in the oligonucleotide with the proviso that P1 is from 3 to 6 and the sum of P1 and F4 equals 9;

wherein each of (X)$_{P2}$ and (X)$_{P3}$ represents an oligonucleotide having a predetermined sequence such that (X)$_{P2}$ base-pairs with at least 3 bases of (X)$_{P3}$;

wherein each * represents base pairing between the nucleotides located on either side thereof;

wherein each solid line represents a covalent bond between the nucleotides located on either side thereof;

wherein each of the dashed lines independently represents either a covalent bond between the nucleotides located on either side thereof or the absence of any such bond; and wherein (X)$_{L2}$ represents an oligonucleotide which may be present or absent with the proviso that L2 represents an integer which is greater than or equal to 3 if (X)$_{L2}$ is present.

29. A compound having the formula:

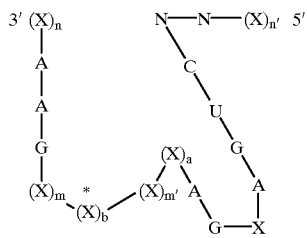

wherein each X and each N represents a nucleotide which may be the same or different and may be substituted or modified in its sugar, base or phosphate;

wherein each of A, C, U, and G represents a ribonucleotide which may be substituted or modified in its sugar, phosphate or base:

wherein each of (X)$_n$ and (X)$_{n'}$ represents an oligonucleotide having a predetermined sequence which hybridizes with an RNA target sequence to be cleaved, and each of (X)$_n$ and N—N—(X)$_{n'}$ does not naturally occur covalently bound to the sequences 3'-A-A-G-5' and 5'-C-U-G-A-3', respectively, such RNA target sequence not being present within the compound;

wherein each N represents a nucleotide which hybridizes with the RNA target sequence;

wherein one or more nucleotides of (X)$_{n'}$ do not hybridize to the RNA target sequence;

wherein each of n and n' represents an integer which defines the number of nucleotides in the oligonucleotide with the proviso that n' is at least 2 and the sum of n+n' is greater than 12;

wherein each * represents base pairing between the nucleotides located on either side thereof;

wherein each solid line represents a chemical linkage providing covalent bonds between the nucleotides located on either side thereof;

wherein a represents an integer which defines a number of nucleotides with the proviso that a may be 0 or 1 and if 0, the A located 5' of (X)$_a$ is bonded to the X located 3' of (X)$_a$;

wherein each m and m' represents an integer which is greater than or equal to 4; and wherein (X)$_b$ represents an oligonucleotide which may be present or absent with the proviso that b represents an integer which is greater than or equal to 4 if (X)$_b$ is present.

30. The compound of claim 29, wherein the oligonucleotide 3'-(X)$_n$- is 3'-(X)$_{n-1}$-A-.

31. The compound of claim 29, wherein the oligonucleotide 3'-$(X)_n$- is 3'-$(X)_{n-2}$—C-A-.

32. The compound of claim 29, wherein $(X)_a$ is absent.

33. The compound of claim 29, wherein $(X)_b$ is present.

34. The compound of claim 29, wherein the integer b of $(X)_b$ is equal to 4.

35. The compound of claim 29, wherein each of m and m' are 4.

36. The compound of claim 29, wherein the oligonucleotide $(X)_b$ has the sequence 5'-G-U-G-A-3'.

37. A composition which comprises a compound of claim 29 in association with a carrier.

38. An oligonucleotide transfer vector containing a nucleotide sequence which on transcription gives rise to any of the compounds recited in claim 29.

39. The transfer vector of claim 38, wherein the transfer vector is selected from a group consisting of a bacterial plasmid, a bacteriophage DNA, a cosmid, and an eukaryotic viral DNA.

40. A host cell transformed by the transfer vector of claim 38.

41. The host cell of claim 40, wherein the host cell is a prokaryotic host cell or an eukaryotic host cell.

42. The prokaryotic host cell of claim 41, wherein the prokaryotic host cell is an *E. coli* host cell.

43. The eukaryotic host cell of claim 41, wherein the eukaryotic host cell is a monkey COS host cell, a Chinese hamster ovary host cell, a mammalian host cell or a plant host cell.

44. The compound of claim 29, wherein the sixth nucleotide from the 3' end of $(X)_{n'}$ does not hybridize to the RNA target sequence.

45. The compound of claim 29, wherein the third, fourth, firth, and sixth nucleotides from the 3' end of $(X)_{n'}$ do not hybridize to the RNA target sequence.

46. The compound of claim 29, wherein the first nucleotide from the 3' end of $(X)_{n'}$ does not hybridize to the RNA target sequence.

* * * * *

```
                       SEQUENCE LISTING (1) GENERAL INFORMATION:

(iii) NUMBER OF SEQUENCES: 31

(2) INFORMATION FOR SEQ ID NO:1:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: Other Nucleic Acid (xi) SEQUENCE DESCRIPTION: SEQ ID NO:1:

GCCAGCUCCC                                                                10

(2) INFORMATION FOR SEQ ID NO:2:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: Other Nucleic Acid (xi) SEQUENCE DESCRIPTION: SEQ ID NO:2:

GGGAGCUGGC                                                                10

(2) INFORMATION FOR SEQ ID NO:3:

(i) SEQUENCE CHARACTERISTICS:
         (A) LENGTH: 10 base pairs
         (B) TYPE: nucleic acid
```

(C) STRANDEDNESS: single
            (D) TOPOLOGY: linear (ii) MOLECULE TYPE: Other Nucleic Acid (xi) SEQUENCE DESCRIPTION: SEQ ID NO:3:

GGUGAGCGGC                                                                          10

(2) INFORMATION FOR SEQ ID NO:4:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: Other Nucleic Acid (xi) SEQUENCE DESCRIPTION: SEQ ID NO:4:

GGGAGCUGGU                                                                          10

(2) INFORMATION FOR SEQ ID NO:5:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: Other Nucleic Acid (xi) SEQUENCE DESCRIPTION: SEQ ID NO:5:

GGAGCUCUAU                                                                          10

(2) INFORMATION FOR SEQ ID NO:6:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: Other Nucleic Acid (xi) SEQUENCE DESCRIPTION: SEQ ID NO:6:

GGUCUGUGGC                                                                          10

(2) INFORMATION FOR SEQ ID NO:7:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: Other Nucleic Acid (xi) SEQUENCE DESCRIPTION: SEQ ID NO:7:

GGGGAUGCGC                                                                          10

(2) INFORMATION FOR SEQ ID NO:8:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: Other Nucleic Acid (xi) SEQUENCE DESCRIPTION: SEQ ID NO:8:

GGACGGUGCC                                                                  10

(2) INFORMATION FOR SEQ ID NO:9:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: Other Nucleic Acid (xi) SEQUENCE DESCRIPTION: SEQ ID NO:9:

GGGAGCUGGA                                                                  10

(2) INFORMATION FOR SEQ ID NO:10:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: Other Nucleic Acid (xi) SEQUENCE DESCRIPTION: SEQ ID NO:10:

GGGAGCUGGG                                                                  10

(2) INFORMATION FOR SEQ ID NO:11:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: Other Nucleic Acid (xi) SEQUENCE DESCRIPTION: SEQ ID NO:11:

UUCCCCCUUU                                                                  10

(2) INFORMATION FOR SEQ ID NO:12:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: Other Nucleic Acid (xi) SEQUENCE DESCRIPTION: SEQ ID NO:12:

AAAGGGGAA                                                                   10

(2) INFORMATION FOR SEQ ID NO:13:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: Other Nucleic Acid (xi) SEQUENCE DESCRIPTION: SEQ ID NO:13:

AAAGUGGAUG                                                                10

(2) INFORMATION FOR SEQ ID NO:14:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: Other Nucleic Acid (xi) SEQUENCE DESCRIPTION: SEQ ID NO:14:

AAGGGGGGAA                                                                10

(2) INFORMATION FOR SEQ ID NO:15:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: Other Nucleic Acid (xi) SEQUENCE DESCRIPTION: SEQ ID NO:15:

AAUUGUGGGA                                                                10

(2) INFORMATION FOR SEQ ID NO:16:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: Other Nucleic Acid (xi) SEQUENCE DESCRIPTION: SEQ ID NO:16:

AAUGGGUGAA                                                                10

(2) INFORMATION FOR SEQ ID NO:17:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: Other Nucleic Acid (xi) SEQUENCE DESCRIPTION: SEQ ID NO:17:

AAUAGGGGAA                                                                10

(2) INFORMATION FOR SEQ ID NO:18:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: Other Nucleic Acid (xi) SEQUENCE DESCRIPTION: SEQ ID NO:18:

ACAGGGGGAA                                                                10

(2) INFORMATION FOR SEQ ID NO:19:

(i) SEQUENCE CHARACTERISTICS:
             (A) LENGTH: 10 base pairs
             (B) TYPE: nucleic acid
             (C) STRANDEDNESS: single
             (D) TOPOLOGY: linear (ii) MOLECULE TYPE: Other Nucleic Acid (xi) SEQUENCE DESCRIPTION: SEQ ID NO:19:

AAGCGGAGUG                                                                10

(2) INFORMATION FOR SEQ ID NO:20:

(i) SEQUENCE CHARACTERISTICS:
             (A) LENGTH: 10 base pairs
             (B) TYPE: nucleic acid
             (C) STRANDEDNESS: single
             (D) TOPOLOGY: linear (ii) MOLECULE TYPE: Other Nucleic Acid (xi) SEQUENCE DESCRIPTION: SEQ ID NO:20:

AUAGGGGAA                                                                 10

(2) INFORMATION FOR SEQ ID NO:21:

(i) SEQUENCE CHARACTERISTICS:
             (A) LENGTH: 10 base pairs
             (B) TYPE: nucleic acid
             (C) STRANDEDNESS: single
             (D) TOPOLOGY: linear (ii) MOLECULE TYPE: Other Nucleic Acid (xi) SEQUENCE DESCRIPTION: SEQ ID NO:21:

AAGGGGGAUA                                                                10

(2) INFORMATION FOR SEQ ID NO:22:

(i) SEQUENCE CHARACTERISTICS:
             (A) LENGTH: 10 base pairs
             (B) TYPE: nucleic acid
             (C) STRANDEDNESS: single
             (D) TOPOLOGY: linear (ii) MOLECULE TYPE: Other Nucleic Acid (xi) SEQUENCE DESCRIPTION: SEQ ID NO:22:

AAGAUGGGGG                                                                10

(2) INFORMATION FOR SEQ ID NO:23:

(i) SEQUENCE CHARACTERISTICS:
             (A) LENGTH: 10 base pairs
             (B) TYPE: nucleic acid
             (C) STRANDEDNESS: single
             (D) TOPOLOGY: linear (ii) MOLECULE TYPE: Other Nucleic Acid (xi) SEQUENCE DESCRIPTION: SEQ ID NO:23:

CAAGGGGGAA                                                                10

(2) INFORMATION FOR SEQ ID NO:24:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: Other Nucleic Acid (xi) SEQUENCE DESCRIPTION: SEQ ID NO:24:

TTCCCCCTTT                                                                10

(2) INFORMATION FOR SEQ ID NO:25:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: Other Nucleic Acid (xi) SEQUENCE DESCRIPTION: SEQ ID NO:25:

CCCTTTTTCG                                                                10

(2) INFORMATION FOR SEQ ID NO:26:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: Other Nucleic Acid (xi) SEQUENCE DESCRIPTION: SEQ ID NO:26:

ATCAGGCCAG                                                                10

(2) INFORMATION FOR SEQ ID NO:27:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: Other Nucleic Acid (xi) SEQUENCE DESCRIPTION: SEQ ID NO:27:

GCCAGCTCCC                                                                10

-continued (2) INFORMATION FOR SEQ ID NO:28:

(i) SEQUENCE CHARACTERISTICS:
      (A) LENGTH: 12 base pairs
      (B) TYPE: nucleic acid
      (C) STRANDEDNESS: single
      (D) TOPOLOGY: linear (ii) MOLECULE TYPE: Other Nucleic Acid (xi) SEQUENCE DESCRIPTION: SEQ ID NO:28:

AGGCCAGCTC CC                                                              12

(2) INFORMATION FOR SEQ ID NO:29:

(i) SEQUENCE CHARACTERISTICS:
      (A) LENGTH: 13 base pairs
      (B) TYPE: nucleic acid
      (C) STRANDEDNESS: single
      (D) TOPOLOGY: linear (ii) MOLECULE TYPE: Other Nucleic Acid (xi) SEQUENCE DESCRIPTION: SEQ ID NO:29:

TTCCCCCTTT TTG                                                             13

(2) INFORMATION FOR SEQ ID NO:30:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (ii) MOLECULE TYPE: Other Nucleic Acid (xi) SEQUENCE DESCRIPTION: SEQ ID NO:30:

AGGCCAGCUC                                                                 10

(2) INFORMATION FOR SEQ ID NO:31:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (ii) MOLECULE TYPE: Other Nucleic Acid (xi) SEQUENCE DESCRIPTION: SEQ ID NO:31:

NNNNNNNNNT                                                                 10